United States Patent
Bertini et al.

(10) Patent No.: US 11,874,263 B2
(45) Date of Patent: Jan. 16, 2024

(54) CALIBRATIONLESS OPERATION METHOD

(71) Applicant: NOVINIUM, LLC, Kent, WA (US)

(72) Inventors: Glen John Bertini, Fox Island, WA (US); Sumadhu Grandhi Arigala, Auburn, WA (US); Weston Philips Chapin Ford, Seattle, WA (US); Julien Raul Robert, Puyallup, WA (US)

(73) Assignee: NOVINIUM, LLC, Wilmington, DE (US)

( * ) Notice: Subject to any disclaimer, the term of this patent is extended or adjusted under 35 U.S.C. 154(b) by 0 days.

(21) Appl. No.: 17/493,726

(22) Filed: Oct. 4, 2021

(65) Prior Publication Data
US 2022/0026407 A1   Jan. 27, 2022

Related U.S. Application Data

(63) Continuation of application No. 16/162,260, filed on Oct. 16, 2018, now Pat. No. 11,231,405.

(51) Int. Cl.
| | |
|---|---|
| *G01N 33/00* | (2006.01) |
| *G08B 21/18* | (2006.01) |
| *G05B 19/042* | (2006.01) |
| *E02D 29/12* | (2006.01) |

(52) U.S. Cl.
CPC ....... *G01N 33/0063* (2013.01); *G01N 33/007* (2013.01); *G05B 19/042* (2013.01); *G08B 21/18* (2013.01); *E02D 29/12* (2013.01); *E02D 2600/10* (2013.01); *G05B 2219/24103* (2013.01); *G05B 2219/25252* (2013.01)

(58) Field of Classification Search
CPC ............ G01N 33/0063; G01N 33/007; G05B 19/042; G05B 2219/24103; G05B 2219/25252; G05B 23/0262; G05B 23/0221; G08B 21/18; G08B 29/24; E02D 29/12; E02D 2600/10
See application file for complete search history.

(56) References Cited

U.S. PATENT DOCUMENTS

| | | |
|---|---|---|
| 8,757,280 B2 | 6/2014 | Cordani |
| 9,216,308 B2 | 12/2015 | Cordani |
| 9,784,650 B1 | 10/2017 | Neathery |
| (Continued) | | |

FOREIGN PATENT DOCUMENTS

CN    102162375    8/2011

OTHER PUBLICATIONS

US 10,843,021 B2, 11/2020, Hyland (withdrawn)
(Continued)

*Primary Examiner* — Mohammad K Islam
(74) *Attorney, Agent, or Firm* — Davis Wright Tremaine, LLP; George C. Rondeau, Jr.; Heather M. Colburn

(57) ABSTRACT

A method that includes obtaining a sensor reading from a sensor installed inside an underground vault and determining whether the sensor reading is indicative of an alarm state. When the sensor reading is indicative of the alarm state, the method obtains at least one new reading and determines whether the sensor reading includes sensor drift based at least in part on the at least one new reading. The alarm state is established when the sensor reading is determined not to include sensor drift. The sensor drift is removed when the sensor reading is determined to include sensor drift.

24 Claims, 35 Drawing Sheets

(56) References Cited

U.S. PATENT DOCUMENTS

| | | | |
|---|---|---|---|
| 10,684,031 B2 | 6/2020 | Steele et al. | |
| 10,801,663 B2 | 10/2020 | Lambe | |
| 10,883,347 B2 | 1/2021 | Bertini et al. | |
| 10,883,348 B2 | 1/2021 | Bertini et al. | |
| 10,962,253 B2 | 3/2021 | Bertini et al. | |
| 11,035,770 B2 | 6/2021 | Bertini et al. | |
| 11,054,404 B2 | 7/2021 | Bertini et al. | |
| 11,060,754 B2 | 7/2021 | Bertini et al. | |
| 11,079,311 B2 | 8/2021 | Bertini et al. | |
| 2002/0184956 A1 | 12/2002 | Taylor et al. | |
| 2004/0135695 A1 | 7/2004 | Barton et al. | |
| 2007/0103324 A1 | 5/2007 | Kosuge et al. | |
| 2008/0165001 A1* | 7/2008 | Drake | G08B 29/24 340/550 |
| 2010/0007352 A1* | 1/2010 | Xie | G01R 31/086 324/501 |
| 2010/0050330 A1 | 3/2010 | Earlywine | |
| 2011/0316699 A1 | 12/2011 | Arunachalam | |
| 2013/0271751 A1 | 10/2013 | MacGregor et al. | |
| 2014/0202722 A1 | 7/2014 | Cordani | |
| 2016/0156880 A1* | 6/2016 | Teich | H04N 7/188 348/82 |
| 2017/0082573 A1 | 3/2017 | Vingerhoets et al. | |
| 2017/0284689 A1* | 10/2017 | Steele | F24F 11/63 |
| 2019/0166413 A1* | 5/2019 | Klinger | G01N 33/0063 |
| 2020/0064319 A1 | 2/2020 | Mcnulty et al. | |
| 2020/0115880 A1 | 4/2020 | Bertini | |
| 2020/0116688 A1 | 4/2020 | Bertini et al. | |
| 2020/0116693 A1 | 4/2020 | Bertini et al. | |
| 2020/0141340 A1 | 5/2020 | Malm | |
| 2020/0359935 A1 | 11/2020 | Clemensen et al. | |
| 2021/0361992 A1 | 11/2021 | Farzam et al. | |

OTHER PUBLICATIONS

Salehin et al. (An IoT Based Proposed System for Monitoring Manhole in Context of Bangladesh, IEEE, Aug. 27, 2018) (Year: 2018).*

Bertini, G., "Manhole Explosion and Its Root Causes," IEEE Electrical Insulation Magazine, 2019, 35(1):45-54.

Boettner et al., "Combustion Products from the Incineration of Plastics," Michigan University 1973, prepared for the Office of Research and Development U.S. Environmental Protection Agency, Washington D.C. 20460. EPA-670/2-73-049, 156 pages.

Garcez and Almeida, "Multidimensional Risk Assessment of Manhole Events as a Decision Tool for Ranking the Vaults of an Underground Electricity Distribution System," IEEE Transactions on Power Delivery, 2014, 29(2):624-632.

Kondo et al., ""Extended Le Chatelier's formula for carbon dioxide dilution effect on flammability limits," Journal ofHazardous Materials, 2006, A138:1-8."

Newton et al., "Manhole Monitoring solutions: safer, smarter for aging infrastructure," www.utilityproducts.com, Apr. 1, 2017, 9 pages.

Sun, Ma and Boggs, "Initiation of a Typical Network Secondary Manhole Event," IEEE Electrical Insulation Magazine, v.31.n.3, May/Jun. 2015.

W. Wagner and A. Pruβ, "The IAPWS Formulation 1995 for the Thermodynamic Properties of 25 Ordinary Water Substance for General and Scientific Use," Journal of Physical and Chemical Reference Data, Jun. 2002 , vol. 31, Issue 2, pp. 387535.

Zabetakis, Michael, "Flammability Characteristics of Combustible Gases and Vapors," 1965, U.S. Department of Interior, Bureau of Mines Bulletin 627, 130 pages.

Zhang, Boggs, et al., "The Electro-Chemical Basis of Manhole Events," IEEE Electrical Insulation Magazine, vol. 25, No. 5, Sep. 10, 2009.

Zhang, Lili "Mitigation of Manhole Events Caused by Secondary Cable Failure," University of Connecticut, 2011, 121 pages.

Zhang and Boggs, "Manhole Events Caused by Secondary Cable Insulation Breakdown," 2008 Annual Report Conference on Electrical Insulation Dielectric Phenomena, pp. 107-110.

Zhang and Boggs, "Effect of Limiting Airflow in Mitigating Combustion-Driven Manhole Events," IEEE, 2011, 27(6):37-44.

International Search Report and Written Opinion, dated Feb. 27, 2020, received in International Patent Application.

Notice of Allowance, dated Nov. 4, 2020, received in U.S. Appl. No. 16/162,260.

Notice of Allowance, dated Dec. 8, 2020, received in U.S. Appl. No. 16/190,832.

Notice of Allowance, dated Feb. 12, 2021, received in U.S. Appl. No. 16/189,639.

Non-Final Office Action, dated Feb. 22, 2021, received in U.S. Appl. No. 16/162,260.

Notice of Allowance, dated Mar. 2, 2021, received in U.S. Appl. No. 16/207,633.

Non-Final Office Action, dated Mar. 11, 2021, received in U.S. Appl. No. 16/219,137.

Information Disclosure Statement Transmittal filed herewith.

Notice of Allowance, dated Mar. 18, 2022, received in U.S. Appl. No. 16/514,530.

\* cited by examiner

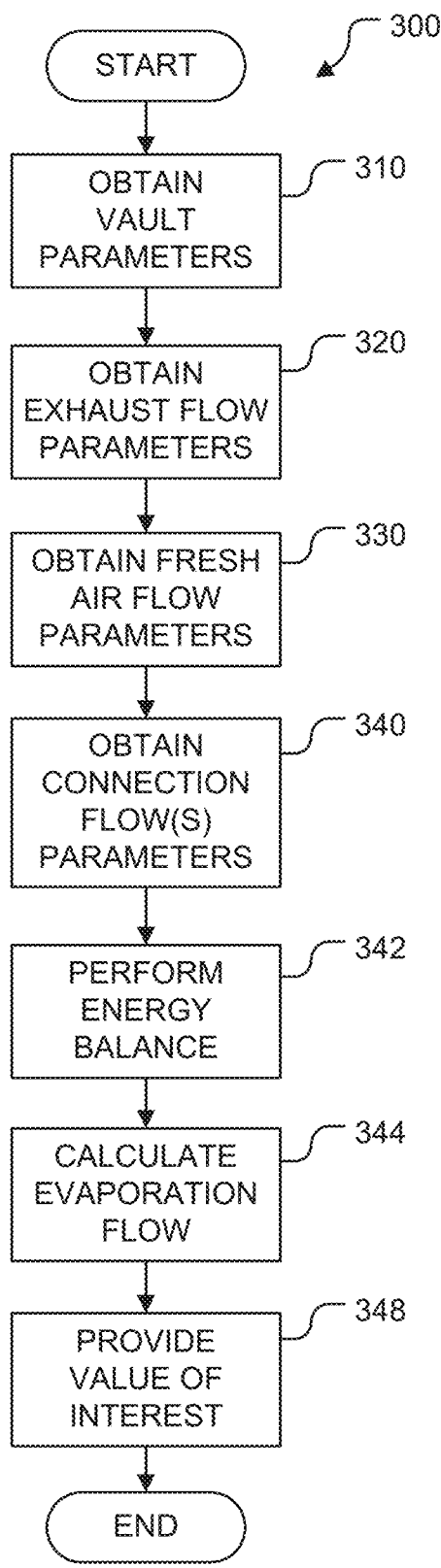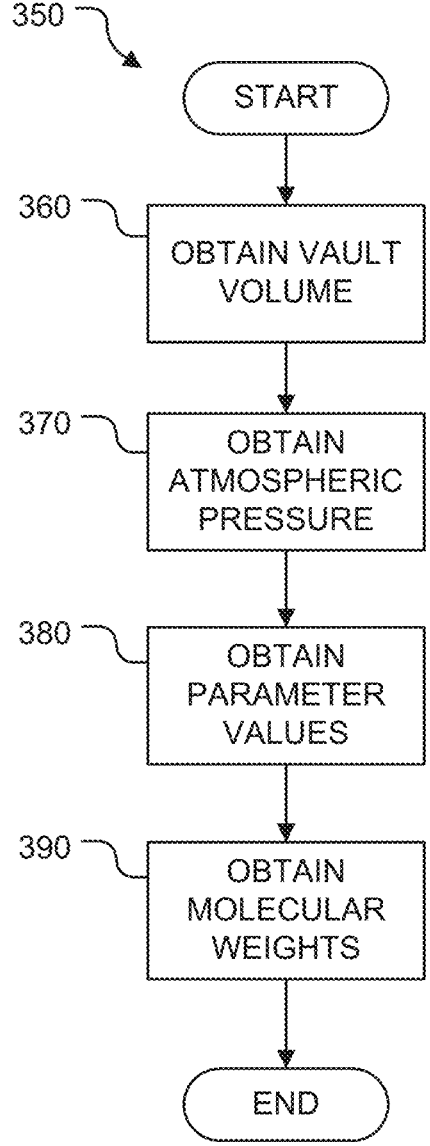
FIG. 9
FIG. 10

CALIBRATIONLESS OPERATION METHOD

CROSS-REFERENCE TO RELATED APPLICATIONS

The present application is a continuation of U.S. patent application Ser. No. 16/162,260, filed on Oct. 16, 2018, which is incorporated herein by reference in its entirety.

BACKGROUND OF THE INVENTION

Field of the Invention

The present invention is directed generally to methods of determining whether a manhole event has occurred.

Description of the Related Art

Sensor drift refers to a change in a sensor's output signal that is independent of a property being measured by the sensor. Because of sensor drift, unless a sensor is calibrated frequently, absolute values obtained by that sensor cannot be relied upon. Sensor drift is particularly acute in sensors that detect analytes and/or particulates of many different compounds (e.g., $H_2$, $CO_2$, CO, $O_2$, VOCs, $H_2S$, etc.). Sensor drift is exasperated by a challenging environment, such as the environment present inside an underground electrical cable equipment vault, where high temperatures, substantial diurnal and annual temperature variations, high humidity, and corrosive chemistry are commonplace.

Unfortunately, frequent calibration by technicians of sensors present inside underground vaults is impractical because in busy urban areas, traffic and safety considerations limit or prevent access to these environments. Such sensors are generally calibrated using calibration gases ("cal-gases"), which possess known concentrations (including zero) of a particular component of interest (analyte) in an inert carrier gas (e.g., nitrogen, argon, and the like). Unfortunately, including such cal-gases in a system designed for multi-year maintenance-free operation may be impractical as the required gas quantity may be substantial and the plumbing required carries its own reliability issues.

BRIEF DESCRIPTION OF THE SEVERAL VIEWS OF THE DRAWING(S)

FIG. 9 is a flow diagram of a second method performed by the System Controller of FIG. 1.

FIG. 10 is a flow diagram of a third method performed by the System Controller of FIG. 1.

Like reference numerals have been used in the figures to identify like components.

DETAILED DESCRIPTION OF THE INVENTION

Figure 1:
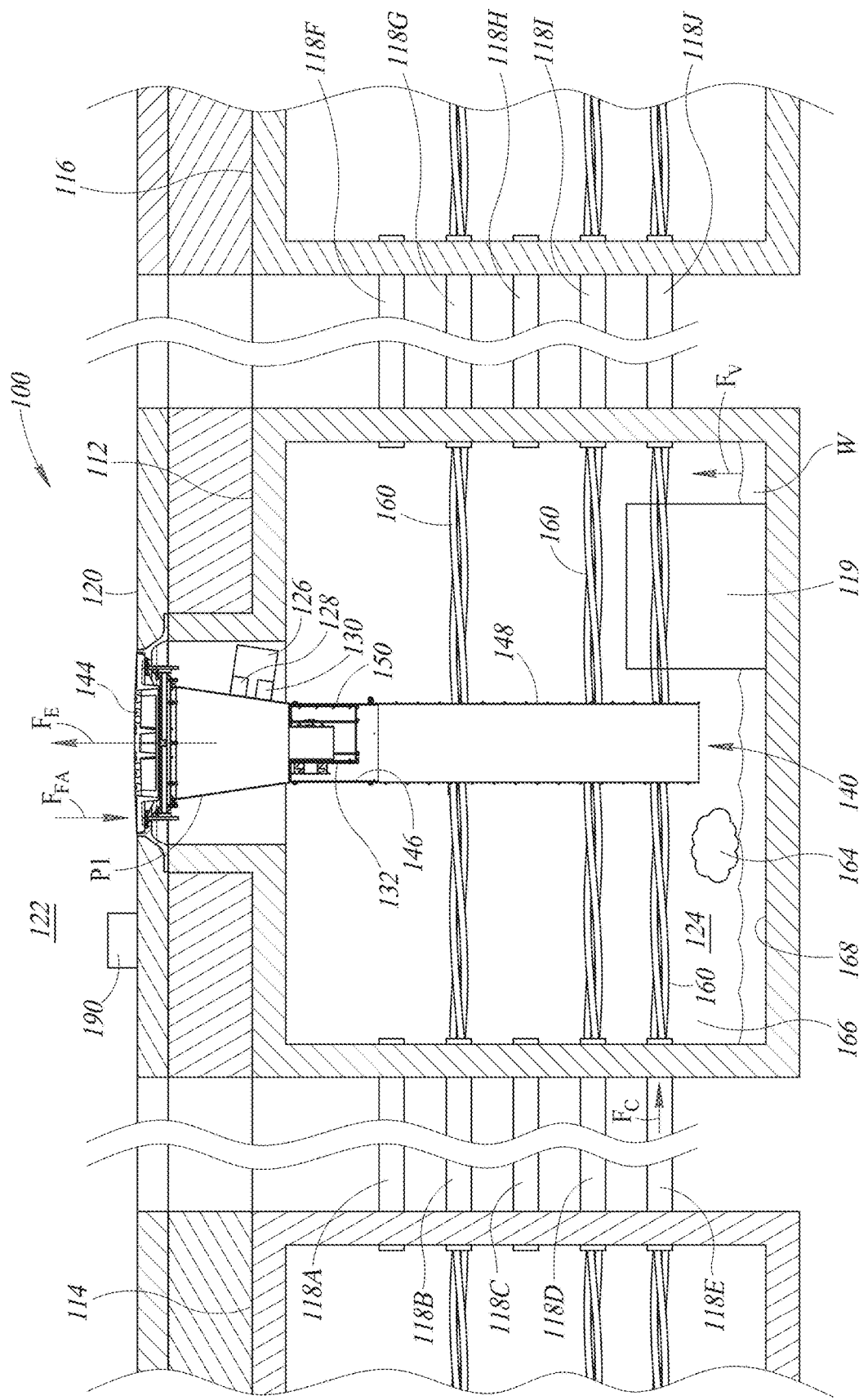
FIG. 1 is a side view of an exemplary manhole event suppression system installed in one of a plurality of manhole vaults interconnected by a plurality of conduits or connections.

Underground utilities, such as water, sewer, natural gas, electricity, telephone, cable, and steam, are a common means of delivering the essentials of modern life in a developed society. Referring to FIG. 1, such utilities are often routed through an underground system 100 that includes a plurality of substantially identical underground chambers or manhole vaults 112-116 interconnected by one or more conduits or connections 118A-118J. The vaults 112-116 may each be configured to house equipment 119, such as critical control equipment, monitoring equipment, transformers, and appropriate network connections. As shown in FIG. 1, the vaults 112-116 and the connections 118A-118J are positioned below a street or sidewalk level (identified as a surface 120). In FIG. 1, only the three vaults 112-116 of the system 100 have been illustrated. However, the system 100 may include any number of vaults each substantially similar to one of the vaults 112-116. Similarly, while the ten connections 118A-118J have been illustrated, the system 100 may include any number of connections each substantially similar to one of the connections 118A-118J.

An external atmosphere 122 exists outside the vault 112 (e.g., above the surface 120) and an internal atmosphere 124 is present inside the vault 112. For ease of illustration, air entering the vault 112 from the external atmosphere 122 will be described as being fresh air and air from the internal atmosphere 124 exiting the vault 112 into the external atmosphere 122 will be described as being exhaust. Thus, both a flow $F_{FA}$ of fresh air into the vault 112 and a flow $F_E$ of exhaust from the vault 112 may be present.

A flow Fc from one or more of the connections 118A-118J may flow into the vault 112. One or more gases created by a manhole event may travel into the vault 112 via one or more of the connection(s) flow $F_C$. When water W is present in the vault 112, an evaporation flow $F_V$ may be present inside the vault 112. The time constant T (tau) for any given underground vault (like the underground vault 112) varies with a water depth, the volume of the underground vault 112, and a flow rate of the exhaust flow $F_E$.

FIG. 1 illustrates a monitoring system 102 that includes a monitor 126 configured to communicate with a System Controller 190 via a wireless and/or wired connection. The monitor 126 is installed in the underground vault 112. The monitor 126 includes or is connected to one or more sensors 128. The monitor 126 includes other components 130 (e.g., hardware and software) that operate the sensor(s) 128. The components 130 may include one or more processors (e.g., a processor 130P) which is connected to memory 130M that stores instructions 130I. The instructions 130I are executable by the processor 130P. By way of a non-limiting example, the monitor 126 may be implemented as a data logger described in U.S. patent application Ser. No. 15/476,775, filed on Mar. 31, 2017, and titled SMART SYSTEM FOR MANHOLE EVENT SUPPRESSION SYSTEM, which is incorporated herein by reference in its entirety.

The System Controller 190 may be located remotely or collocated with respect to the monitor 126. The monitor 126 may be connected to the System Controller 190 across one or more networks (not shown).

Figure 2:
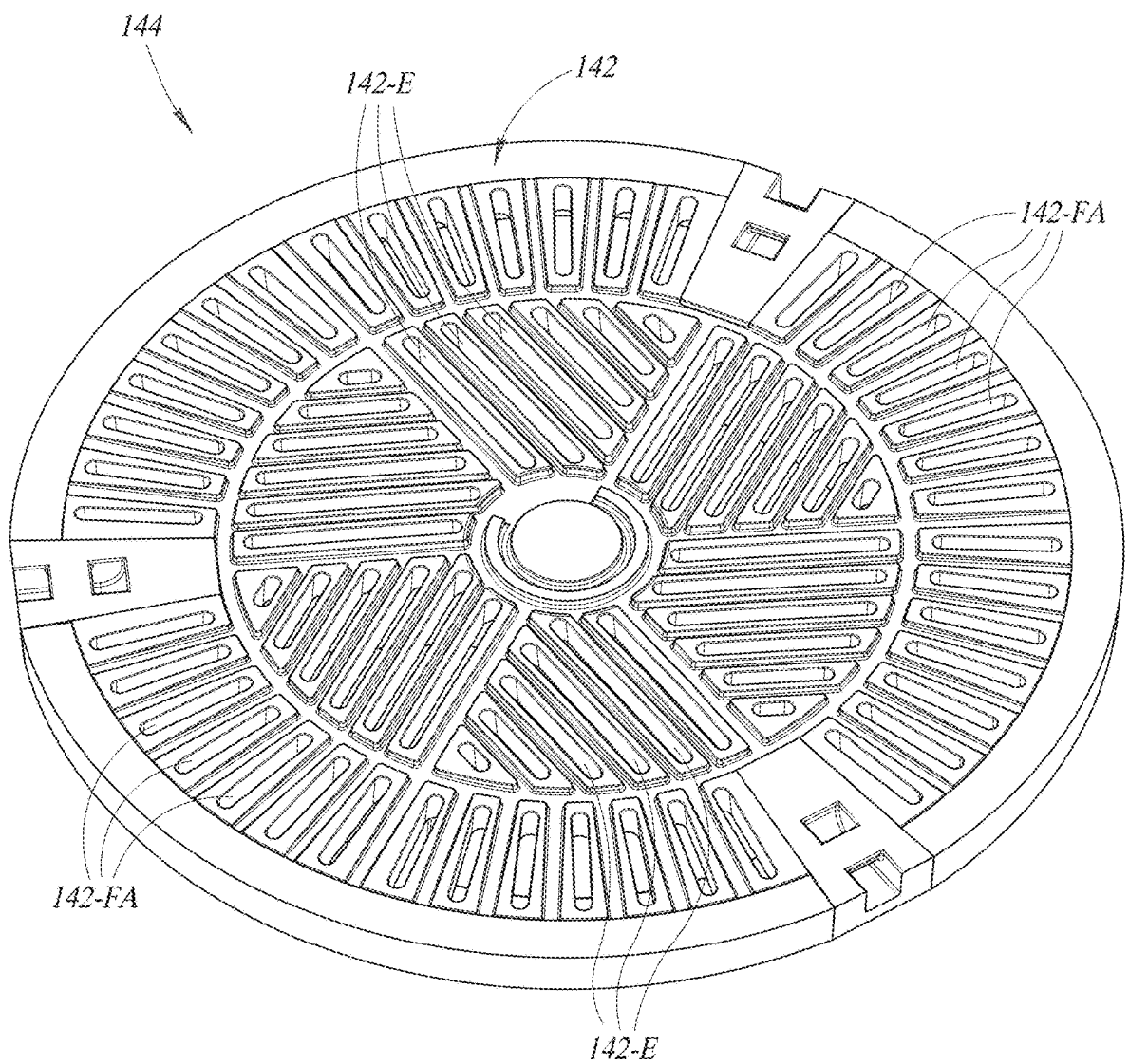
FIG. 2 is a perspective view of a manhole cover.

The exhaust flow $F_E$ may be created as least in part by an air moving device 132 of a manhole event suppression system 140. The air moving device 132 may be configured to blow exhaust (as the flow $F_E$) out through one or more of a plurality of through-holes 142 (see FIG. 2) formed in a manhole cover 144 and/or to blow fresh air into the vault 112 through one or more of the through-holes 142. In the embodiment illustrated, the air moving device 132 is connected to the manhole cover 144 by a first section P1 of a ventilation pipe 148. An inner portion 142-E (see FIG. 2) of the through-holes 142 (see FIG. 2) are positioned inside the first section P1 and an outer portion 142-FA (see FIG. 2) of the through-holes 142 are positioned outside the first section P1.

The monitor 126 may be positioned in the fresh air flow $F_{FA}$. If the air moving device 132 is configured to exhaust air through the inner portion 142-E (see FIG. 2) of the through-holes 142 (see FIG. 2), the monitor 126 may be attached to an outer surface 150 of the air moving device 132 and/or the first section P1. In this manner, the monitor 126 is within the fresh air flow $F_{FA}$ as it enters the vault 112. On the other hand, if the air moving device 132 is drawing fresh air in through the inner portion 142-E (see FIG. 2) of the through-holes 142 (see FIG. 2), the monitor 126 may be attached to an inner surface 146 of the air moving device 132 and/or the first section P1 so that the monitor 126 is in intimate contact with the fresh air flow $F_{FA}$ entering the outer portion 142-FE (see FIG. 2) of the through-holes 142. In this manner, the monitor 126 is within the fresh air flow $F_{FA}$ as it enters the vault 112. Alternatively, the monitor 126 may be mounted to the vault 112 (e.g., on a vault wall). Generally speaking, the fresh air flow $F_{FA}$ is always cooler than the exhaust flow $F_E$. Electrical components of the monitor 126 may function better at lower temperatures. By way of a non-limiting example, the monitor 126 may be positioned between the fresh air flow $F_{FA}$ and the exhaust flow $F_E$ so that less plumbing is needed to sample both the fresh air flow $F_{FA}$ and the exhaust flow $F_E$.

Alternatively, the monitor 126 may be positioned in the exhaust flow $F_E$. If the air moving device 132 is configured to exhaust air through the inner portion 142-E (see FIG. 2) of the through-holes 142 (see FIG. 2), the monitor 126 may be attached to the inner surface 146 of the air moving device 132 and/or the first section P1. In this manner, the monitor 126 is within the exhaust flow $F_E$ before it leaves the vault 112. On the other hand, if the air moving device 132 is drawing fresh air in through the inner portion 142-E (see FIG. 2) of the through-holes 142 (see FIG. 2), the monitor 126 may be attached to the outer surface 150 of the air moving device 132 and/or the first section P1 so that the monitor 126 is in intimate contact with the exhaust flow $F_E$ exiting through the outer portion 142-$F_E$ (see FIG. 2) of the through-holes 142. In this manner, the monitor 126 is within the exhaust flow $F_E$ before it leaves the vault 112. Alternatively, the monitor 126 may be mounted to the vault 112 (e.g., on a vault wall).

Figure 3:
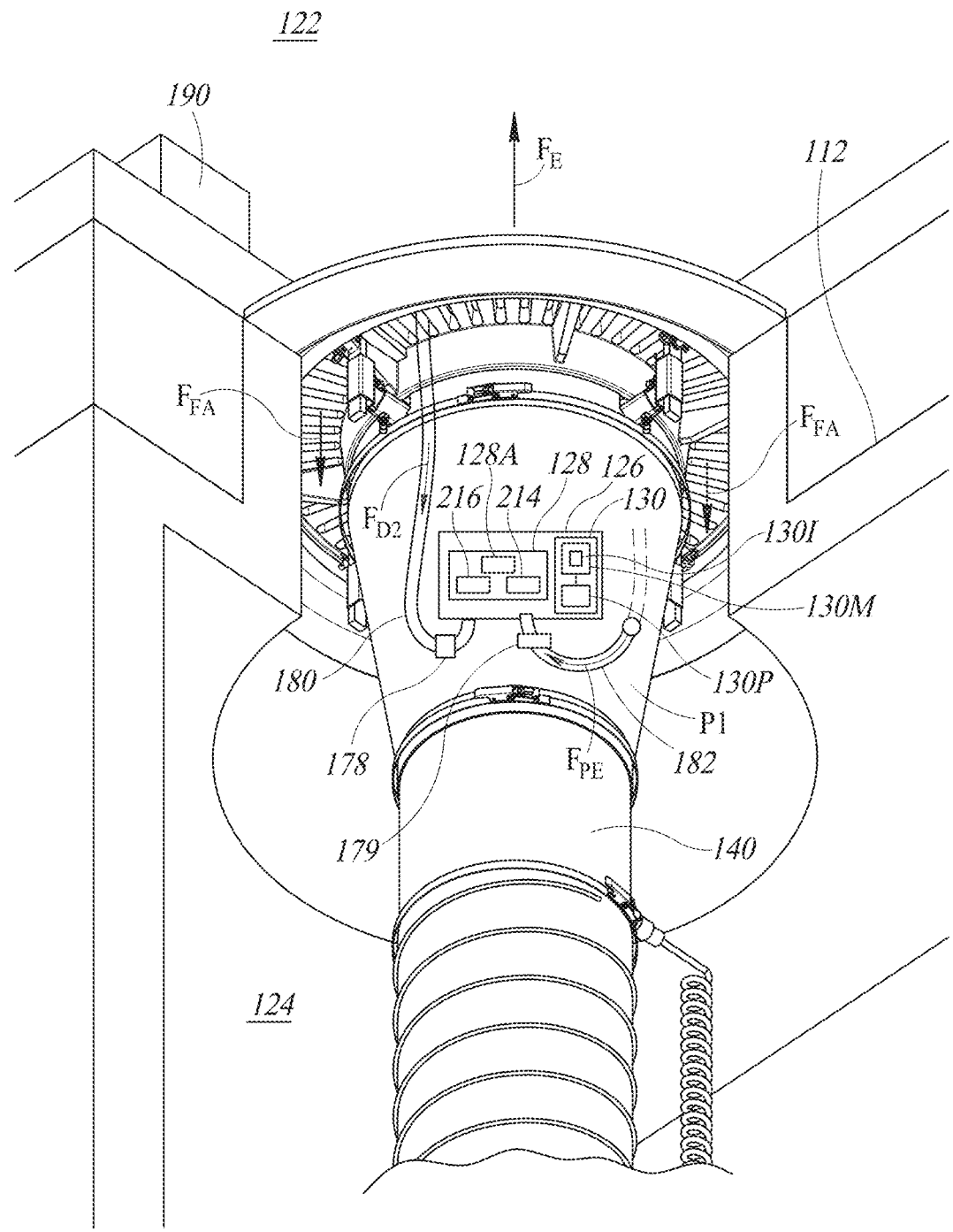
FIG. 3 is an enlarged perspective view of the monitor installed in the underground vault connected to a System Controller.

Referring to FIG. 3, the sensor(s) 128 may include a water level sensor 214 and at least one fire detection sensor 216 together with hardware and software configured to operate the sensors 214 and 216. The fire detection sensor(s) 216 may include a temperature sensor, a humidity sensor, a visible light camera, an infra-red camera, a motion sensor, a particulate sensor, a smoke sensor or detector, and a chemical concentration sensor. Examples of chemical concentration sensors that may be used to implement one or more of the fire detection sensor(s) 216 include sensors configured to detect $O_2$, $CO_2$, CO, $H_2$, VOCs, NO, $NO_2$, particulates, and $O_3$. By way of non-limiting examples, the fire detection sensor(s) 216 may detect one or more of the following conditions, which indicate a corresponding fire or flammable gas accumulation ("FGA") specified in parenthesis:

i. $CO_2$ is elevated (oxidative decomposition);
 ii. CO is elevated (pyrolysis);
 iii. VOCs are elevated (pyrolysis or FGA);
 iv. $H_2$ is elevated (pyrolysis);
 v. NO is elevated (evidence of plasma/electrical discharge or high temperature oxidative decomposition);
 vi. $NO_2$ is elevated (evidence of plasma/electrical discharge or high temperature oxidative decomposition);
 vii. $O_3$ is elevated (evidence of plasma/electrical discharge or high temperature oxidative decomposition);
 viii. $H_2O$ (absolute humidity) is elevated (oxidative decomposition);
 ix. $O_2$ is depressed (dilution by i-vii, and consumption by oxidative decomposition and partial pyrolysis);
 x. Temperature is elevated (oxidative decomposition);
 xi. Particulates are elevated (any or all oxidative decomposition, pyrolysis, plasma/electrical discharge); and
 xii. Smoke is observed in visual or infra-red wavelengths by pattern recognition algorithms or by motion detection (any or all oxidative decomposition, pyrolysis, plasma/electrical discharge).

Referring to FIG. 1, the equipment 119 located in the underground vault 112 may include and/or be connected to cables 160. Equipment (like the equipment 119) may be located in other vaults (e.g., the vaults 114 and 116) connected to the vault 112. The electrical equipment 119 may cause manhole events. Manhole events include both minor incidents (such as smoke or small fires) and/or major events (such as sustained fires and explosions). The manhole event suppression system 140 may be installed in the underground vault 112 to help prevent manhole events. The monitor 126 is illustrated integral with the manhole event suppression system 140, but the monitor 126 may also be independent of the manhole event suppression system 140.

As mentioned above, the air moving device 132 of the manhole event suppression system 140 is configured to exchange air between the external atmosphere 122 outside the vault 112 and the internal atmosphere 124 inside the vault 112. For example, the air moving device 132 of the manhole event suppression system 140 may blow fresh air from the external atmosphere 122 into the internal atmosphere 124 and/or may exhaust air from the internal atmosphere 124 into the external atmosphere 122. Such air exchange may be referred to as active ventilation. By way of non-limiting examples, the manhole event suppression system 140 may be implemented in accordance with any of the ventilation systems described in U.S. patent application Ser. No. 15/084,321 filed on Mar. 29, 2016 (titled VENTILATION SYSTEM FOR MANHOLE VAULT), U.S. patent application Ser. No. 15/173,633, filed Jun. 4, 2016 (titled SYSTEMS FOR CIRCULATING AIR INSIDE A MANHOLE VAULT), and/or U.S. patent application Ser. No. 15/476,775, filed on Mar. 31, 2017 (titled SMART SYSTEM FOR MANHOLE EVENT SUPPRESSION SYSTEM). Each of the aforementioned patent applications is incorporated herein by reference in its entirety.

The internal atmosphere 124 may include an undesired (and potentially dangerous) gaseous composition 164. The gaseous composition 164 may be non-uniformly distributed within an interior 166 of the vault 112. For example, the gaseous composition 164 may be adjacent or near a floor 168 of the vault 112.

A sensor's output signal or readings may be inaccurate for a number of reasons, including sensor drift, noise, and the like. Sensor drift is a change in a sensor's output signal or readings that occurs over time and is independent of the thing (e.g., concentration of an analyte) being measured. Noise is random variations in the output signal or readings of a sensor. Variations caused by sensor drift and/or non-drift variations (e.g., noise) will be referred to as inconsequential variations and variations caused by a manhole event will be referred to as consequential variations. At least some of the inconsequential variations can be removed by calibrating the sensor. Unfortunately, it is not always practical to calibrate a sensor, such as one or more of the fire detection sensor(s) 216 installed in the underground vault 112. Therefore, a process referred to herein as "Calibrationless Operation," described below, may be implemented for one or more of the fire detection sensor(s) 216.

The useful life of a sensor may be extended using Calibrationless Operation. For example, a sensor package may use Calibrationless Operation to extend the life of one or more of its sensors. Calibrationless Operation involves the statistical filtering of sensor drift, noise, and the like. Sensor drift occurs slowly and independently of random sensor noise. Sensor drift is generally only significant over a period of days. Events (such as fires or natural gas leaks) that increase analytes of interest, (such as VOCs, $H_2$, CO, $H_2O$ (relative humidity), NO, $NO_2$, $O_3$, and/or $CO_2$), and sometimes cause corresponding decreases in other analytes, such as $O_2$, tend to exhibit much lower time constants—measureable in minutes or hours. Thus, increases in analytes of interest that occur within a short time period are typically not caused by sensor drift and are much more likely to indicate a manhole event is occurring.

Calibrationless Operation models past behavior of a sensor to identify drift and/or noise and avoids acting upon identified drift and/or noise. A purely statistical approach to identifying drift and/or noise presents a direct trade-off between identifying false positives and false negatives. That is, a practitioner can set a very high bar for detecting a dangerous gas, which would reduce the number of false positives, but must as a result accept a higher probability of false negatives. To overcome this tradeoff, Calibrationless Operation deploys at least one of the following three corroborating techniques: confirmatory measurement(s), complementary corroboration, and active dilution.

Confirmatory Measurement(s)

When a suspected alarm condition is detected by a sensor, at least one confirmatory measurement is made quickly after the detection. For example, multiple confirmatory measurements may be made in rapid succession to test for random variations (noise). Such confirmatory measurement(s) may be collected from the same sensor (a first sensor) or at least one corroborating sensor. A corroborating sensor is not the first sensor, but may include an identical redundant sensor, a similar sensor, and/or a complimentary sensor. Similar sensors measure the same thing as the first sensor, but using different properties. For example, CO can be measured electrochemically or by using infrared. Identical redundant sensors may use the same measuring technology as the first sensor but may be scaled differently and operated in different ranges. Complimentary sensors measure different properties from the first sensor but may be used to reach, at least in part, the same conclusion as the first sensor. Corroborating sensors may be located in the same control box as the first sensor, in a different control box in the same vault as the first sensor, or in one or more adjacent vaults.

Complementary Corroboration

Where fires are suspected (not just the accumulation of VOCs or $H_2S$) corroborating sensors may provide the corroboration to effectuate an alarm condition. As mentioned above, such corroborating sensors may be located in the same control box as the first sensor, in a different control box in the same vault as the first sensor, or in one or more adjacent vaults.

As mentioned above, complimentary sensors measure different properties from the first sensor but may be used to reach, at least in part, the same conclusion as the first sensor. Thus, whether two or more sensors are complimentary depends upon the conclusion being reached. For example, when trying to determine if a fire is present, a CO sensor is complimentary to a $CO_2$ sensor because carbon monoxide is created in any carbon dioxide ($CO_2$) generating fire. By way of another non-limiting example, when trying to determine if a fire is present, a temperature sensor is complimentary to a $CO_2$ sensor because the temperature sensor may detect an increase in temperature at the same time the $CO_2$ sensor detects an increase in $CO_2$. Corroborating sensors can be collocated in a sensor package within a single vault, located in a least one other sensor package within the single vault, and/or located in adjacent vaults.

Table A lists gaseous compounds likely to be encountered in a manhole sorted from lowest to highest density along with their lower explosive limits ("LEL") and upper explosive limits ("UEL") for flammable materials. Boettner et al, "Combustion Products from the Incineration of Plastics," Michigan University 1973, prepared for the Office of Research and Development U.S. Environmental Protection Agency, Washington D.C. 20460. EPA-670/2-73-049; "Gas Data Book," 7th Ed. 2001 by Matheson Gas Products; and "Flammability Characteristics of Combustible Gases and Vapors," 1965, U.S. Department of Interior, Bureau of Mines Bulletin 627. A leftmost column lists classes based on the compound's density: lighter-than-air ("LTA"), similar-to-air ("STA"), and heavier-than-air ("HTA"). Carbon, which is listed on the last row at the bottom of Table A, is a special case. Carbon is a solid and has a density over three orders of magnitude higher than air, but has an outsized contribution to many manhole explosions.

TABLE A

| Class | Compound | Density ($Kg/m^3$) @ STP | Density (SG @ STP) | LEL (% v) | UEL (% v) |
|---|---|---|---|---|---|
| LTA | Hydrogen | 0.09 | 0.07 | 4.0 | 75.0 |
| STA | Methane | 0.72 | 0.56 | 4.4 | 17.0 |
| STA | Water vapor | 0.80 | 0.63 | Non-flammable | Non-flammable |
| STA | Acetylene | 1.15 | 0.90 | 2.5 | 100.0 |

TABLE A-continued

| Class | Compound | Density ($Kg/m^3$) @ STP | Density (SG @ STP) | LEL (% v) | UEL (% v) |
|---|---|---|---|---|---|
| STA | Carbon Monoxide | 1.25 | 0.98 | 12.5 | 74.2 |
| STA | Nitrogen | 1.25 | 0.98 | Non-flammable | Non-flammable |
| STA | Ethylene | 1.26 | 0.98 | 2.7 | 36.0 |
| STA | Ethane | 1.26 | 0.99 | 3.0 | 12.4 |
| STA | Air | 1.28 | 1.00 | Oxidizer | Oxidizer |
| STA | Hydrogen sulfide | 1.36 | 1.06 | 4.0 | 44.0 |
| STA | Oxygen | 1.43 | 1.12 | Oxidizer | Oxidizer |
| STA | Propylene | 1.74 | 1.36 | 2.4 | 11.0 |
| STA | Propane | 1.88 | 1.47 | 2.1 | 9.5 |
| STA | Carbon dioxide | 1.98 | 1.67 | Non-flammable | Non-flammable |
| HTA | 1-butene | 2.48 | 1.94 | 1.6 | 10.0 |
| HTA | trans-2-butene | 2.50 | 1.95 | 1.7 | 9.7 |
| HTA | cis-2-butene | 2.50 | 1.95 | 1.7 | 9.7 |
| HTA | Butane | 2.57 | 2.01 | 1.8 | 8.4 |
| HTA | 1,3-pentadiene | 3.01 | 2.35 | 2.0 | 8.3 |
| HTA | 1-pentene | 3.07 | 2.40 | 1.4 | 8.7 |
| HTA | Pentane | 3.19 | 2.49 | 1.4 | 7.8 |
| HTA | 1-hexene | 3.84 | 3.00 | 1.2 | 6.9 |
| HTA | 2-hexene | 3.84 | 3.00 | 1.2 | 6.9 |
| HTA | Carbon | 2260 | 1766 | Combustible Dust | |

The fourth column above, lists a specific gravity ("SG") for each of the gaseous compounds.

Figure 4:
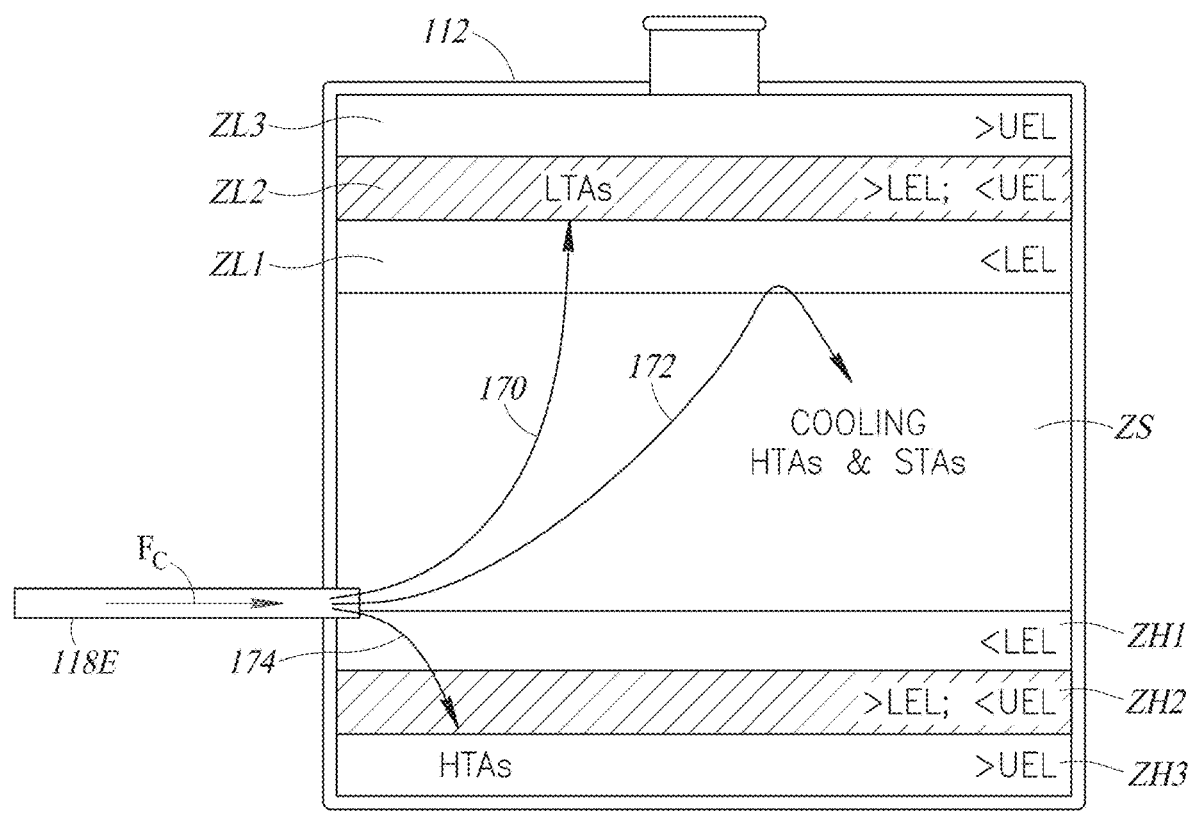
FIG. 4 is an illustration of gases entering one of the manhole vaults of FIG. 1 through a connection to the vault.

FIG. 4 illustrates each of three classes of flammable vapors entering the vault 112 from the exemplary connection 118E (e.g., a duct). An arrow 170 illustrates one or more LTA compound, an arrow 172 illustrates one or more STA compound, and an arrow 174 illustrates one or more HTA compound entering the vault 112. FIG. 4 also includes LTA zones ZL1-ZL3, a central STA zone ZS, and HTA zones ZH1-ZH3. The LTA compound(s) may gravitationally striate into the three LTA zones ZL1-ZL3 and the HTA compound(s) may gravitationally striate into the three HTA zones ZH1-ZH3. The zones ZL2 and ZH2 are combustion zones where each flammable component is above its lower explosive limit ("LEL"), but below its upper explosive limit ("UEL"). The zones ZL1 and ZL3 are below and above the combustion zone ZL2, respectively, and the zones ZH1 and ZH3 are above and below the combustion zone ZH2, respectively. In each of the zones ZL3 and ZH3, there is not enough oxygen present (i.e., the mixture is too rich; the concentration is >UEL) for the flammable component(s) to burn. In each of the zones ZL1 and ZH1, there is not enough fuel present (i.e., the mixture is too lean; the concentration is <LEL) for the flammable component(s) to burn. The STA compound(s) do not striate. Instead, they intermix with the air. While there are dynamic concentration gradients, the STA compound(s) will equilibrate toward a uniform concentration throughout the central STA zone ZS.

Once outside a specific gravity range of about 0.5 to about 2.0 and absent convective air circulation, gases may separate into the striated layers illustrated in FIG. 4. The HTA compound(s) tend to sink to the bottom of a structure (e.g., the vault 112). The LTA compound(s) tend to float to the top of the structure. The STA compound(s) fill central portions between the top and bottom of the volume not filled by the LTA and HTA compound(s). Any gravitational striation is dynamic. Dynamic considerations include the following: new gases that may enter or exit from the connection(s) flow $F_C$, gases that diffuse or leak from or to the vault 112, and gases that diffuse from one zone to an adjacent zone driven by concentration gradients against gravitational striation.

An explosion occurs when a gas or plasma expands at a rate that is equal to or faster than the speed of sound. Fire is a complex set of physical and chemical reactions. Almost all of the plastics, polymers, and rubbers that the electrical industry uses are dominated by a single repeating polymeric unit. A non-limiting example of such a polymeric unit is methylene, which includes a single carbon atom, two hydrogen atoms, and two unpaired electrons represented thusly: —CH$_2$—. There is little difference between all of the different types of polyethylene ("PE") including high molecular weight PE ("HMWPE"), cross-linked PE ("XLPE"), Linear-Low Density PE ("LLDPE"), Low Density PE ("LDPE"), High Density PE ("HDPE") and Tree-Retardant cross-linked PE ("TRXLPE") when it comes to their burn chemistry.

If electricity is not involved, there are only two kinds of burning: oxidative decomposition and pyrolysis. When electrical discharges are involved, a third kind of burning, plasmatization (and its reverse), may be present. These three kinds of burning usually occur in the following order: plasmatization, pyrolysis, and oxidative decomposition.

Oxidative decomposition is represented by Equation 1 below and is what most people think of when they contemplate the chemistry of fire.

$$2\text{-CH}_2\text{-}+3O_2 \rightarrow CO_2+2H_2O \tag{1}$$

Pyrolysis is thermal anaerobic (in the absence of oxygen) decomposition of methylene. Pyrolysis may be represented by Equation 2 below.

$$\alpha\text{-CH}_2 \rightarrow \beta C+\gamma H_2+\delta C_n H_m \tag{2}$$

In Equation 2 above, Greek letters represent integers that satisfy an atom balance that varies greatly depending on conditions. The variable "n" represents a small integer and the variable "m" represents a numerical value between 1 and 3 times the value of the variable "n."

Figure 5:
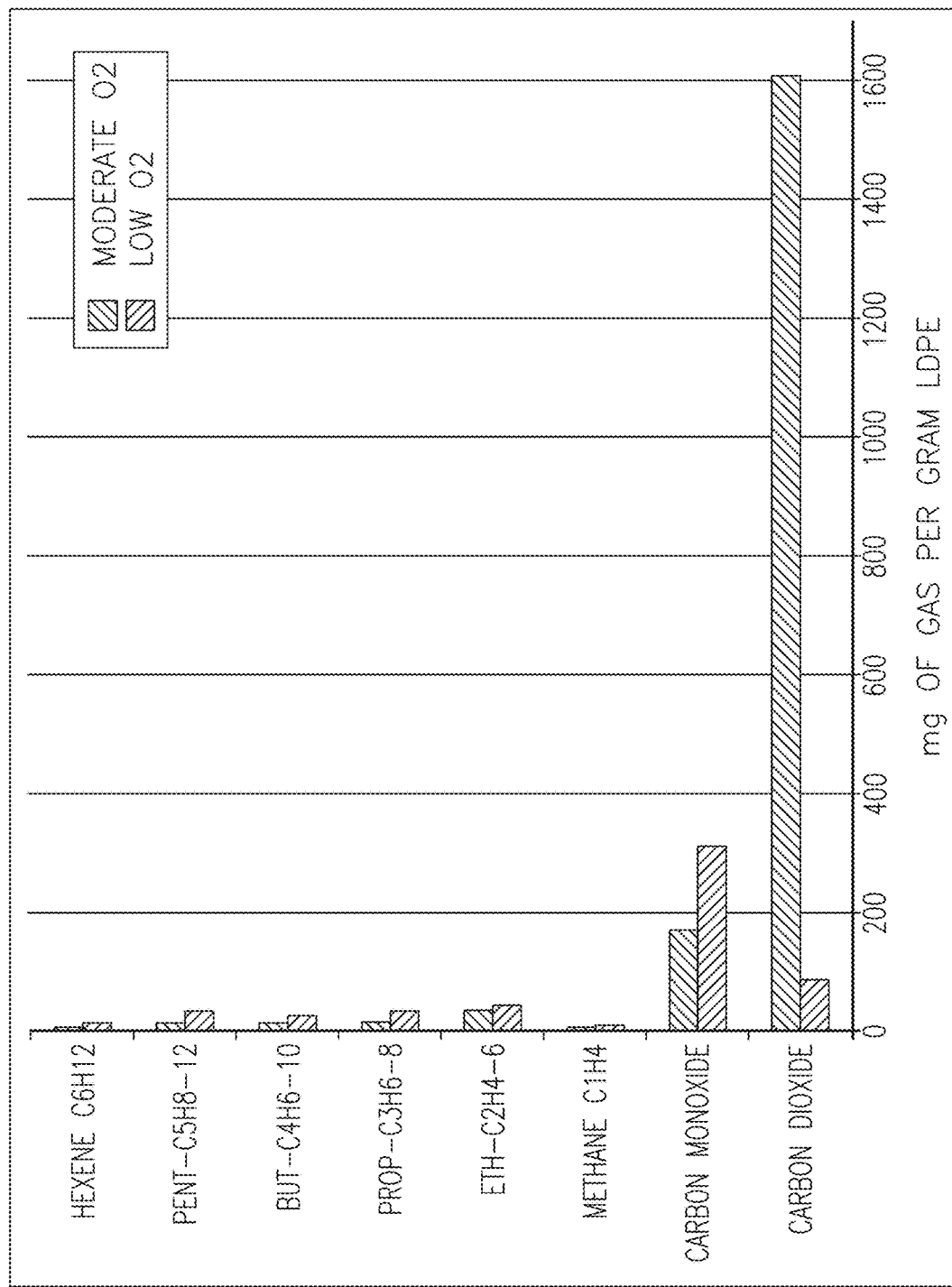
FIG. 5 is a bar graph illustrating an accounting of different gaseous combustion-pyrolysis products of low density polyethylene ("LDPE") powder taken from Boettner et al, "Combustion Products from the Incineration of Plastics" Michigan University 1973, prepared for the Office of Research and Development U.S. Environmental Protection Agency, Washington D.C. 20460, EPA-670/2-73-049.

FIG. 5 is an accounting of different gaseous combustion-pyrolysis products of low density polyethylene ("LDPE") powder taken from Boettner et al, "Combustion Products from the Incineration of Plastics" Michigan University 1973, prepared for the Office of Research and Development U.S. Environmental Protection Agency, Washington D.C. 20460, EPA-670/2-73-049. Non-definitive compound designations listed on the y-axis indicate that more than a single species is included. For example, C$_2$H$_{4-6}$ includes ethane (C$_2$H$_6$) and ethylene (C$_2$H$_4$). Elemental carbon, water, and hydrogen were not measured by the researchers and are not shown in FIG. 5.

Figure 6:
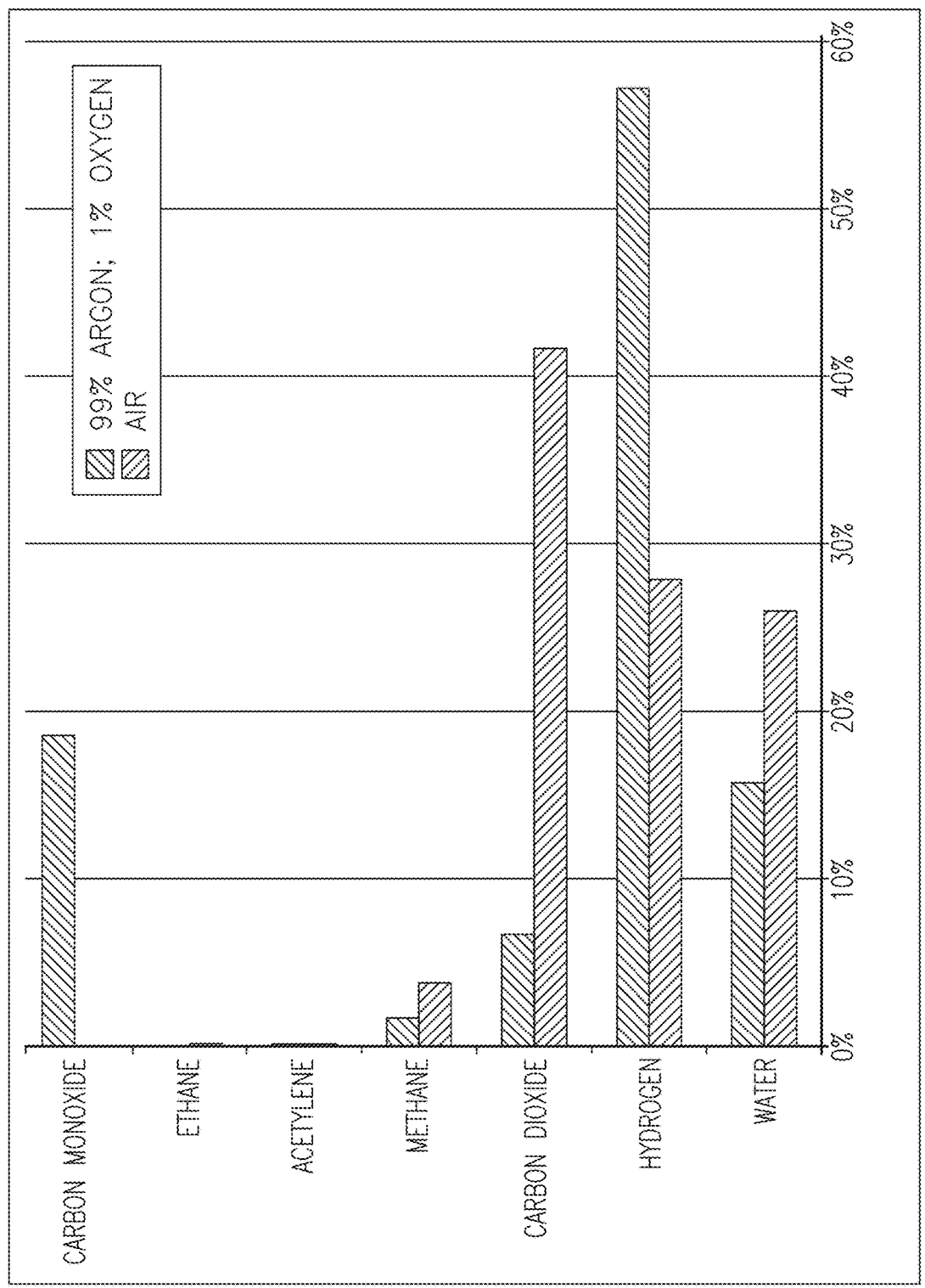
FIG. 6 is a bar graph of a residual gas analyzer ("RGA") result that quantifies water evolved from combustion/pyrolysis of rubber compounds taken from Zhang, Boggs, et al, "The Electro-Chemical Basis of Manhole Events," IEEE Electrical Insulation Magazine, Vol. 25, No. 5, September-October 2009.

FIG. 6 is a residual gas analyzer ("RGA") result that quantifies water evolved from combustion/pyrolysis of rubber compounds taken from Zhang, Boggs, et al, "The Electro-Chemical Basis of Manhole Events," IEEE Electrical Insulation Magazine, Vol. 25, No. 5, September-October 2009. RGA suffers from an inability to resolve CO if N$_2$ is present as well as to resolve elemental carbon. Note that the x-axis of FIG. 6 is not the same as FIG. 5. Here the abundance of each gas is a normalized volume. Differences between FIG. 6 and FIG. 5 include: fuel (which is SBR/EPR insulation in FIG. 6), temperature conditions, oxygen concentration, and the analytical technique. Additionally, the analytical technique employed to obtain the data of FIG. 5 was blind to water vapor and the technique used to obtain the data of FIG. 6 was blind to carbon monoxide when nitrogen was present. Both analytical techniques are blind to elemental carbon.

The data of FIGS. 5 and 6 are reconciled by acknowledging that neither representation is perfect, but both yield similar and complimentary results.

FIGS. 5 and 6 show a relative abundance of the compounds that are formed by pyrolysis. Most likely, every compound that could be formed is formed, but some compounds are simply present in a concentration that is too low to be identified. A polymer, like XLPE, does not burn directly. Instead, the polymer undergoes pyrolysis when it is heated and thus generates gases like those implied by Equation 2. After pyrolysis occurs, the resulting gaseous compounds can mix with oxygen and undergo oxidative decomposition. Equation 1 does a fine job of representing the net reaction if there is plenty of oxygen present. Incomplete combustion occurs when there is not enough oxygen present to produce the carbon dioxide and water of Equation 1. Such incomplete combustion is partially represented by Equation 3 below.

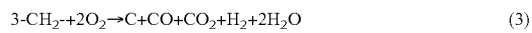

$$3\text{-CH}_2\text{-}+2O_2 \rightarrow C+CO+CO_2+H_2+2H_2O \tag{3}$$

Equation 3 properly balances for the combustion-pyrolysis case where there are precisely two oxygen molecules for every three methylene units. The fuel and the oxygen are not well mixed in duct-manhole scenarios. Less oxygen generates more carbon (the black in black smoke), more carbon monoxide, and more hydrogen at the expense of carbon dioxide and water. FIGS. 5 and 6 display the messy reality that occurs when oxidative decomposition, pyrolysis, and incomplete combustion occur simultaneously as represented by Equations 1-3.

Turning now to the third kind of burning, namely plasmatization and its reverse, an electrical arc has a temperature of between 16,900° K (30,000° F.) and 28,000° K (50,000° F.). At these temperatures, the chemistry is entirely different from what is described above. Every atom is torn from every other atom and many electrons are ripped from their nuclei. Equation 4 below shows the net result of these first two steps.

$$—CH_2— + N_2 + O_2 \rightarrow C^{\gamma+} + 2H^+ + 2N^{\nu+} + 2O^{o+} + \varepsilon e^- \tag{4}$$

where . . .

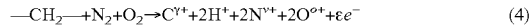

$$\varepsilon=\gamma+2+2\nu+2o \tag{5}$$

The precise charge of every atom on the right side of Equation 4 above is dependent on the temperature of the plasma and hence the value of epsilon. The number of free electrons balances the positive charges as shown by Equation 5 above. Hydrogen has only a single electron to contribute to the plasma cloud. Carbon, nitrogen, and oxygen have 6, 7, and 8 electrons respectively. Each incremental electron is more difficult to strip than the previous electron and requires a higher temperature to do so. Other atom(s) and/or molecule(s) that is/are consumed in the arc flash are not shown in FIG. 6. Clay fillers in EPR insulation, aluminum and copper conductors and neutrals, water, carbon black, and anything else nearby are broken into their respective constituent atoms and electrons are stripped from their outermost orbitals.

Plasma cannot burn. The atoms are too hot to react with each other.

Three lessons may be gained from the three kinds of burning. The first lesson involves burning and explosion. All burning involves both pyrolysis and combustion as a minimum. Where combustion predominates, smoke is clear or white (water vapor). Where pyrolysis predominates, smoke is black (carbon) and includes substantial carbon monoxide.

When electricity is involved, there is some level of plasma formation. For a primary cable failure where the voltage to ground is at least several thousand volts, the plasma may be the predominant route, but there will always be some combustion (unless the environment is completely anaerobic) and some pyrolysis. For secondary cable failures where the voltage to ground is typically just several hundred volts, plasma is present, but at a subdued level compared to a brief high current primary fault. Secondary "faults" can persist for days and while the plasma, pyrolysis, and combustion proceed at a slow pace, the accumulation of flammable gases and solid carbon in confined spaces together with ample time to mix with atmospheric oxygen may create the conditions for the largest possible chemical explosions. Sun, Ma and Boggs, "Initiation of a Typical Network Secondary Manhole Event," *IEEE Electrical Insulation Magazine*, v. 31.n. 3, May/June 2015.

The second lesson involves carbon monoxide. Carbon monoxide is the largest contributor to secondary network explosions. Table A above shows carbon monoxide is an STA compound with a wide flammable range spanning 12.5% v to 74.2% v. Further, as shown in FIGS. 5 and 6, carbon monoxide is one of the most abundant gases created in the conditions likely to be encountered in a secondary network. While we cannot ignore the hydrocarbons, they are not as abundant and hence are not of the greatest concern.

The third lesson involves carbon. Carbon is the second largest contributor to secondary network explosions. As carbon plasma cools, it remains a gas until the temperature reaches about 4,098° K (6,917° F.) where it becomes a liquid. The liquid state of carbon does not last long as it solidifies at about 3,823° K (6,422° F.). After solidifying, atomic carbon has a very high surface energy as a result of its four unpaired electrons. Adjacent carbon atoms tend to agglomerate into dust particles several microns in diameter. The agglomerates have large surface areas and high porosity.

Even though the density of the solid phase of carbon is over 1,700 times the density of air, the agglomerates are predominantly gaseous voids filled with the very same gases that surround the particle. As a consequence, the bulk density places carbon agglomerates alongside HTA gases. The slightest convection currents keep the agglomerates aloft. These carbon agglomerates are what make black smoke black. Thus, although solid carbon is not gas, solid carbon agglomerates act as though they are a gas, and when the terms "gas," "gases," or "gaseous" are used herein, carbon agglomerates are included.

When mixed with air, these particles can be ignited and participate in a dust explosion. A hetero-explosion occurs when these particles are mixed with air, carbon monoxide, hydrogen, and smaller amounts of hydrocarbon gases and ignited. The yield of the hetero-explosion depends upon one or more of the following:

1. quantities of each fuel;
2. relative quantity of oxygen to each fuel;
3. relative quantities of gaseous components that retard combustion most notably including, nitrogen, carbon dioxide, and water vapor, the latter two being products of oxidative combustion;
4. uniformity of how the aforementioned items 1, 2 and 3 are mixed (e.g., better mixing yields more explosive energy); and
5. location of the ignition source relative to the center of mass of the cloud delineated by explosive limit concentration boundaries.

Active Dilution

Referring to FIG. 3, as mentioned above, the manhole event suppression system 140 may ventilate the underground vault 112. Thus, the manhole event suppression system 140 may be used to implement variable active ventilation. However, such ventilation may occur by an alternate means.

Variable active ventilation is referred to as dilution of the first type. Dilution of the first type is accomplished by changing an overall rate of atmospheric turnover in the underground vault 112. For example, doubling of the exhaust rate approximately halves a concentration of those gases that are rare in the internal atmosphere 124, but are entering the underground vault 112 from a fire event. Conversely doubling of the exhaust rate increases the concentration in the internal atmosphere 124 of those gases that are abundant in the external atmosphere 122, namely oxygen and nitrogen. It is preferable to be able to flexibly control the flow rate and direction scalably from zero to at least one hundred percent and zero to minus one hundred percent of an air movement device, but another alternative is to have two or more preset flows including for example any two values referred to as off, low, medium and high. Yet another alternative is to turn an air movement device on and off over periodic time spans (e.g. fan 100% on for 30 seconds, fan 0% for 30 seconds yields approximately a 50% flow over a 60 second period). In the event of an emergency or potentially pending emergency, it is preferred to be able to run the air movement device above its 100% design speed.

As a practical matter, a maximum exhaust rate during routine (or non-emergency) operation is constrained by public perception. A jet-like exhaust rate would be noisy and considered a nuisance. On the other hand, noise might be a desirable feature when preventing an imminent explosion. No matter what the maximum exhaust rate may be, there are circumstances where dilution of the first type will simply be unable to provide sufficient dilution to avoid the occurrence of a manhole event (e.g., a fire and/or explosion). In other words, enough of the undesired gaseous composition 164 (see FIG. 1) cannot be exhausted from the underground vault 112 (e.g., via a high duct flow event) to provide readings from the fire detection sensor(s) 216 that are within desired sensor range(s) and/or prevent a buildup of flammable gases approaching an effective lower explosive limit. Put another way, an active ventilation system (e.g., the manhole event suppression system 140) can be overwhelmed by a large influx of flammable gas(es).

Direct sample dilution is referred to as dilution of the second type. Dilution of the second type refers to fresh air (from the external atmosphere 122) intermixing with a sample portion of the exhaust that passes by the fire detection sensor(s) 216. Thus, dilution of the second type is not constrained by the range of possible exhaust rates. However, dilution of the second type does nothing to change the internal atmosphere 124 inside the underground vault 112. When it is desirable to dilute potentially explosive gases within the underground vault 112, dilution of the first type may be used to exhaust the internal atmosphere 124 up to the maximum exhaust rate. The greatest flexibility is achieved by the combination of both dilution types.

While dilution of the first type is limited to 0% to 100% of the maximum exhaust rate (or perhaps in emergency conditions a value greater than 100%), dilution of the second type is infinitely scalable. For example, a sample air moving device 178 may be used to move fresh air from the external atmosphere 122 past the fire detection sensor(s) 216. An exhausted air moving device 179 may be used to move an exhausted gas mixture from the exhaust flow $F_E$ past the fire detection sensor(s) 216. In such embodiments, one end of a tube 180 or similar conveyance conduit may be placed in fluid communication with the external atmosphere 122 or the fresh air flow $F_{FA}$. Similarly, one end of a tube 182 or similar conveyance conduit may be placed in fluid communication with the exhaust flow $F_E$. The other end of the tube 180 may deliver a flow $F_{D2}$ of fresh air to be mixed with a portion of the exhaust flow $F_E$ conducted by the tube 182, which is illustrated as a flow $F_{PE}$. The flow $F_{PE}$ mixes with the flow $F_{D2}$ in a controlled intermix ratio ("IMR") that may range from zero to infinity. The flow rates of the flows $F_{D2}$ and $F_{PE}$ may be controlled by the air moving devices 178 and 179, which may each be implemented using any of a large variety of means well known in the art. By way of a non-limiting example, the air moving devices 178 and 179 may be implemented as a pair of gas pumps and micro-flow control valves actuated by a pair of Proportional-Integral-Derivative ("PID") controllers. The set-points of the PID controllers may be determined by the monitor 126 and/or the System Controller 190.

By way of another non-limiting example, the sample air moving devices 178 and 179 may be implemented as a pair of positive displacement pumps used to obtain the IMR established by the System Controller 190. The IMR is a ratio of a first volume of exhaust air to a second volume of fresh air. The IMR may be determined using relative displacements of the positive displacement pumps and their cycle frequencies. For example, if a first positive displacement pump is drawing the flow $F_{PE}$, has a volume of 10 ml/cycle, and is operating at 10 cycles per minute, the first positive displacement pump pumps 100 ml of exhaust air every minute. If a second positive displacement pump is drawing the flow $F_{D2}$, has a volume of 5 ml/cycle, and is operating at 10 cycles per minute, the second positive displacement pump pumps 50 ml of fresh air every minute. Thus, the IMR would be two-to-one (or 100 ml to 50 ml per minute). If the first positive displacement pump was increased to 30 cycles per minute and the second positive displacement pump remained at 10 cycles per minute, the IMR would be six-to-one (or 300 ml to 50 ml per minute).

The IMR is set by the System Controller 190 to achieve three fundamental ends: (1) to determine at least one analyte of interest is nearing a limit of detectability; (2) to validate that at least one of the fire detection sensor(s) 216 in an alarm state is not in that state because of drift; and (3) to calibrate at least one of the fire detection sensor(s) 216. If an analyte is at, near, or above its upper limit of detectability for the relevant sensor(s), the IMR can be reduced to a value as low as zero. If an analyte is at, near, or below its lower limit of detectability for the relevant sensor(s), the IMR can be increased to any value, even approaching infinity, to allow each of the relevant sensor(s) to operate within its acceptable or optimal range. There may be circumstances where at least one first sensor would benefit from a low IMR, while a least one second sensor would benefit from a high IMR. In such circumstances, the System Controller 190 may alternate the IMR to get valid sensor readings from at least the first and second sensors. In circumstances where the output from the first sensor is more critical to a current condition than the output from the second sensor, the System Controller 190 may choose an IMR that keeps the more critical sensor(s) operating in an appropriate range.

Validation is a quick check for sensor drift. Because drift is independent of dilution and the IMR, any significant perturbation of the IMR will either quickly manifest itself by a change in the sensor output of the analyte or not. The former indicates the perturbation is not caused by sensor drift. On the other hand, the later indicates the perturbation is caused at least in part by sensor drift. Since the output of the sensor of interest is moving either to greater or lesser values, the IMR may be increased or decreased to exasperate rather than mitigate that movement. For example, if a CO sensor detects that the CO is increasing, which suggests that combustion has started, the System Controller 190 may increase the IMR (thus, decreasing fresh air). After the IMR is increased, if the output of the CO sensor merely drifts upwards, this perturbation would have no discernable impact. On the other hand, if there is a fire, the CO reading would increase by a significant amount. A threshold value may be used to determine whether the increase is significant. Thus, the System Controller 190 may instruct the sample air moving devices 178 and 179 to make meaningful changes to the IMR to assure that the impact on sensor output is well above a noise level for the sensor. The slope (which is the change in analyte concentration divided by the time interval) can be applied to scale a change in the IMR that will be easy to discern from the historical slope. The noise level for each of the fire detection sensor(s) 216 is continuously calculated and consequential variations are easily recognized as those sensor readings above the noise level. Perturbations of the IMR can be repeated and reversed as many times as required until the System Controller 190 has enough statistical confidence in each of the relevant sensor(s) to take action based on its output.

The third form is direct calibration. Using direct calibration the IMR is set to zero (i.e., 100% fresh air is fed to the fire detection sensor(s) 216) and either assumed atmospheric levels or measured atmospheric levels are used to calibrate the fire detection sensor(s) 216. For example $CO_2$ is generally about 400 ppm in the troposphere. Therefore, 400 ppm may be used as an assumed atmospheric level of $CO_2$. Thus, those of the fire detection sensor(s) 216 configured to measure $CO_2$ concentration may be calibrated to measure 400 ppm when the IMR is set to zero. Alternatively, other sensors that are not inside the vault 112 and can be directly calibrated using well-known and/or conventional methods can provide an actual or measured $CO_2$ level. In this manner, those of the fire detection sensor(s) 216 configured to measure $CO_2$ concentration may be calibrated to the measured $CO_2$ level when the IMR is set to zero. The measured $CO_2$ level is provided to the System Controller 190 via a wired or wireless data connection (not shown).

Dilution of both the first and second types are referred to as "active dilution." The time constant (i tau) of dilution of the first type is quite long, generally at least several minutes. On the other hand, the time constant (i tau) of dilution of the second type is quite short, generally on the order of less than 60 seconds.

Sensor drift is independent of active dilution. This independence from dilution means that it is possible to confirm drift when Calibrationless Operation uses active dilution.

Since drift is independent of dilution, actively altering the dilution rate can test the hypothesis that the alarm condition is the result of a sudden drift. A negative result to this hypothesis confirms the concentration change is bona fide.

Calibrationless Operation

Figure 7A:
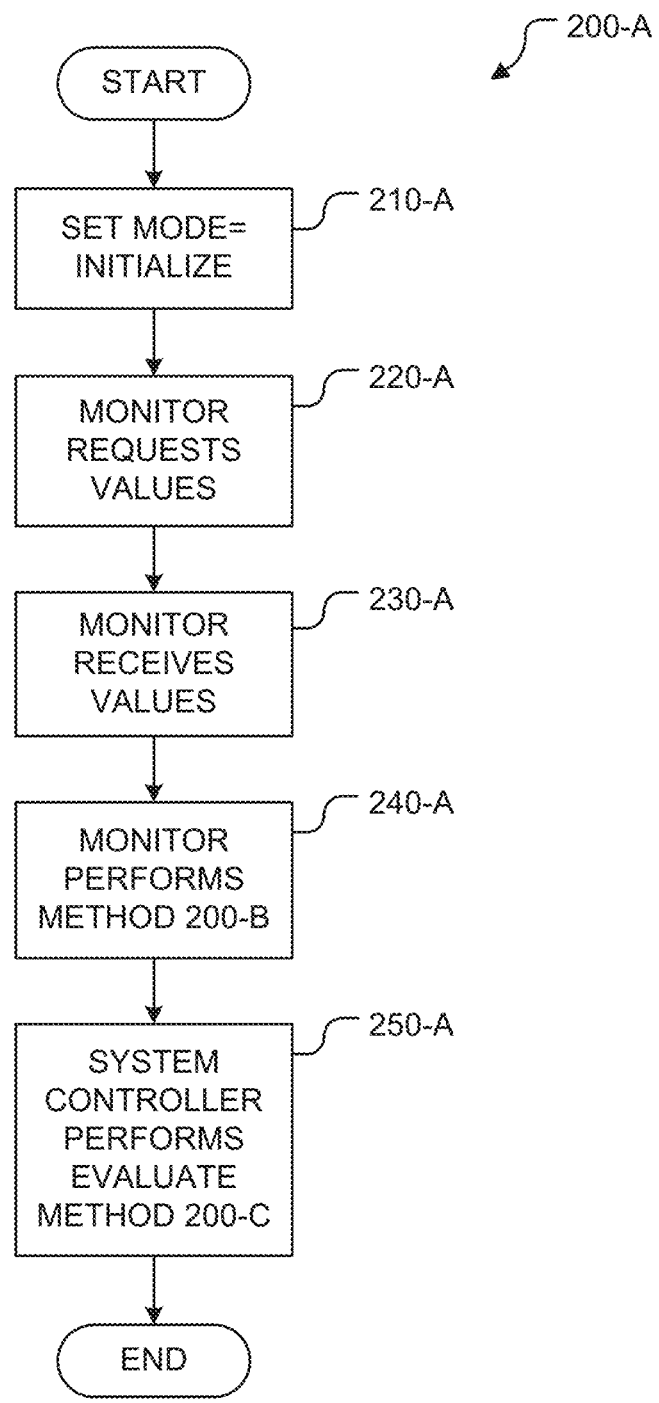
FIG. 7A is a flow diagram of a method performed by the monitoring system of FIG. 1.

FIG. 7A is a flow diagram of a method 200-A that implements Calibrationless Operation of the fire detection sensor(s) 216 installed inside the underground vault 112 (see FIG. 1). The method 200-A is performed by the monitoring system 102.

As mentioned above, the sensor(s) 128 may include the water level sensor 214 and the fire detection sensor(s) 216. The Calibrationless Operation implemented by the method 200-A may not be applicable to the water level sensor 214. In such embodiments, the method 200-A may be performed with respect to only the fire detection sensor(s) 216. For ease of illustration, the method 200-A will be described as being performed with respect to only a sensor 128A (see FIG. 3), which is one of the fire detection sensor(s) 216. However, the fire detection sensor(s) 216 may include any number of sensors and the method 200-A may be performed with respect to any number of sensors.

Figure 7B:
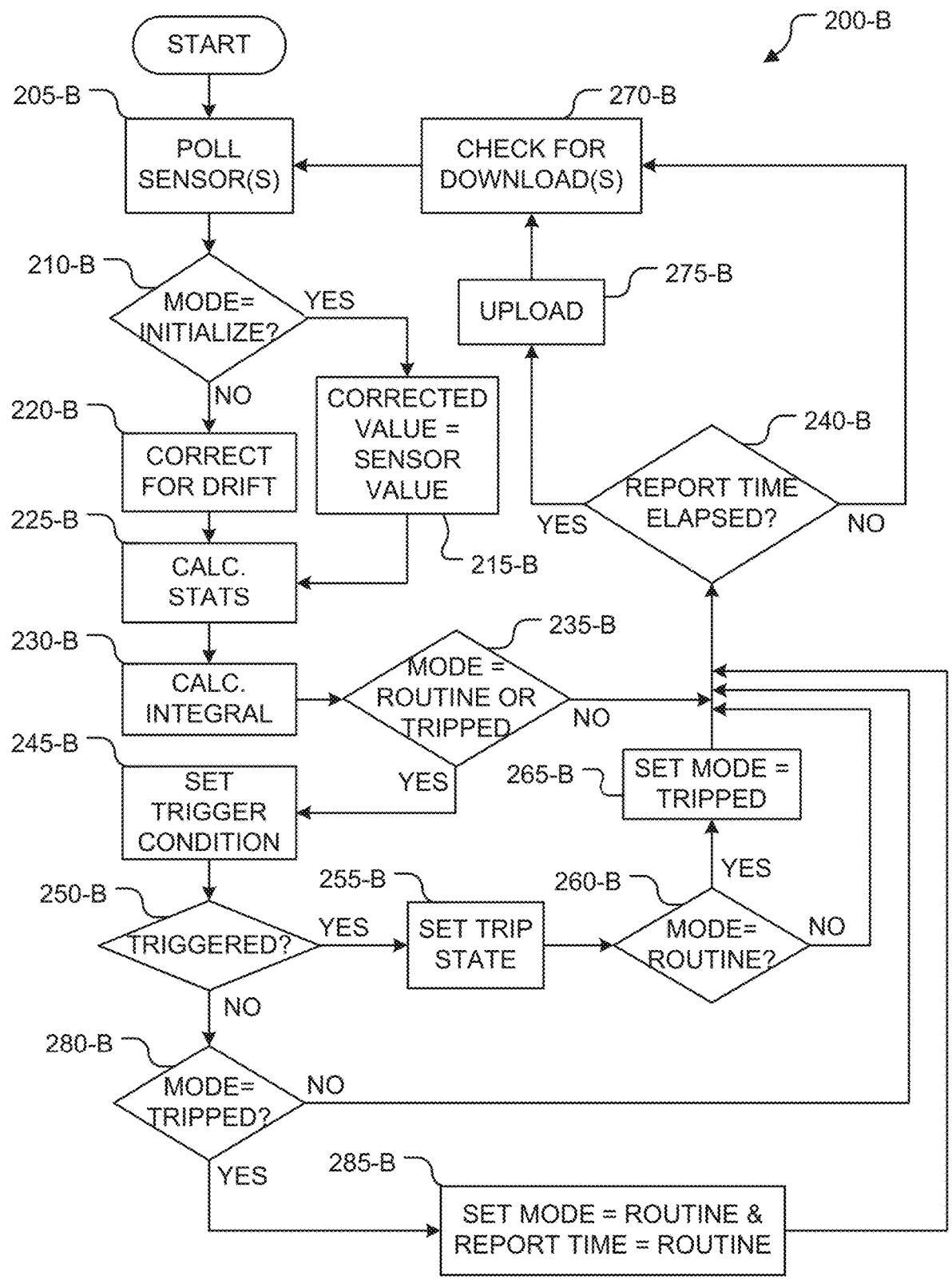
FIG. 7B is a flow diagram of a method performed by a monitor of FIG. 1.
Figure 7C:
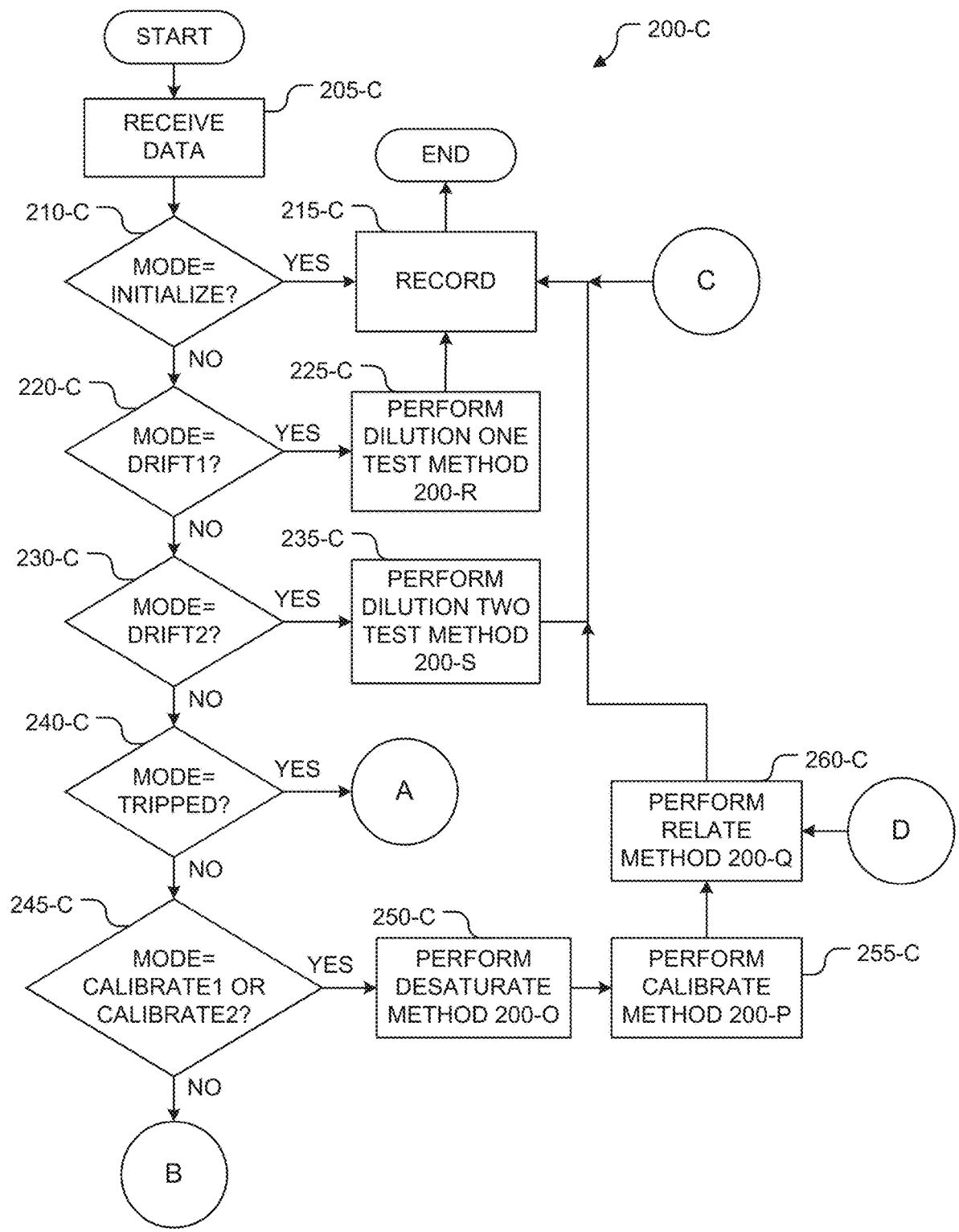
FIG. 7C is a first portion of a flow diagram of an evaluate method performed by the System Controller of FIG. 1.

The System Controller 190 (see FIGS. 1 and 3) records a mode associated with the sensor 128A (see FIG. 3) each time block 215-C (see FIG. 7C) is performed for the sensor 128A in an evaluate method 200-C (see FIG. 7C). Thus, a number of mode values may be stored for the sensor 128A (see FIG. 3). For example, the System Controller 190 (see FIGS. 1 and 3) stores a current $mode_t$ and a previous $mode_{t-1}$ for the sensor 128A (see FIG. 3). The previous $mode_{t-1}$ stores the mode value immediately preceding the current $mode_t$. In first block 210-A, the System Controller 190 (see FIGS. 1 and 3) sets both the current $mode_t$ and the previous $mode_{t-1}$ of the sensor 128A (see FIG. 3) equal to INITIALIZE.

In block 220-A, the monitor 126 sends a request to the System Controller 190 (see FIGS. 1 and 3) for flag values and system parameters. In alternative embodiments, the System Controller 190 may push the flag values and system parameters to the monitor 126. In such embodiments, the block 220-A may be omitted.

In block 230-A, the System Controller 190 sends the flag values and system parameters to the monitor 126. For example, the System Controller 190 sends the current $mode_t$ is equal to INITIALIZE to the monitor 126. The monitor 126 stores these values in the memory 130M.

The flag values may include the current $mode_t$, the previous $mode_{t-1}$, a Trigger Condition ("TC"), a trip state ("TS"), a report time, an event type indicator, and an Alarm State ("AS") associated with each of the fire detection sensor(s) 216 (e.g., the sensor 128A illustrated in FIG. 3). The current $mode_t$ and the previous $mode_{t-1}$ may each be set to one of a plurality of mode values. By way of a non-limiting example, the plurality of mode values may include INITIALIZE, ROUTINE, TRIPPED, CALIBRATE1, CALIBRATE2, DRIFT1, and DRIFT2.

The TC may be set to one of a plurality of Trigger Condition values. By way of a non-limiting example, the TC may be set to a triggered value (e.g., one) or a not triggered value (e.g., zero). Non-limiting illustrative examples of the kinds of events that might trigger alarm condition(s) include the following:

1. Oxidative Decomposition ("OD");
2. Pyrolysis ("PY");
3. Plasmatization ("PL"); and
4. Flammable gas accumulation ("FA").

Two or more of the above alarm condition(s) may be combined or collapsed for user simplicity. For example, OD, PY, and PL may be combined into a single alarm condition called Fire ("FI").

The TS may be set to one of a plurality of Trip State values. By way of a non-limiting example, the TS may be set to a not tripped value (e.g., zero), a single trip value (e.g., one), or a consecutively tripped value (e.g., two). The not tripped value (e.g., zero) indicates the sensor has not detected any potential alarm conditions (or no-event operation). The single trip value (e.g., one) indicates a first time that the single sensor 128A (see FIG. 3) has detected a single potential alarm condition. The consecutively tripped value (e.g., two) indicates that the sensor 128A (see FIG. 3) has repeatedly detected the same potential alarm condition.

The event type indicator stores one of a plurality of event type values. By way of a non-limiting example, the event type values may include a no event value, a combustion value, and an FGA (i.e., flammable gas accumulation) value.

The AS stores an alarm state value and an associated time for each of the fire detection sensor(s) 216 (e.g., the sensor 128A illustrated in FIG. 3). The alarm state value may each store one of a plurality of alarm state values. By way of a non-limiting example, the alarm state values may include a low value, an intermediate value, and a high value.

The report time may be set to one of a plurality of report time values. By way of a non-limiting example, the report time may be set to a routine value (e.g., 15 minutes) or a non-routine value (e.g., 30 seconds).

The system parameters may include a baseline Co for each of the fire detection sensor(s) 216 (e.g., the sensor 128A illustrated in FIG. 3), a baseline time for each of the fire detection sensor(s) 216, and a fan speed for an air moving device 132, an air moving device 178, and/or an air moving device 179. The fan speed may be set to one of a plurality of fan speed values. By way of a non-limiting example, the fan speed may be set to off, full (or 100%), and a numeric value corresponding to a number of consecutive seconds that the fan is on over a predetermined time period (e.g., 60 seconds).

In block 240-A, the monitor 126 performs a method 200-B (see FIG. 7B). Thus, the instructions 1301, when executed by the processor 130P, are configured to instruct the processor 130P to perform the method 200-B (see FIG. 7B). The instructions 1301, when executed by the processor 130P, may be configured to instruct the processor 130P to perform block 220-A, when present, and block 230-A.

Figure 7D:
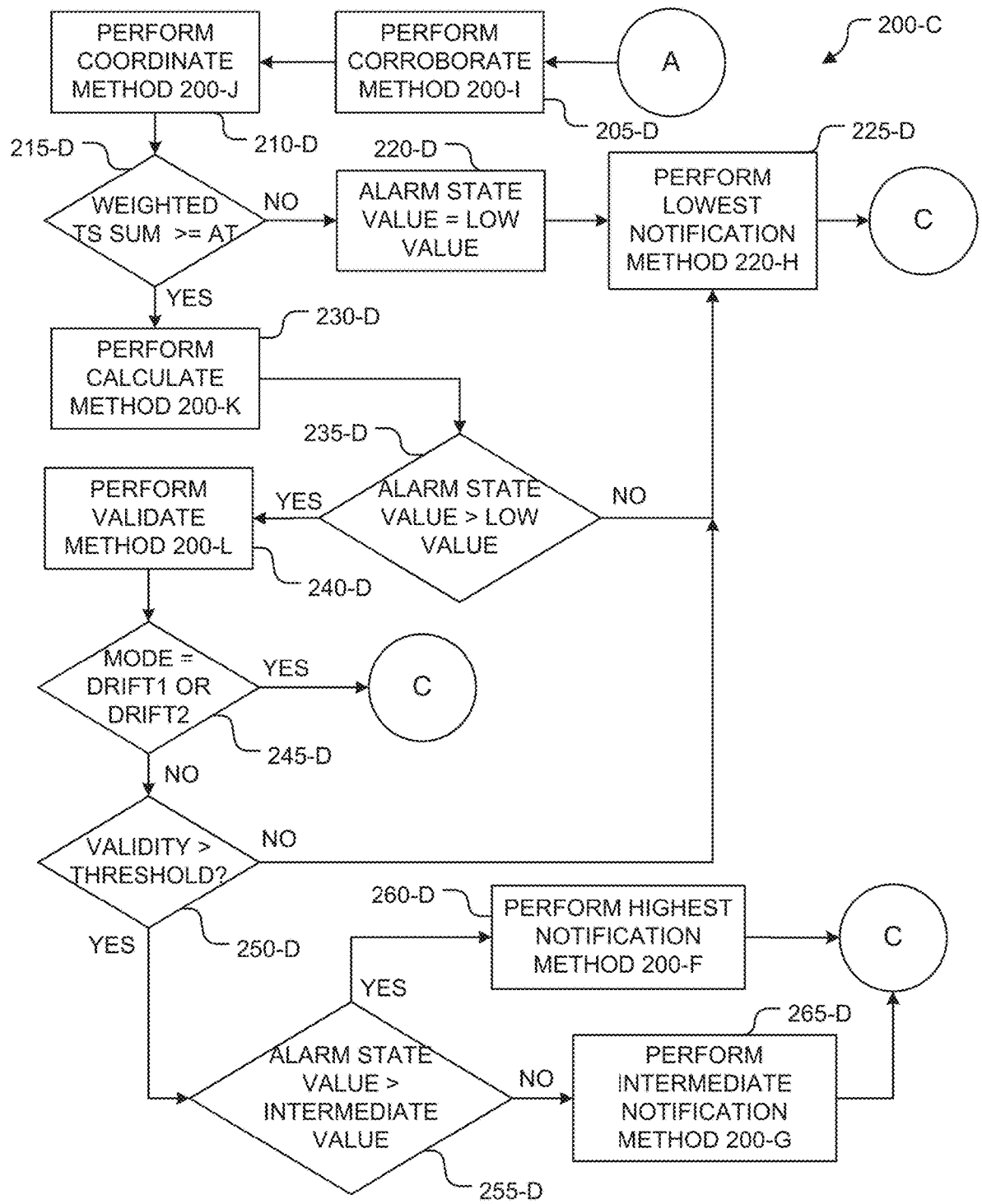
FIG. 7D is a second portion of the flow diagram of the evaluate method.
Figure 7E:
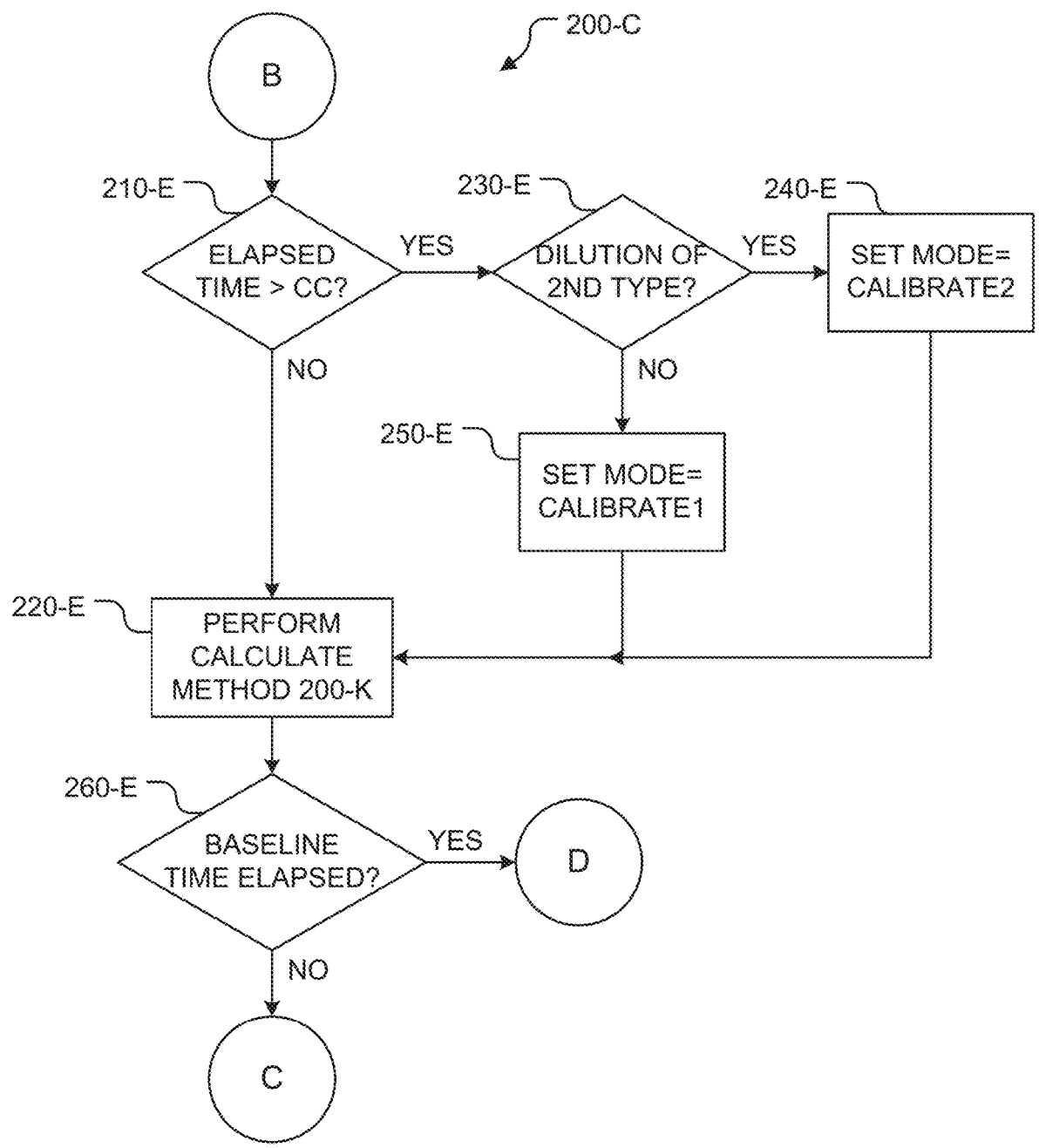
FIG. 7E is a third portion of the flow diagram of the evaluate method.

In block 250-A, the System Controller 190 performs the evaluate method 200-C (see FIGS. 7C-7E).

Then, the method 200-A terminates.

FIG. 7B is a flow diagram of the method 200-B performed by the monitor 126. For ease of illustration, the fire detection sensor(s) 216 will be described as including only the sensor 128A (see FIG. 3). Thus, the method 200-B will be described as being performed with respect to only the sensor 128A (see FIG. 3). However, the fire detection sensor(s) 216 may include any number of sensors and the method 200-B may be performed with respect to any number of sensors.

In first block 205-B, the monitor 126 polls the sensor 128A (see FIG. 3) for a sensor value C' and adds the sensor value C' to a collection of sensor values collected from the sensor 128A. By way of a non-limiting example, the monitor 126 may poll the sensor 128A for a new sensor value C' periodically with a frequency of about 1 Hz.

Then, in decision block 210-B, the monitor 126 determines whether the current $mode_t$ is equal to INITIALIZE.

When the current $mode_t$ is equal to INITIALIZE, in block 215-B, the monitor 126 sets a corrected value C equal to the sensor value C' collected in block 205-B and adds the corrected value C to a collection of corrected sensor values for the sensor 128A (see FIG. 3).

When the current $mode_t$ is not equal to INITIALIZE, in block 220-B, the monitor 126 corrects the sensor value C' for drift to obtain the corrected value C and adds the corrected value C to the collection of corrected sensor values for the sensor 128A (see FIG. 3). The corrected value C may be calculated as a function of time, temperature, and the sensor value C'.

Next, in block 225-B, the monitor 126 calculates statistics in real time for the collection of corrected sensor values accumulated for the sensor 128A (see FIG. 3). The statistics may include a mean, a standard deviation, and a linear least squares slope and intercept.

In block 230-B, the monitor 126 determines an integral value for the collection of corrected sensor values accumulated for the sensor 128A (see FIG. 3). The data may be numerically integrated in real time as the summation of each trapezoidal area above and/or below a baseline value (e.g., integral value=$\Sigma\frac{1}{2}(C_t-C_{t-1})\cdot\Delta t$).

In decision block 235-B, the monitor 126 determines whether the current $mode_t$ is equal to ROUTINE or TRIPPED.

When the current $mode_t$ is not equal to either ROUTINE or TRIPPED, the monitor 126 advances to decision block 240-B.

On the other hand, when the current $mode_t$ is equal to ROUTINE or TRIPPED, in block 245-B, the monitor 126 sets the Trigger Condition ("TC") for the sensor 128A (see FIG. 3). The monitor 126 may set the TC to the triggered value (e.g., one) when the corrected value C has exceeded a threshold value. The threshold value may be a proportional threshold, a derivative threshold, or an integral threshold. The monitor 126 may set the TC to the not triggered value (e.g., zero) when the corrected value C has not exceeded the threshold value.

The corrected value C is an instantaneous concentration of a single analyte, $\Sigma C$ is the instantaneous concentration of a group of analytes, and t is time. As mentioned above, $C_0$ is the baseline of the sensor 128A (see FIG. 3). In block 245-B, the monitor 126 may determine the corrected value C has exceeded the threshold value when a proportional measurement estimate ($C/C_0$ or $\Sigma C/C_0$), its integral ($\int C \Delta t$ or $\int \Sigma C \Delta t$, respectively), or its derivative ($\Delta C/\Delta t$ or $\Delta \Sigma C/\Delta t$, respectively), or any combination thereof (a) falls outside of one of upper and lower confidence bounds UB and LB (see FIG. 8B) and lies toward a more dangerous condition, or (b) passes an absolute boundary (e.g., exceeds a particular threshold value).

At block 245-B, the monitor 126 may determine the upper and lower confidence bounds UB and LB (see FIG. 8B) for each of the fire detection sensor(s) 216 (e.g., the sensor 128A illustrated in FIG. 3). As one of ordinary skill in the art will recognize, there is no mathematical distinction between removing sensor drift and accommodating sensor drift and the subsequent examples may use either formulation to mean the same thing. To illustrate the foregoing, consider a first sensor that is reading a true concentration value of 300 ppm and a newly calibrated second sensor that also reads about 300 ppm. After some time, the second sensor is reading 310 ppm, while the actual concentration remains at 300 ppm. In other words, the output of the second sensor has drifted by +10 ppm. The +10 ppm drift can be either be removed or accommodated. If removal is chosen, the reading is adjusted downward by 10 ppm. On the other hand, if accommodation is chosen, the new calibration level is simply set to 310 ppm.

In block 245-B, the System Controller 190 may address drift by applying a variant of the "Random Walk" model to the sensor's historical data. Using this approach, a difference between any data point and its prior value (called the series "first difference") is calculated, transformed, and modeled to determine the upper and lower confidence bounds UB and LB (see FIG. 8B) for the change in any two sequential measurements.

Figure 8A:
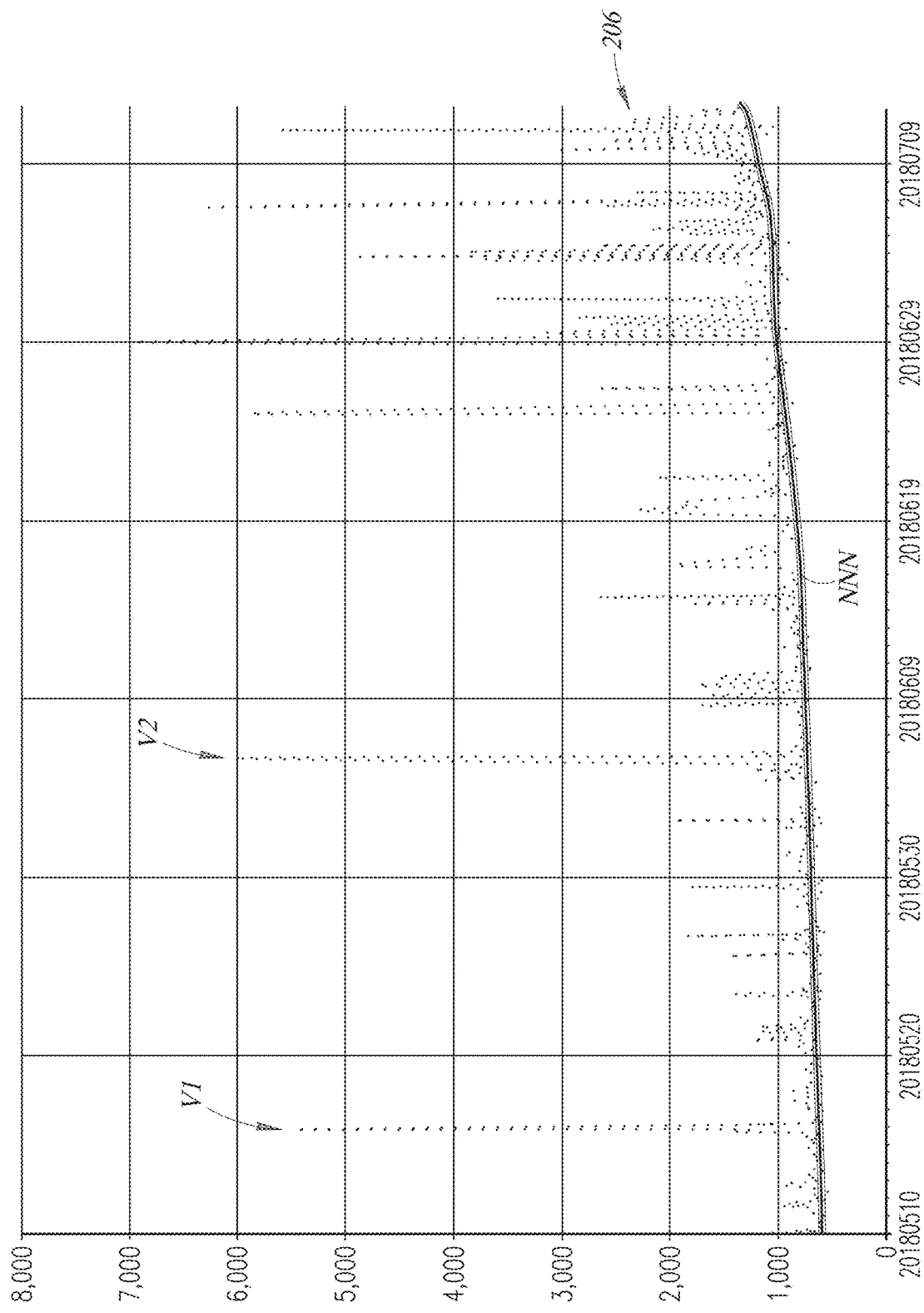
FIG. 8A is a graph of exemplary sensor readings and a line illustrating sensor drift.
Figure 8B:
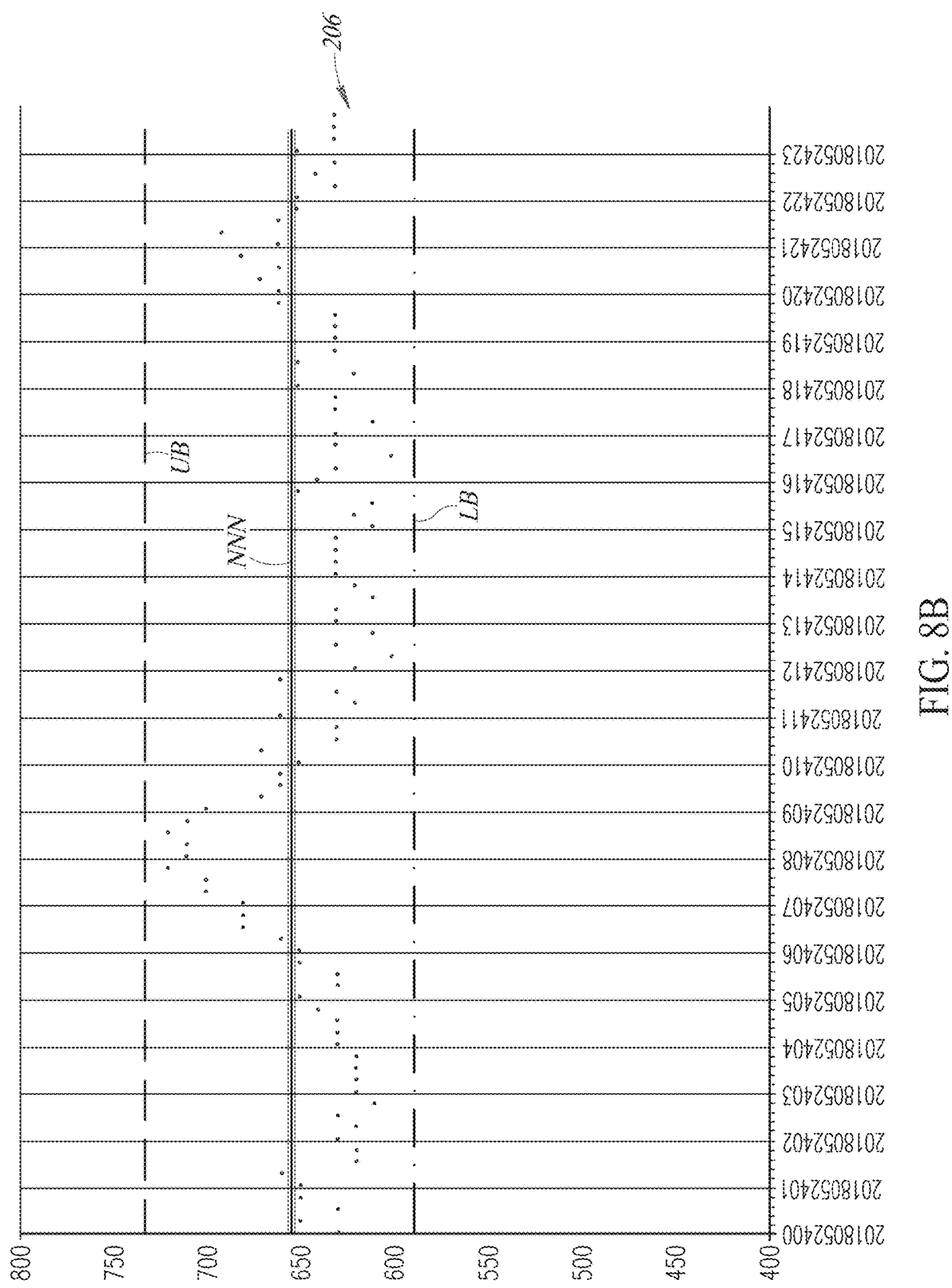
FIG. 8B is a graph of a portion of the exemplary sensor readings of FIG. 8A including the line illustrating the sensor drift and lines illustrating upper and lower confidence bounds.

In addition, the upper and lower confidence bounds UB and LB (see FIG. 8B) for cumulative changes of subsequent measurements over time, and absolute values (actual sensor readings) are also developed (as illustrated in FIG. 8B). The upper and lower confidence bounds UB and LB are based on different confidence levels, and the latter is varied depending on the reliability of the sensor. The upper and lower confidence bounds UB and LB are updated periodically by including new data.

In decision block 250-B, the monitor 126 determines whether the TC of the sensor 128A (see FIG. 3) is set to the not triggered value (e.g., zero).

When the Trigger Condition is set to other than the not triggered value (e.g., zero), in block 255-B, the monitor 126 sets the trip state ("TS") of the sensor 128A (see FIG. 3). For example, if the TS of the sensor 128A is the not tripped value (e.g., zero), the monitor 126 may increase (or increment) that TS to the single trip value (e.g., one). Similarly, if the TS of the sensor 128A is set to the single trip value (e.g., one), the monitor 126 may set the TS equal to the consecutively tripped value (e.g., two), which is the highest possible TS for a single sensor. The monitor 126 may also set the report time associated with the sensor 128A equal to the non-routine value (e.g., 30 seconds).

In decision block 260-B, the monitor 126 determines whether the current $mode_t$ is equal to ROUTINE. When the current $mode_t$ is equal to ROUTINE, in block 265-B, the monitor 126 sets the current $mode_t$ to TRIPPED. On the other hand, when the current $mode_t$ is not equal to ROUTINE, the monitor 126 advances to decision block 240-B.

In decision block 240-B, the monitor 126 determines whether the report time has elapsed. When the report time has not elapsed, the monitor 126 advances to block 270-B. On the other hand, when the report time has elapsed, in block 275-B, the monitor 126 uploads the collection of corrected sensor values, the collection of sensor values, and the TS for the sensor 128A (see FIG. 3) to the System Controller 190. Then, the monitor 126 advances to block 270-B.

In block 270-B, the monitor 126 checks (e.g., a download buffer) for new flag values and sensor parameters received from the System Controller 190. If new values are available, the monitor 126 stores them in the memory 130M. The monitor 126 may over-write its previous values with the new values. Then, the monitor 126 returns to block 205-B to continue the polling loop.

When the monitor 126 determines in decision block 250-B that the Trigger Condition is set to the not triggered value (e.g., zero), the monitor 126 advances to decision block 280-B. In decision block 280-B, the monitor 126 determines whether the current $mode_t$ is equal to TRIPPED.

When the current $mode_t$ is not equal to TRIPPED, the monitor 126 advances to decision block 240-B.

When the current $mode_t$ is equal to TRIPPED, in block 285-B, the monitor 126 sets the current $mode_t$ equal to ROUTINE and sets the report time equal to the routine value (e.g., 15 minutes) for the sensor 128A (see FIG. 3). Then, the monitor 126 advances to decision block 240-B.

Thus, the monitor 126 may use the method 200-B to supply, to the System Controller 190, the collection of corrected sensor values, the collection of sensor values, and the TS for each of the fire detection sensor(s) 216 (e.g., the sensor 128A illustrated in FIG. 3) at each expiration of the report time for the sensor. In other words, the monitor 126 may use the method 200-B to continuously supply information to the System Controller 190 collected from each of the fire detection sensor(s) 216 (see FIG. 3).

FIGS. 7C-7E are a flow diagram of the evaluate method 200-C performed by the System Controller 190.

Referring to FIG. 7C, in first block 205-C, the System Controller 190 receives the information uploaded by the monitor 126 in block 275-B (see FIG. 7B) in method 200-B (see FIG. 7B).

In decision block 210-C, the System Controller 190 determines whether the current mode$_t$ is equal to INITIALIZE.

When the current mode$_t$ is equal to INITIALIZE, the System Controller 190 advances to block 215-C. In block 215-C, the System Controller 190 records the information uploaded to the System Controller 190 by the monitor 126 in block 275-B (see FIG. 7B) in method 200-B (see FIG. 7B). For example, the System Controller 190 records the current mode$_t$, the fan speed, and the report time. Then, in block 273, the System Controller 190 may communicate (e.g., push) to the monitor 126 any operational flag changes including the current mode$_t$, the previous mode$_{t-1}$, the fan speed, and the report time.

When the current mode$_t$ is not equal to INITIALIZE, the System Controller 190 advances to decision block 220-C. In decision block 220-C, the System Controller 190 determines whether the current mode$_t$ is equal to DRIFT1.

When the current mode$_t$ is equal to DRIFT1, the System Controller 190 advances to block 225-C. In block 225-C, the System Controller 190 performs a dilution one test method 200-R (see FIG. 7R). Then, the System Controller 190 advances to the block 215-C.

When the current mode$_t$ is not equal to DRIFT1, the System Controller 190 advances to decision block 230-C. In decision block 230-C, the System Controller 190 determines whether the current mode$_t$ is equal to DRIFT2.

When the current mode$_t$ is equal to DRIFT2, the System Controller 190 advances to block 235-C. In block 235-C, the System Controller 190 performs a dilution two test method 200-S (see FIG. 7S). Then, the System Controller 190 advances to the block 215-C.

When the current mode$_t$ is not equal to DRIFT2, the System Controller 190 advances to decision block 240-C. In decision block 240-C, the System Controller 190 determines whether the current mode$_t$ is equal to TRIPPED. The decision in decision block 240-C is "YES" when the current mode$_t$ is equal to TRIPPED. Otherwise, the decision in decision block 240-C is "NO."

When the decision in decision block 240-C is "YES," the System Controller 190 advances to block 205-D (see FIG. 7D). Referring to FIG. 7D, in block 205-D, the System Controller 190 performs a corroborate method 200-I (see FIG. 7I). The System Controller 190 calculates a weighted TS sum value when the System Controller 190 performs the corroborate method 200-I (see FIG. 7I). Then, in block 210-D, the System Controller 190 performs a coordinate method 200-J (see FIG. 7J). The weighted TS sum value may be modified (e.g., increased) when the System Controller 190 performs the coordinate method 200-J (see FIG. 7J). Next, the System Controller 190 advances to decision block 215-D.

In decision block 215-D, the System Controller 190 determines whether the weighted TS sum value is greater than or equal to an alarm threshold ("AT"). By way of a non-limiting example, the AT may be 3.5. If the weighted TS sum value is greater than or equal to the AT, validation is warranted. Otherwise, validation is not warranted. The decision in decision block 215-D is "YES" when the weighted TS sum value is greater than or equal to the AT. Otherwise, the decision in decision block 215-D is "NO."

When the decision in decision block 215-D is "NO," in block 220-D, the alarm state value of the AS for the current time (t) is set to the low value (e.g., zero). The event type indicator may also be set to the no event value (e.g. to zero). Then, in block 225-D, the System Controller 190 performs a lowest notification method 200-H (see FIG. 7H). Next, the System Controller 190 advances to block 215-C.

Figure 7F:
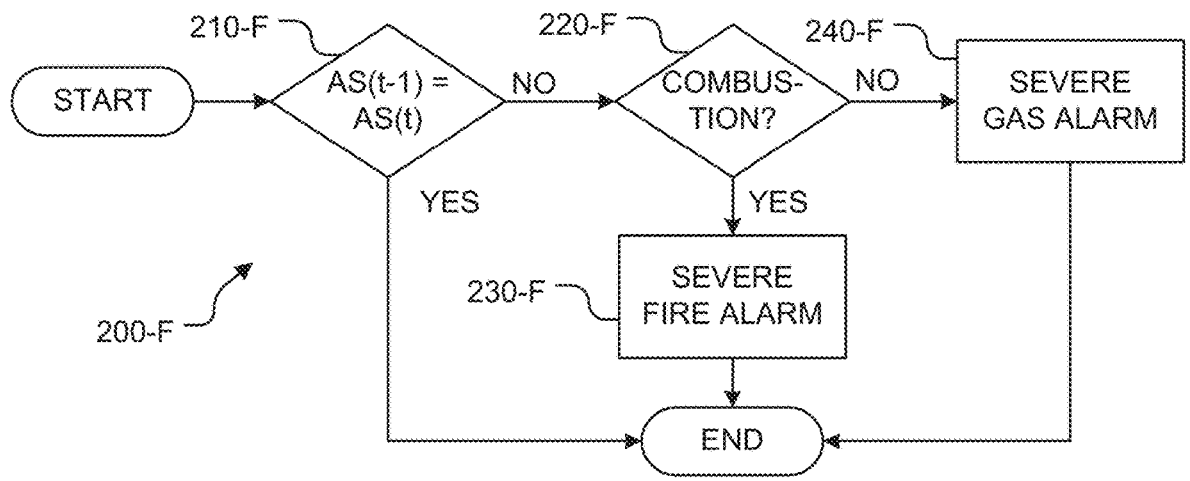
FIG. 7F is a flow diagram of a highest notification method performed by the System Controller of FIG. 1.
Figure 7G:
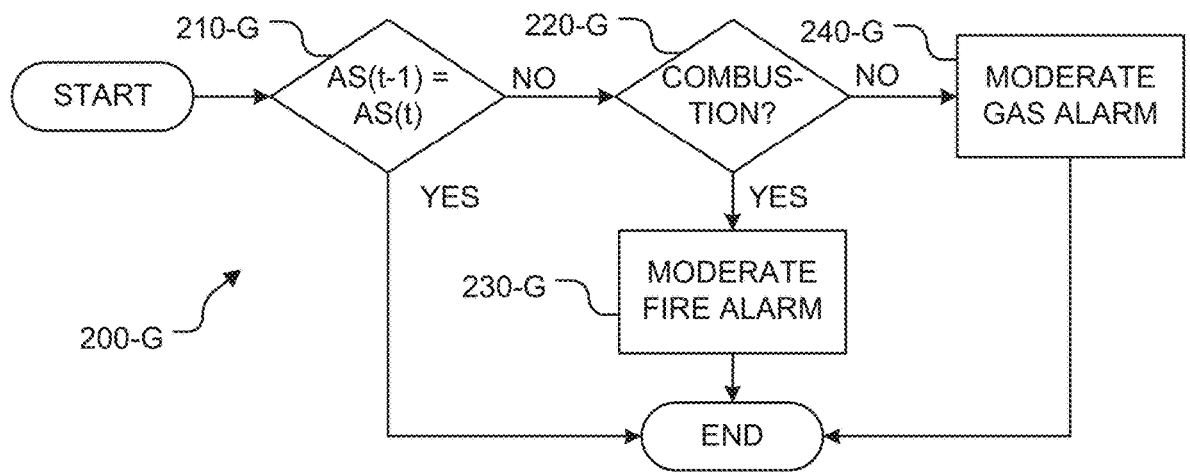
FIG. 7G is a flow diagram of an intermediate notification method performed by the System Controller of FIG. 1.
Figure 7H:
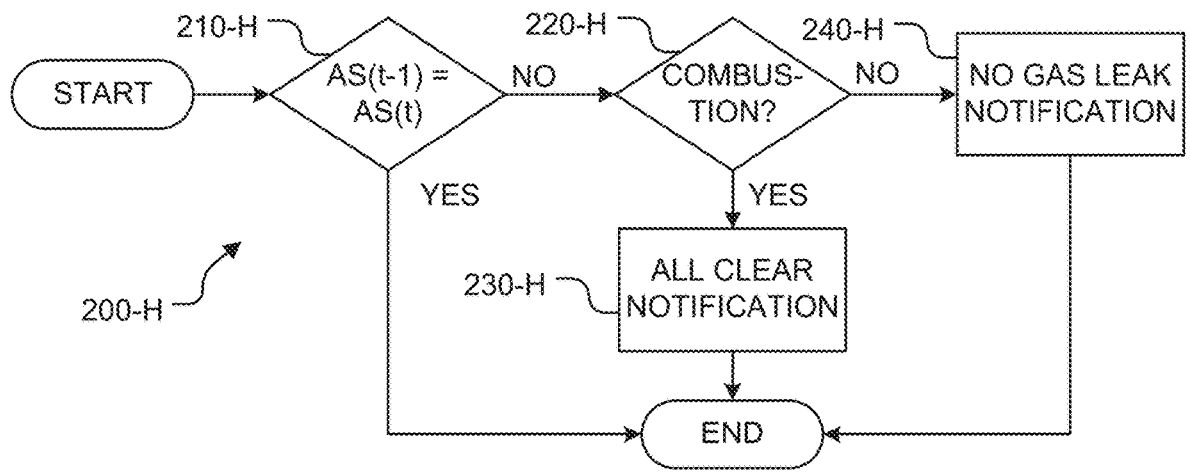
FIG. 7H is a flow diagram of a lowest notification method performed by the System Controller of FIG. 1.
Figure 7I:
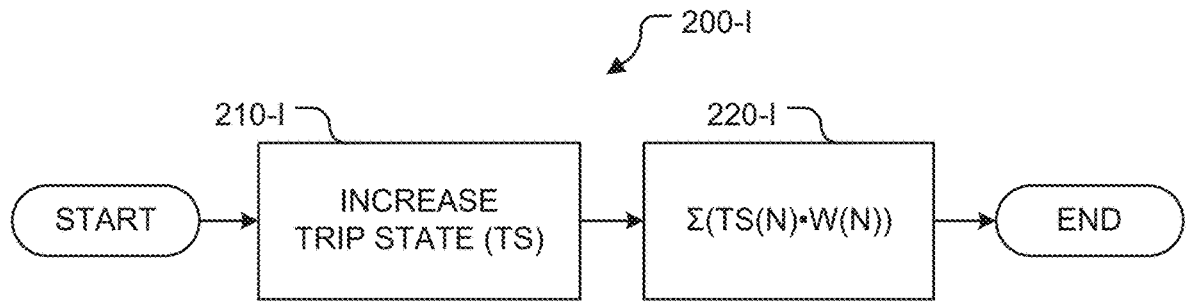
FIG. 7I is a flow diagram of a corroborate method performed by the System Controller of FIG. 1.
Figure 7J:
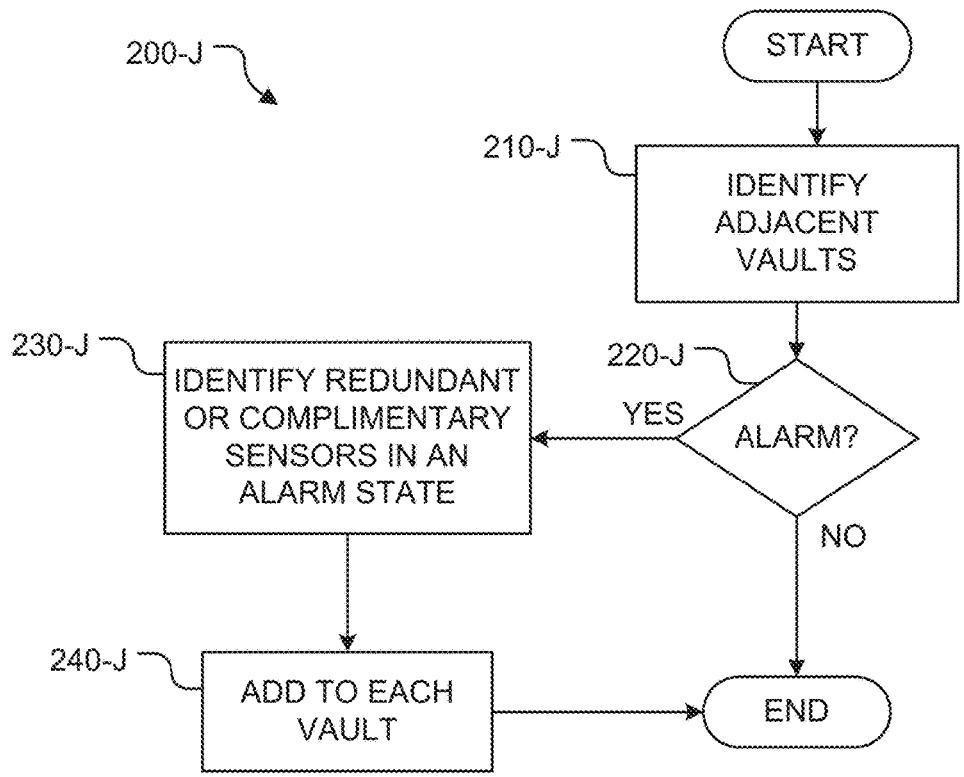
FIG. 7J is a flow diagram of a coordinate method performed by the System Controller of FIG. 1.
Figure 7K:
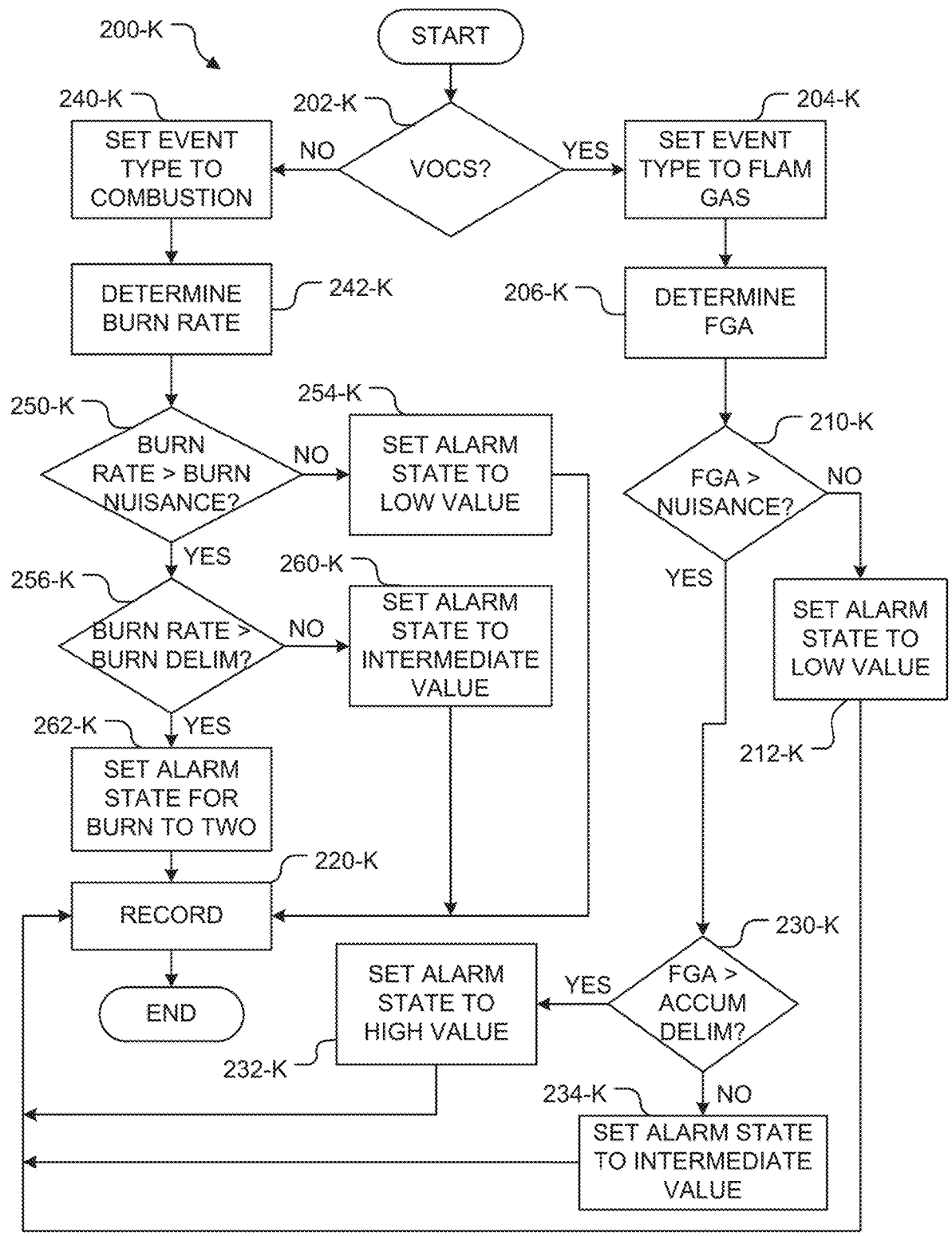
FIG. 7K is a flow diagram of a calculate method performed by the System Controller of FIG. 1.

When the decision in decision block 215-D is "YES," in block 230-D the System Controller 190 performs a calculate method 200-K (see FIG. 7K). Then, in decision block 235-D, the System Controller 190 determines whether the alarm state value of the AS for the current time (t) is greater than the low value (e.g., zero). The decision in decision block 235-D is "YES," when the alarm state value of the AS for the current time (t) is greater than the low value. Otherwise, the decision in decision block 235-D is "NO."

When the decision in decision block 235-D is "NO," in block 225-D, the System Controller 190 performs the lowest notification method 200-H (see FIG. 7H). Then, the System Controller 190 advances to block 215-C.

Figure 7L:
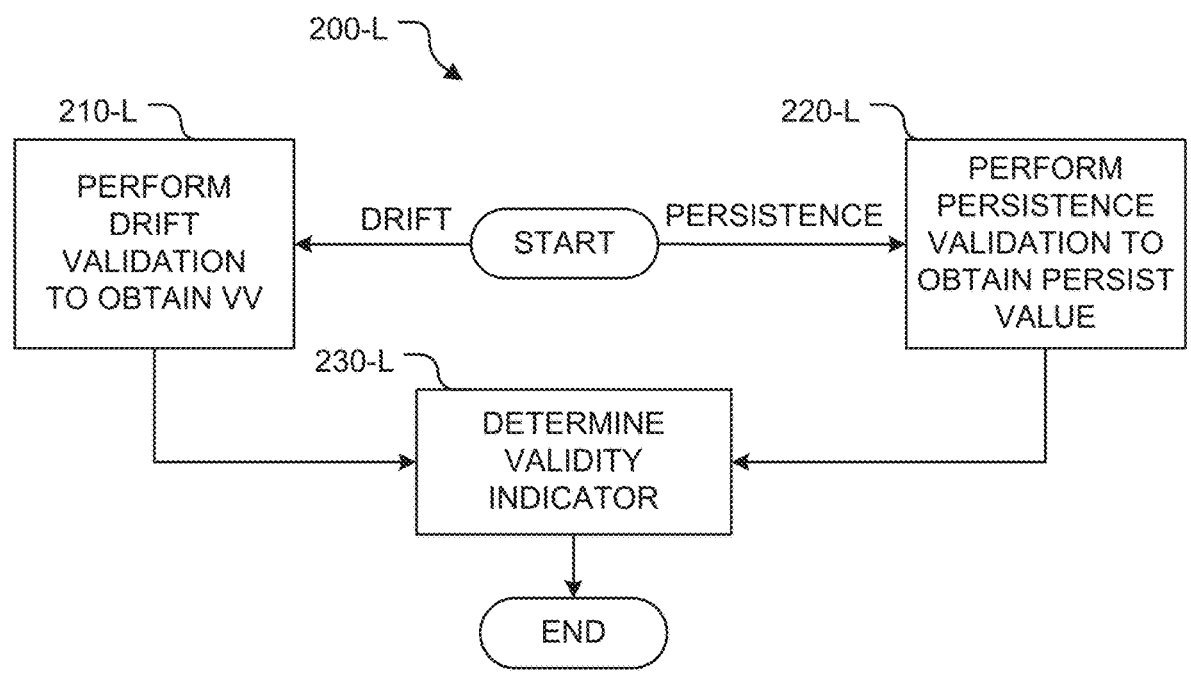
FIG. 7L is a flow diagram of a validate method performed by the System Controller of FIG. 1.

When the decision in decision block 235-D is "YES," in block 240-D, the System Controller 190 performs a validate method 200-L (see FIG. 7L). Then, the System Controller 190 advances to decision block 245-D whereat the System Controller 190 determines whether the current mode$_t$ is set to DRIFT1 or DRIFT2. The decision in decision block 245-D is "YES," when the current mode$_t$ is set to DRIFT1 or DRIFT2. Otherwise, the decision in decision block 245-D is "NO."

When the decision in decision block 245-D is "YES," the System Controller 190 advances to block 215-C.

When the decision in decision block 245-D is "NO," the System Controller 190 advances to decision block 250-D. In decision block 250-D, the System Controller 190 determines whether a validity indicator (obtained in block 240-D) is greater than a validation threshold. The decision in decision block 250-D is "YES," when the validity indicator is greater than the validation threshold. Otherwise, the decision in decision block 250-D is "NO."

When the decision in decision block 250-D is "NO," in block 225-D, the System Controller 190 performs the lowest notification method 200-H (see FIG. 7H). Then, the System Controller 190 advances to block 215-C (see FIG. 7C).

When the decision in decision block 250-D is "YES," in decision block 255-D, the System Controller 190 determines whether the alarm state value of the AS for the current time (t) is greater than the intermediate value (e.g., one). The decision in decision block 255-D is "YES," when the alarm state value of the AS for the current time (t) is greater than the intermediate value. Otherwise, the decision in decision block 255-D is "NO."

When the decision in decision block 255-D is "YES," in block 260-D, the System Controller 190 performs a highest notification method 200-F (see FIG. 7F). Then, the System Controller 190 advances to block 215-C (see FIG. 7C).

When the decision in decision block 255-D is "NO," in block 265-D, the System Controller 190 performs an intermediate notification method 200-G (see FIG. 7G). Then, the System Controller 190 advances to block 215-C (see FIG. 7C).

Referring to FIG. 7C, when the decision in decision block 240-C is "NO," the System Controller 190 advances to decision block 245-C. In decision block 245-C, the System Controller 190 determines whether the current mode$_t$ is equal to CALIBRATE1 or CALIBRATE2.

When the current mode$_t$ is equal to CALIBRATE1 or CALIBRATE2, the System Controller 190 advances to block 250-C. In block 250-C, the System Controller 190 performs a desaturate method 200-O (see FIG. 7O). Then, the System Controller 190 advances to block 255-C and performs a calibrate method 200-P (see FIG. 7P). Next, the System Controller 190 advances to block 260-C and performs a relate method 200-Q (see FIG. 7Q). Then, the System Controller 190 advances to block 215-C.

Referring to FIG. 7E, when the current mode$_t$ is not equal to CALIBRATE1 or CALIBRATE2, the System Controller 190 advances to decision block 210-E. In decision block 210-E, the System Controller 190 determines whether the elapsed time exceeds a calibration cadence ("CC") value (e.g., determined by the relate method 200-Q illustrated in FIG. 7Q).

When the elapsed time does not exceed the CC value, the System Controller 190 advances to block 220-E.

When the elapsed time exceeds the CC value, in block 230-E, the System Controller 190 advances to decision block 230-E whereat the System Controller 190 determines whether dilution of the second type is available. When dilution of the second type is available, in block 240-E, the System Controller 190 sets the current mode$_t$ equal to CALIBRATE2. Otherwise, in block 250-E, the System Controller 190 sets the current mode$_t$ equal to CALIBRATE1. Then, the System Controller 190 advances to block 220-E.

In block 220-E, the System Controller 190 performs the calculate method 200-K (see FIG. 7K).

Then, in decision block 260-E, the System Controller 190 determines whether the elapsed time exceeds the baseline time for the sensor 128A (see FIG. 3). Referring to FIG. 7C, when the elapsed time exceeds the baseline time, in block 260-C, the System Controller 190 performs the relate method 200-Q (see FIG. 7Q). Then, the System Controller 190 advances to block 215-C.

Referring to FIG. 7C, when the elapsed time does not exceed the baseline time, the System Controller 190 advances to block 215-C.

FIG. 7F is a flow diagram of the highest notification method 200-F, which the System Controller 190 may perform in block 260-D (see FIG. 7D) of the evaluate method 200-C illustrated in FIGS. 7C-7E. Referring to FIG. 7F, in first decision block 210-F, the System Controller 190 determines whether the alarm state value of the AS for the current time (t) is equal to the alarm state value of the AS for the previous time (t−1). When these two alarm state values are equal, the decision in decision block 210-F is "YES." Otherwise, the decision in decision block 210-F is "NO."

When the decision in decision block 210-F is "YES," the highest notification method 200-F terminates.

When the decision in decision block 210-F is "NO," in decision block 220-F, the System Controller 190 determines whether the event type indicator of the sensor 128A (see FIG. 3) is set to the combustion value. The decision in decision block 220-F is "YES" when the event type indicator of the sensor 128A is set to the combustion value. Otherwise, the decision in decision block 220-F is "NO."

When the decision in decision block 220-F is "YES," in block 230-F, the System Controller 190 sends a severe fire alarm notification to one or more users. Then, the highest notification method 200-F terminates.

When the decision in decision block 220-F is "NO," in block 240-F, the System Controller 190 sends a severe gas alarm notification to the one or more users. Then, the highest notification method 200-F terminates.

FIG. 7G is a flow diagram of the intermediate notification method 200-G, which the System Controller 190 may perform in block 265-D (see FIG. 7D) of the evaluate method 200-C illustrated in FIGS. 7C-7E. Referring to FIG. 7G, in first decision block 210-G, the System Controller 190 determines whether the alarm state value of the AS for the current time (t) is equal to the alarm state value of the AS for the previous time (t−1). When these two alarm state values are equal, the decision in decision block 210-G is "YES." Otherwise, the decision in decision block 210-G is "NO."

When the decision in decision block 210-G is "YES," the intermediate notification method 200-G terminates.

When the decision in decision block 210-G is "NO," in decision block 220-G, the System Controller 190 determines whether the event type indicator of the sensor 128A (see FIG. 3) is set to the combustion value. The decision in decision block 220-G is "YES" when the event type indicator of the sensor 128A is set to the combustion value. Otherwise, the decision in decision block 220-G is "NO."

When the decision in decision block 220-G is "YES," in block 230-G, the System Controller 190 sends a moderate fire alarm notification to the one or more users. Then, the intermediate notification method 200-G terminates.

When the decision in decision block 220-G is "NO," in block 240-G, the System Controller 190 sends a moderate gas alarm notification to the one or more users. Then, the intermediate notification method 200-G terminates.

FIG. 7H is a flow diagram of the lowest notification method 200-H, which the System Controller 190 may perform in block 225-D (see FIG. 7D) of the evaluate method 200-C illustrated in FIGS. 7C-7E. Referring to FIG. 7H, in first decision block 210-H, the System Controller 190 determines whether the alarm state value of the AS for the current time (t) is equal to the alarm state value of the AS for the previous time (t−1). When these two alarm state values are equal, the decision in decision block 210-H is "YES." Otherwise, the decision in decision block 210-H is "NO."

When the decision in decision block 210-H is "YES," the lowest notification method 200-H terminates.

When the decision in decision block 210-H is "NO," in decision block 220-H, the System Controller 190 determines whether the event type indicator of the sensor 128A (see FIG. 3) is set to the combustion value. The decision in decision block 220-H is "YES" when the event type indicator of the sensor 128A is set to the combustion value. Otherwise, the decision in decision block 220-H is "NO."

When the decision in decision block 220-H is "YES," in block 230-H, the System Controller 190 sends an all clear notification to the one or more users. Then, the lowest notification method 200-H terminates.

When the decision in decision block 220-H is "NO," in block 240-H, the System Controller 190 sends a no gas leak notification to the one or more users. Then, the lowest notification method 200-H terminates.

FIG. 7I is a flow diagram of the corroborate method 200-I, which the System Controller 190 may perform in block 205-D (see FIG. 7D) of the method 200-C (see FIGS. 7C-7E).

In first block 210-I, the System Controller 190 increases the trip state (TS) for the sensor 128A (see FIG. 3). For example, the TS may be increased by one for each sequential alarm condition. As mentioned above, the TS is capped at the consecutively tripped value (e.g., two).

Then, in block 220-I, the System Controller 190 determines the weighted TS sum value for the sensor 128A (see FIG. 3). The System Controller 190 may calculate the weighted TS sum value by totaling the product of the individual TS value and its associated weight for each of the fire detection sensor(s) 216 (e.g., weighted TS sum value=>

(TS(N)·W(N))). The weight(s) may be determined in block 245-Q (see FIG. 7Q) of the relate method 200-Q (see FIG. 7Q).

Then, the corroborate method 200-I terminates.

FIG. 7J is a flow diagram of the coordinate method 200-J, which the System Controller 190 may perform in block 210-D (see FIG. 7D) of the method 200-C (see FIGS. 7C-7E).

In first block 210-J, the System Controller 190 identifies adjacent vaults (e.g., using a user-defined radius and the geo-coordinates of all of the vaults).

Then, in decision block 220-J, the System Controller 190 determines whether any of the adjacent vaults are in an alarm condition. The decision in decision block 220-J is "YES," when at least some of the adjacent vaults are in an alarm condition. Otherwise, the decision in decision block 220-J is "NO" and the coordinate method 200-J terminates.

When the decision in decision block 220-J is "YES," in block 230-J, the System Controller 190 identifies any redundant or complimentary sensors in an alarm state that are within the adjacent vaults in an alarm condition. Such sensors are reading corroborating perturbations.

Then, in block 240-J, the System Controller 190 adds the TS of the sensors identified in block 230-J to the weighted TS sum value of each of the vaults identified in block 210-J and to the weighted TS sum of the vault 112. Then, the coordinate method 200-J terminates.

FIG. 7K is a flow diagram of the calculate method 200-K, which the System Controller 190 may perform in blocks 230-D (see FIG. 7D) and 220-E (see FIG. 7E) of the evaluate method 200-C (see FIGS. 7C-7E).

The System Controller 190 performs the calculate method 200-K to determine the event type indicator for the sensor 128A (see FIG. 3) at the current time (t) and delineate between small and large events. The System Controller 190 may use either a component mass balance or a delineation method and concentration thresholds to estimate event magnitude. The concentration thresholds may include the following values:
1. A burn nuisance threshold (e.g., 0.1 g/s for the component mass balance and 1000 ppm for the delineation method),
2. A burn level delimiter (e.g., 1.0 g/s the component mass balance and 2000 ppm for the delineation method),
3. A FGA nuisance threshold (e.g., 0.1 g/s the component mass balance and 2000 ppm for the delineation method), and
4. A FGA level delimiter (e.g., 1.0 g/s the component mass balance and 4000 ppm for the delineation method).

The concentration thresholds may be preset default values, user specified values, or values set by an artificial intelligence algorithm. The concentration thresholds may be specified for all of the vaults or different values may be specified for at least some of the vaults.

In decision block 202-K, the System Controller 190 determines whether VOCs are present inside the vault 112. For example, the decision in decision block 202-K may be "YES" when the System Controller 190 determines VOCs are present, but fire by-products, such as CO, $CO_2$, NO, $NO_2$, and $O_3$, are at non-fire levels. The System Controller 190 may determine that VOCs are present when the concentration of VOCs is greater than 2000 ppm. The System Controller 190 may determine that CO, $CO_2$, NO, $NO_2$, and $O_3$ are at non-fire levels when their concentrations total less than 1000 ppm.

When the decision in decision block 202-K is "YES," in block 204-K, the System Controller 190 sets the event type indicator for the current time (t) and the sensor 128A (see FIG. 3) to the FGA value (e.g., two).

Then, in block 206-K, the System Controller 190 determines a flammable gas accumulation ("FGA"). Flammable gas accumulation is a rate at which the flammable gas(es) (e.g., VOCs and $H_2S$) are being introduced into the vault 112. The System Controller 190 may perform either a component mass balance or a delineation method to determine the FGA. The component mass balance, energy balance, and water balance are described below. The delineation method may include calculating the FGA using the following Equation 6:

$$FGA = C_{CO} + CH_2 + C_{VOC} \tag{6}$$

Next, in decision block 210-K, the System Controller 190 decides whether the FGA is greater than the FGA nuisance threshold. The decision in decision block 210-K is "YES" when the FGA is greater than the FGA nuisance threshold. Otherwise, the decision in decision block 210-K is "NO."

When the decision in decision block 210-K is "NO," in block 212-K, the System Controller 190 sets the alarm state value to the low value (e.g., zero). Then, the System Controller 190 advances to block 220-K.

When the decision in decision block 210-K is "YES," in block 230-K, the System Controller 190 decides whether the FGA is greater than the FGA level delimiter. The decision in decision block 230-K is "YES" when the FGA is greater than the FGA level delimiter. Otherwise, the decision in decision block 230-K is "NO."

When the decision in decision block 230-K is "YES," in block 232-K, the System Controller 190 sets the alarm state value equal to the high value (e.g., two). Then, the System Controller 190 advances to block 220-K.

When the decision in decision block 230-K is "NO," in block 234-K, the System Controller 190 sets the alarm state value equal to the intermediate value (e.g., one). Then, the System Controller 190 advances to block 220-K.

In block 220-K, the System Controller 190 stores the alarm state value, the burn rate, and the FGA.

Then, the calculate method 200-K terminates.

When the decision in decision block 202-K is "NO," in block 240-K, the System Controller 190 sets the event type to the combustion value (e.g., one).

Then, in block 242-K, the System Controller 190 determines the burn rate. In block 242-K, the System Controller 190 may perform either the component mass balance (described below) or the delineation method to determine the burn rate. When a component mass balance is used, the burn rate may be expressed as a unit mass consumed per unit time. The delineation method may include calculating the burn rate using the following Equation 7:

$$\text{Burn Rate} = C_{CO} + C_{CO_2} + C_{NO} + C_{NO_2} + CO_3 + \max(0, 1000^*(20.95\% - C_{O_2}\%)) \tag{7}$$

When Equation 7 is used, the burn rate may be expressed in ppm.

Next, in decision block 250-K, the System Controller 190 decides whether the burn rate is greater than the burn nuisance threshold. The decision in decision block 250-K is "YES" when the burn rate is greater than the burn nuisance threshold. Otherwise, the decision in decision block 250-K is "NO."

When the decision in decision block 250-K is "NO," in block 254-K, the System Controller 190 sets the alarm state value for the current time (t) and the sensor 128A (see FIG. 3) to the low value (e.g., zero). Then, the System Controller 190 advances to block 220-K.

When the decision in decision block 250-K is "YES," in decision block 256-K, the System Controller 190 decides whether the burn rate is greater than the burn level delimiter. The decision in decision block 256-K is "YES" when the burn rate is greater than the burn level delimiter. Otherwise, the decision in decision block 256-K is "NO."

When the decision in decision block 256-K is "NO," in block 260-K, the System Controller 190 sets the alarm state value for the current time (t) and the sensor 128A (see FIG. 3) to the intermediate value (e.g., one). Then, the System Controller 190 advances to block 220-K.

When the decision in decision block 256-K is "YES," in block 262-K, the System Controller 190 sets the alarm state value for the current time (t) and the sensor 128A (see FIG. 3) to the high value (e.g., two). Then, the System Controller 190 advances to block 220-K.

Then, the calculate method 200-K terminates.

FIG. 7L is a flow diagram of the validate method 200-L, which the System Controller 190 may perform in block 240-D (see FIG. 7D) of the evaluate method 200-C (see FIGS. 7C-7E). The validate method 200-L may include two parallel validation processes, labeled "DRIFT" and "PERSISTENCE" in FIG. 7L. The first ("DRIFT") validation process confirms that drift has not caused those sensor readings in alarm condition to be in that condition. The second ("PERSISTENCE") validation process confirms that the alarm condition meets user-defined persistence. As a non-limiting example of persistence, imagine that a truck stops directly over the fresh air inlet of a manhole cover and spews combustion products into the manhole. If that situation persists for only the length of time of a single stop light cycle, an alarm would be a false positive alarm.

In block 210-L, the System Controller 190 performs a drift validation process 200-M (see FIG. 7M) and obtains a validity value ("VV").

In block 220-L, the System Controller 190 performs a persistence validation process 200-N (see FIG. 7N) and obtains a persistence value.

In block 230-L, the System Controller 190 totals the persistence value and the VV to obtain a validity indicator. Then, the validate method 200-L terminates.

Figure 7M:
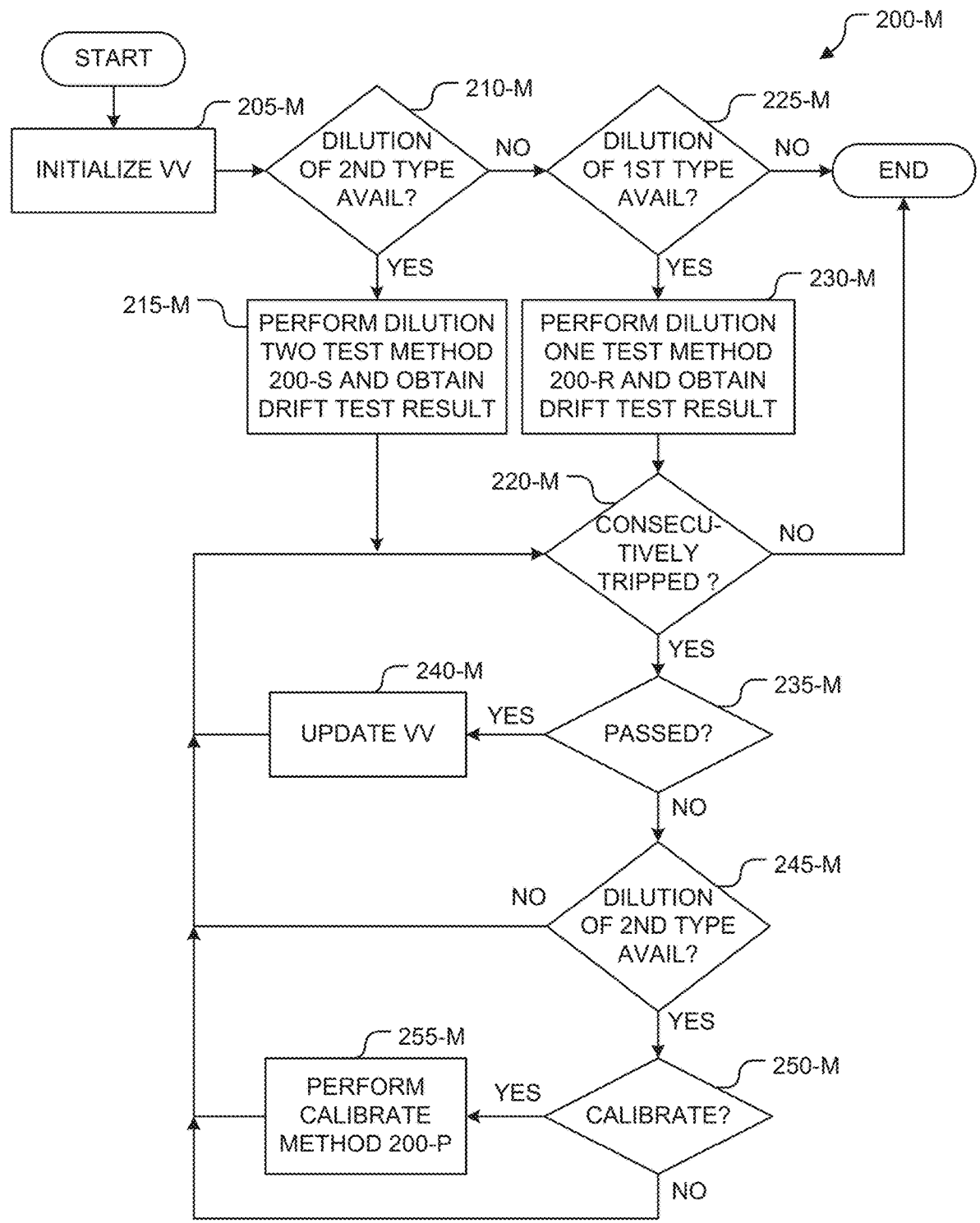
FIG. 7M is a flow diagram of a drift validation process performed by the System Controller of FIG. 1.

FIG. 7M is a flow diagram of the drift validation process 200-M, which the System Controller 190 may perform in block 210-L (see FIG. 7L) of the validate method 200-L (see FIG. 7L).

In first block 205-M, the System Controller 190 initializes the VV. For example, in block 205-M, the System Controller 190 may set the VV equal to zero.

In decision block 210-M, the System Controller 190 determines whether dilution of the second type is available. The decision in decision block 210-M is "YES" when dilution of the second type is available. Otherwise, the decision in decision block 210-M is "NO."

When the decision in decision block 210-M is "YES," in block 215-M, the System Controller 190 performs the dilution two test method 200-S (see FIG. 7S) and obtains the drift test result. Then, the System Controller 190 advances to decision block 220-M.

When the decision in decision block 210-M is "NO," in decision block 225-M, the System Controller 190 determines whether dilution of the first type is available. The decision in decision block 225-M is "YES" when dilution of the first type is available. Otherwise, the decision in decision block 225-M is "NO."

When the decision in decision block 225-M is "NO," the drift validation process 200-M terminates.

When the decision in decision block 225-M is "YES," in block 230-M, the System Controller 190 performs the dilution one test method 200-R (see FIG. 7R) and obtains the drift test result. Then, the System Controller 190 advances to decision block 220-M.

In decision block 220-M, the System Controller 190 determines whether the TS of the sensor 128A (see FIG. 3) is set to the consecutively tripped value (e.g., two). The decision in decision block 220-M is "YES" when the TS of the sensor 128A is set to the consecutively tripped value. Otherwise, the decision in decision block 220-M is "NO."

When the decision in decision block 220-M is "NO," the drift validation process 200-M terminates.

When the decision in decision block 220-M is "YES," in decision block 235-M, the System Controller 190 determines whether the drift test result indicates that the sensor 128A (see FIG. 3) has passed. The decision in decision block 235-M is "YES" when the drift test result indicates that the sensor 128A has passed. Otherwise, the decision in decision block 235-M is "NO."

When the decision in decision block 235-M is "YES," in block 240-M, the System Controller 190 updates the VV. For example, the System Controller 190 may add one to the VV. By way of another non-limiting example, the drift test result may be a first value (e.g., one) when the sensor 128A (see FIG. 3) passed and a different second value (e.g., zero) when the sensor 128A failed. In such embodiments, the drift test result may be added to the VV. Then, the System Controller 190 returns to decision block 220-M.

When the decision in decision block 235-M is "NO," in decision block 245-M the System Controller 190 determines whether dilution of the second type is available. The decision in decision block 245-M is "YES" when dilution of the second type is available. Otherwise, the decision in decision block 245-M is "NO."

When the decision in decision block 245-M is "NO," the System Controller 190 returns to decision block 220-M.

When the decision in decision block 245-M is "YES," in decision block 250-M, the System Controller 190 determines whether the sensor 128A (see FIG. 3) should be calibrated. By way of a non-limiting example, the System Controller 190 may determine it is time to calibrate the sensor 128A when at least a predetermined portion (e.g., 10%) of the calibration cadence ("CC") time has transpired since the previous calibration of the sensor 128A (see FIG. 3). The predetermined portion may be specified by a user.

When the decision in decision block 250-M is "NO," the System Controller 190 returns to decision block 220-M.

Figure 7N:
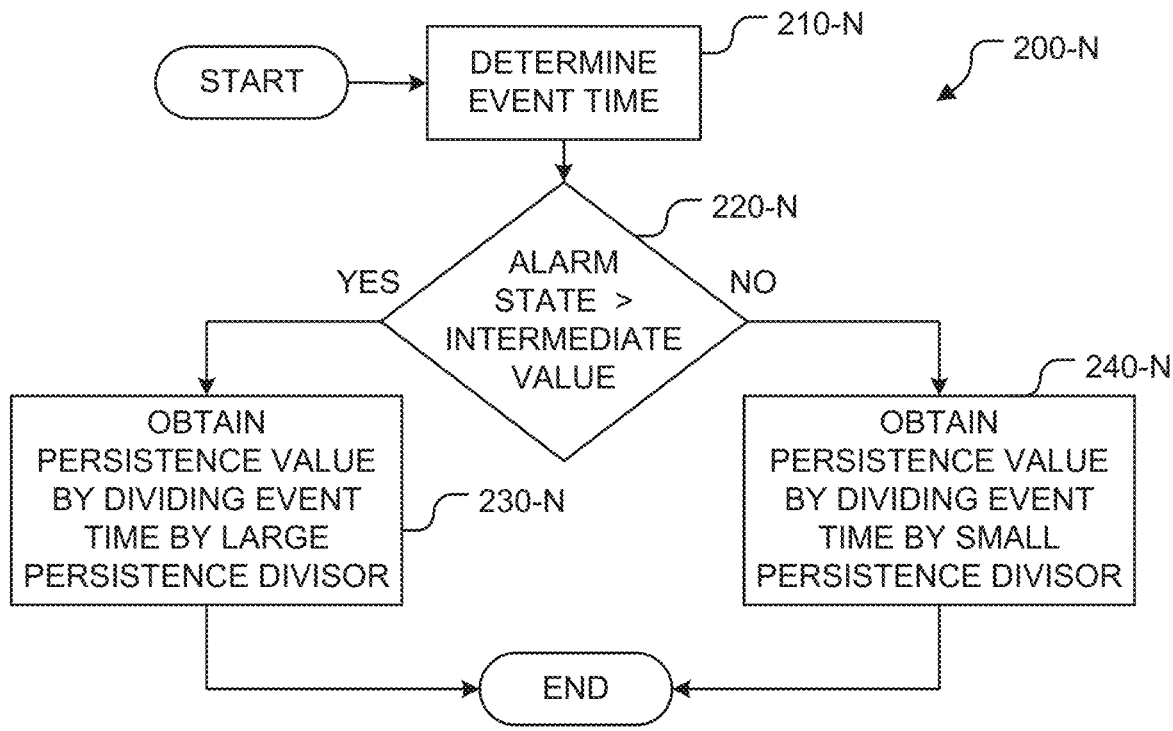
FIG. 7N is a flow diagram of a persistence validation process performed by the System Controller of FIG. 1.
Figure 7O:
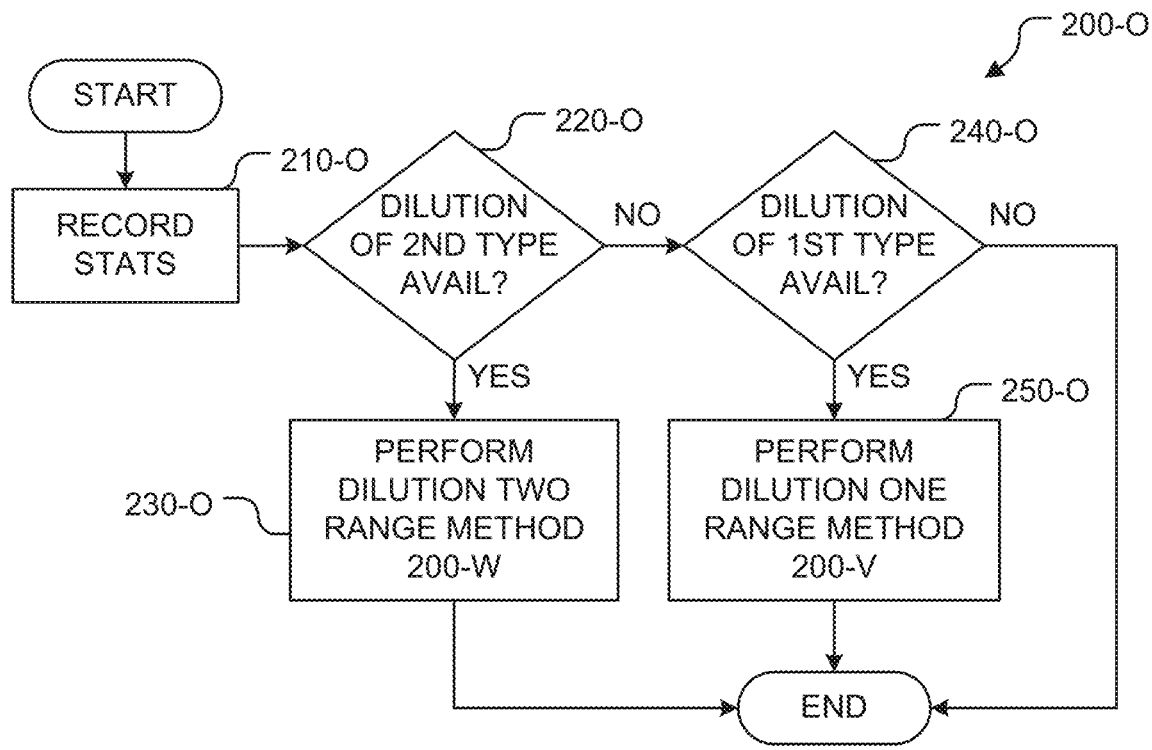
FIG. 7O is a flow diagram of a desaturate method performed by the System Controller of FIG. 1.
Figure 7P:
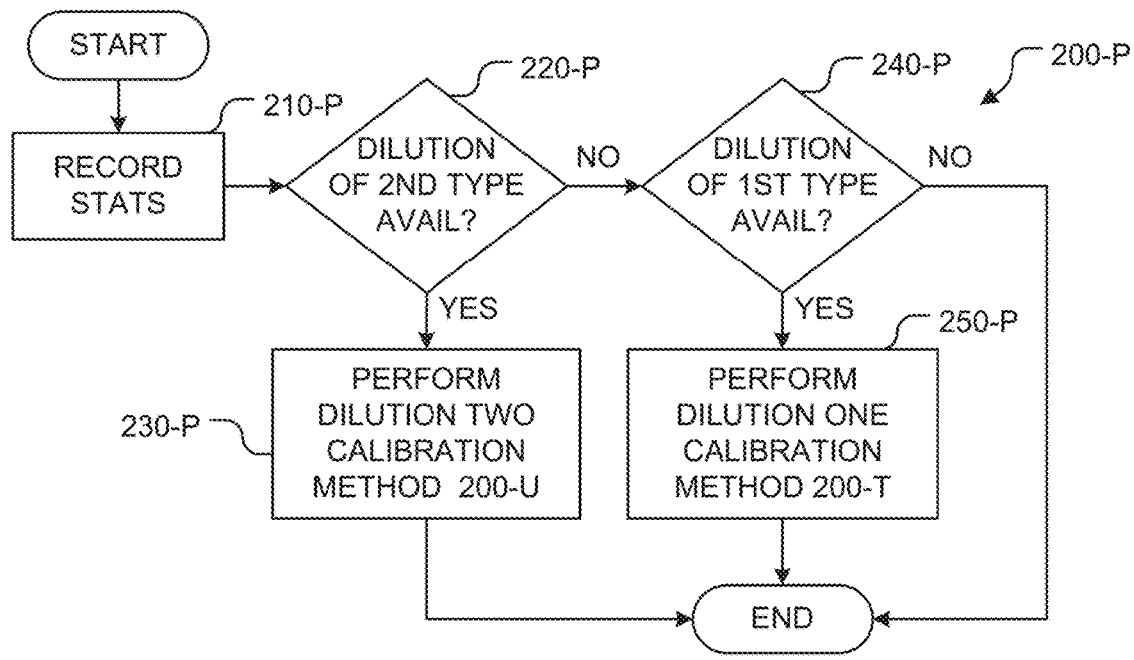
FIG. 7P is a flow diagram of a calibrate method performed by the System Controller of FIG. 1.

When the decision in decision block 250-M is "YES," in block 255-M, the System Controller 190 performs the calibrate method 200-P (see FIG. 7P). Then, the System Controller 190 returns to decision block 220-M.

FIG. 7N is a flow diagram of the persistence validation process 200-N, which the System Controller 190 may perform in block 220-L (see FIG. 7L) of the validate method 200-L (see FIG. 7L).

In first block 210-N, the System Controller 190 determines the event time for the sensor 128A (see FIG. 3). By way of a non-limiting example, the event time may be the sample time minus the event start time. The event start time is the time when the first sensor tripped (e.g., when any TS(N)>0).

Then, in decision block 220-N, the System Controller 190 determines whether the alarm state value at the current time is greater than the intermediate value (e.g., one), meaning the event is large. The decision in decision block 220-N is "YES" when the event is large. Otherwise, the decision in decision block 220-N is "NO."

When the decision in decision block 220-N is "YES," in block 230-N, the System Controller 190 sets the persistence value equal to the event time (determined in block 210-N) divided by a large persistence divisor. The large persistence divisor may be user defined or calculated by the System Controller 190. The greater the persistence divisor, the greater persistence is required to trigger an alarm state. For example, if the event is large, the large persistence divisor is equal to 60 seconds, and the event time is 30 seconds, the persistence value would equal 0.5 (30/60=0.5). Then, the persistence validation process 200-N terminates.

When the decision in decision block 220-N is "NO," the event is small. In block 240-N, the System Controller 190 sets the persistence value equal to the event time (determined in block 210-N) divided by a small persistence divisor. The small persistence divisor may be user defined or calculated by the System Controller 190. For example, when the event is small, the small persistence divisor is equal to 300 seconds, and the event time is 30 seconds, the persistence value would equal 0.1 (30/300=0.1). Then, the persistence validation process 200-N terminates.

FIG. 7O is a flow diagram of the desaturate method 200-O, which the System Controller 190 may perform in block 250-C (see FIG. 7C) of the evaluate method 200-C (see FIGS. 7C-7E). For sensors that are at or near their saturation limits, the System Controller 190 may perform the desaturate method 200-O, which allows perturbations in dilution to bring the sensor back into its operational range.

In first block 210-O, the System Controller 190 may record the statistics determined in blocks 225-B and 230-B (see FIG. 7B) of the method 200-B (see FIG. 7B).

In decision block 220-O, the System Controller 190 determines whether dilution of the second type is available. The decision in decision block 220-O is "YES" when dilution of the second type is available. Otherwise, the decision in decision block 220-O is "NO."

Figure 7Q:
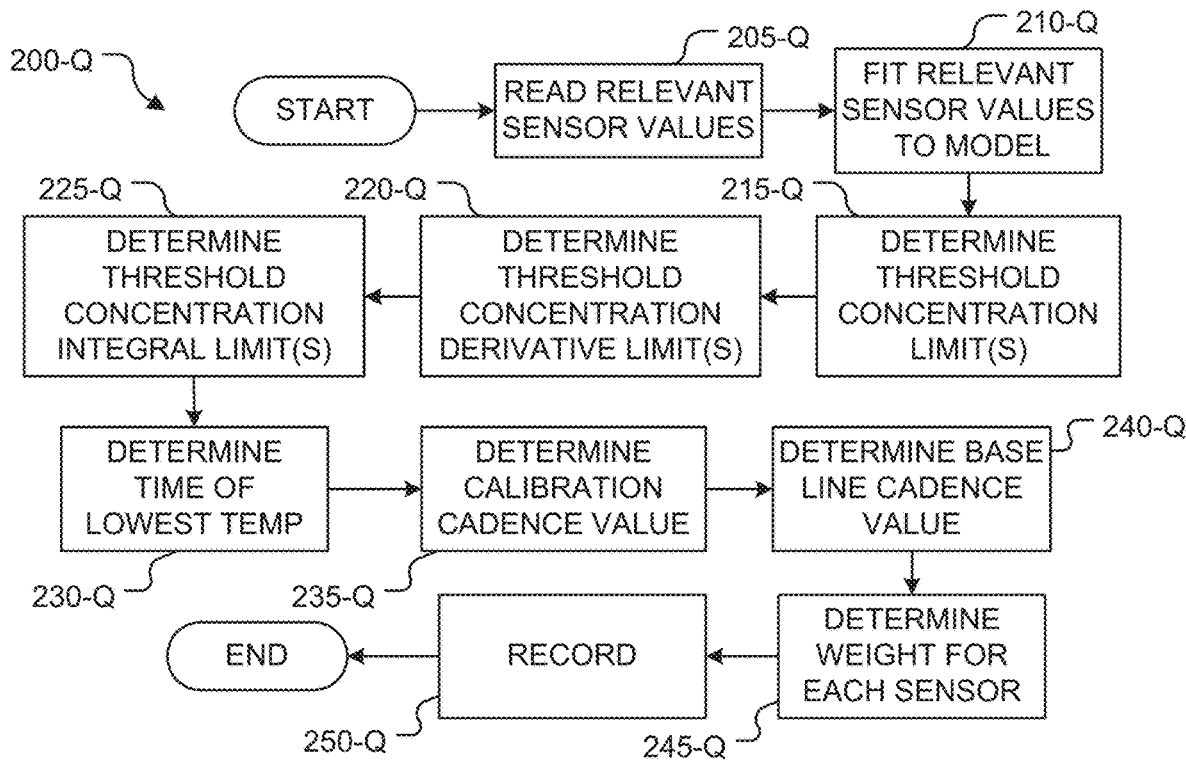
FIG. 7Q is a flow diagram of a relate method performed by the System Controller of FIG. 1.
Figure 7R:
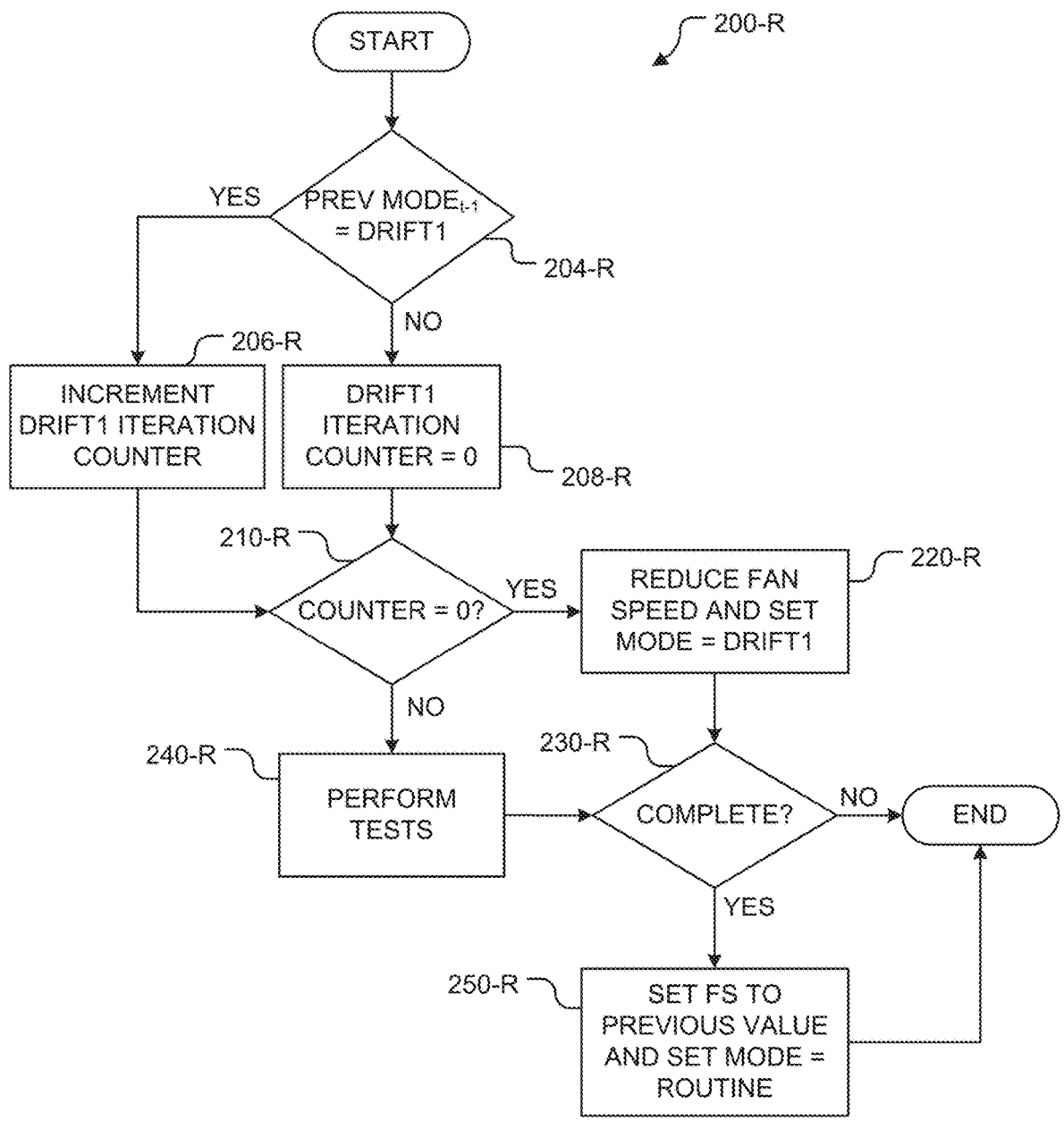
FIG. 7R is a flow diagram of a dilution one test method performed by the System Controller of FIG. 1.
Figure 7S:
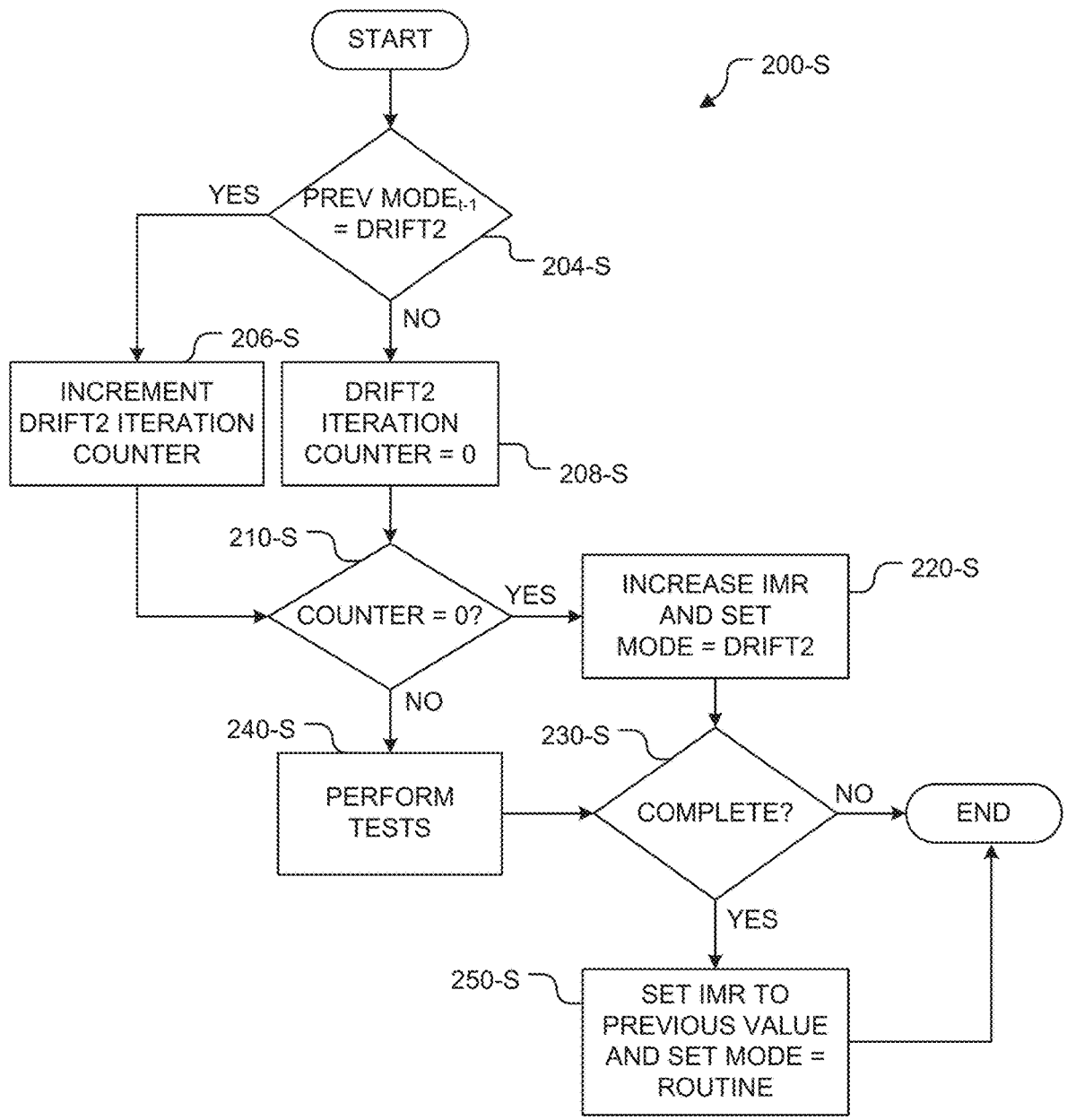
FIG. 7S is a flow diagram of a dilution two test method performed by the System Controller of FIG. 1.
Figure 7T:
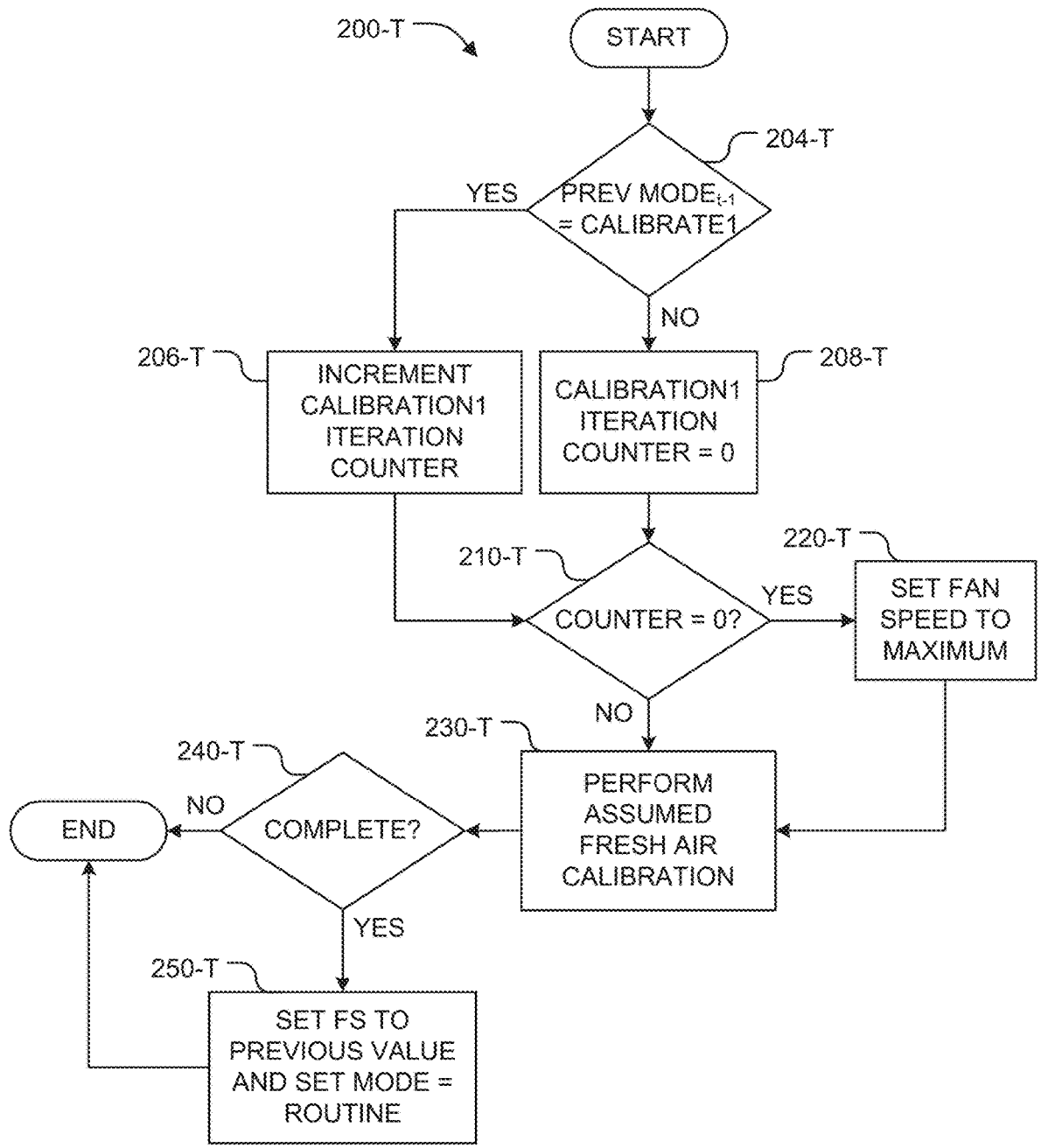
FIG. 7T is a flow diagram of a dilution one calibration method performed by the System Controller of FIG. 1.
Figure 7U:
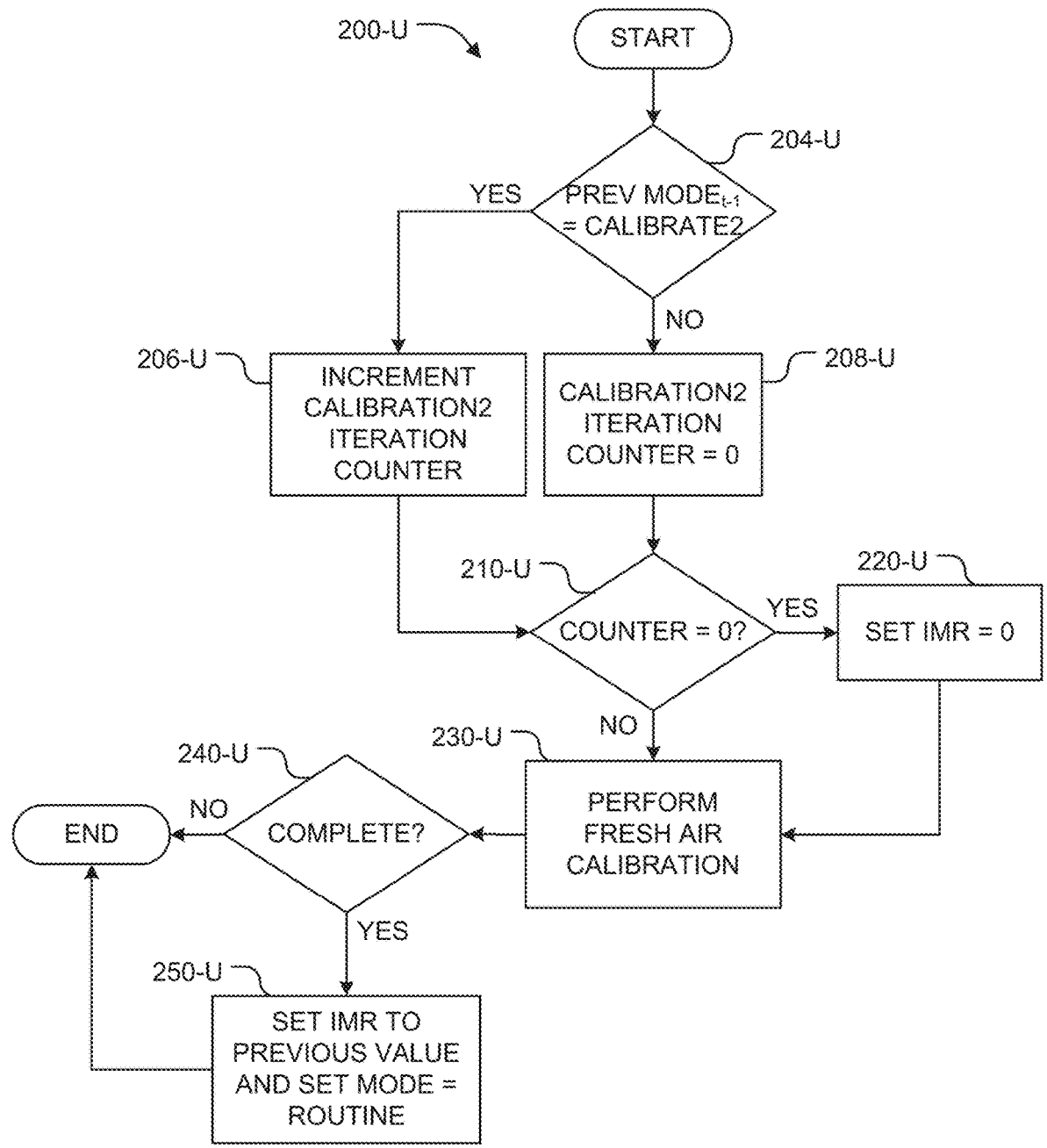
FIG. 7U is a flow diagram of a dilution two calibration method performed by the System Controller of FIG. 1.
Figure 7V:
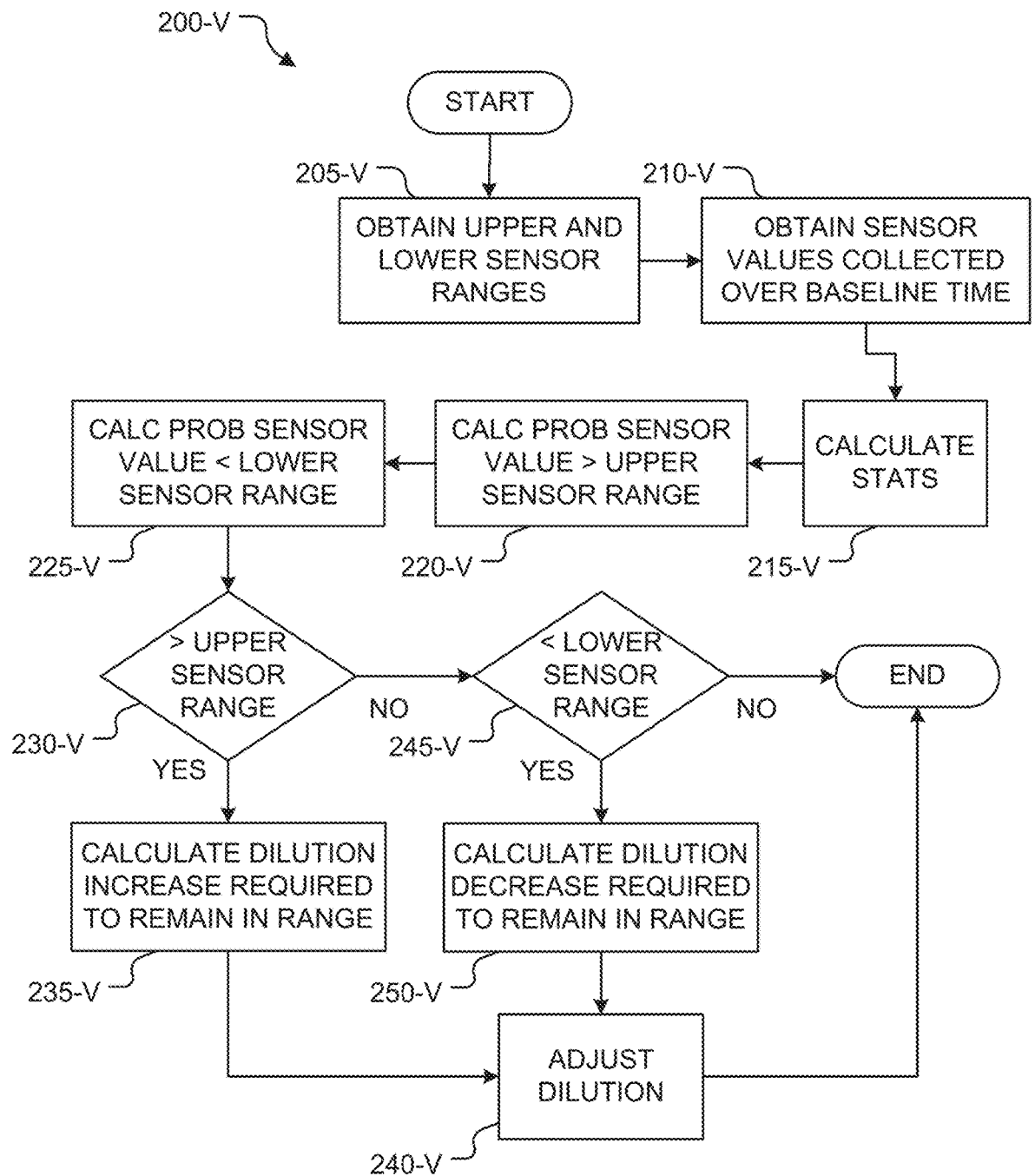
FIG. 7V is a flow diagram of a dilution one range method performed by the System Controller of FIG. 1.
Figure 7W:
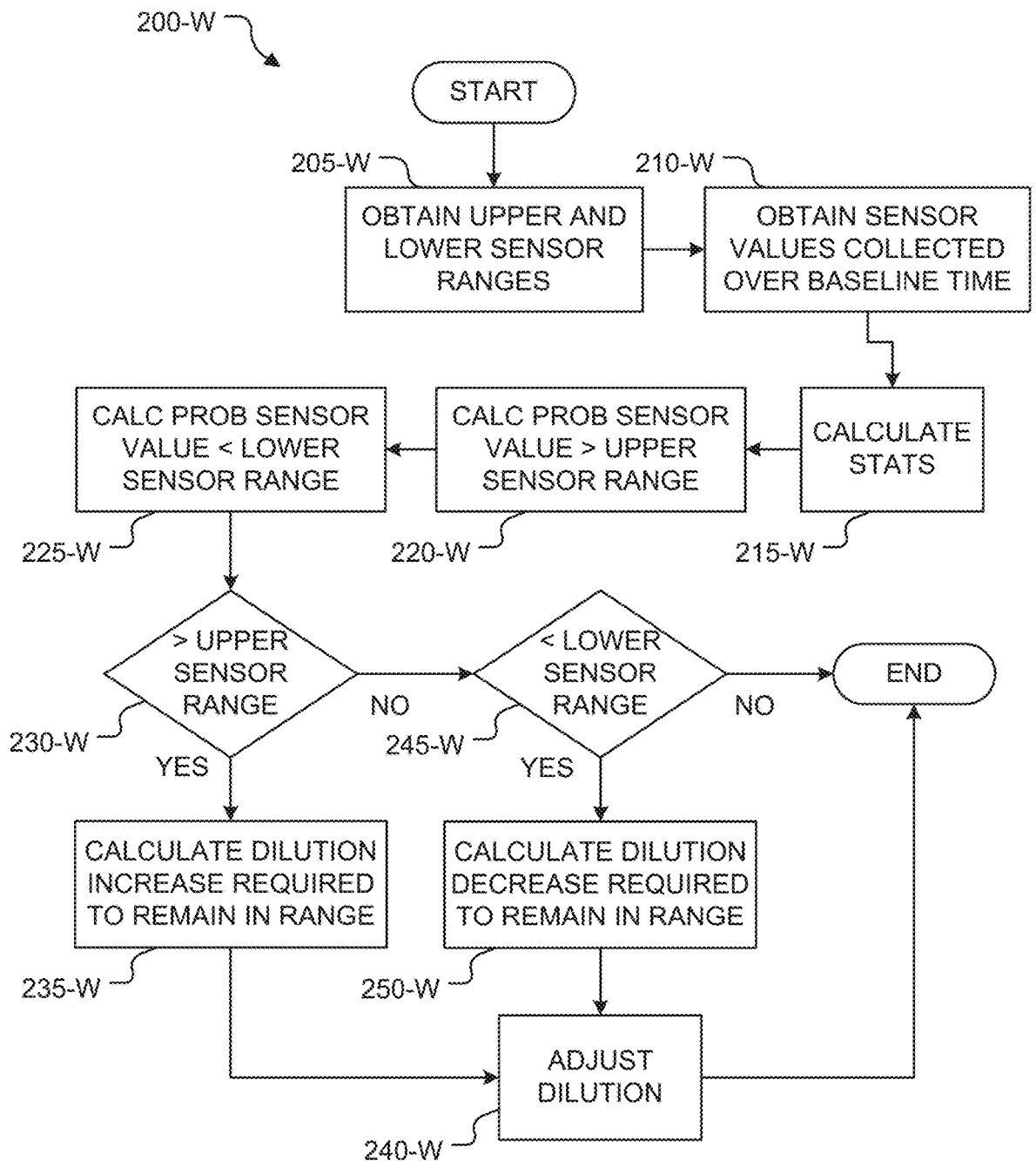
FIG. 7W is a flow diagram of a dilution two range method performed by the System Controller of FIG. 1.

When the decision in decision block 220-O is "YES," in block 230-O, the System Controller 190 performs a dilution two range method 200-W (see FIG. 7W). Then, the desaturate method 200-O terminates.

When the decision in decision block 220-O is "NO," in decision block 240-O, the System Controller 190 determines whether dilution of the first type is available. The decision in decision block 240-O is "YES" when dilution of the first type is available. Otherwise, the decision in decision block 240-O is "NO."

When the decision in decision block 240-O is "NO," the desaturate method 200-O terminates.

When the decision in decision block 240-O is "YES," in block 250-O, the System Controller 190 performs a dilution one range method 200-V (see FIG. 7V). Then, the desaturate method 200-O terminates.

FIG. 7P is a flow diagram of the calibrate method 200-P, which the System Controller 190 may perform in block 255-C of the evaluate method 200-C (see FIGS. 7C-7E) and in block 255-M of the drift validation process 200-M (see FIG. 7M). The System Controller 190 may use the calibrate method 200-P to calibrate the fire detection sensor(s) 216 (e.g., the sensor 128A illustrated in FIG. 3). The fire detection sensor(s) 216 (see FIG. 3) may be recalibrated routinely when the calibration cadence time is exceeded (and the current modes is set to CALIBRATE2 in block 240-E or CALIBRATE1 in block 250-E of FIG. 7E) or on demand to confirm accurate values when an event is detected or an unusual circumstance suggests an additional calibration may be prudent.

In first block 210-P, the System Controller 190 may record the statistics determined in blocks 225-B and 230-B (see FIG. 7B) of the method 200-B (see FIG. 7B).

In decision block 220-P, the System Controller 190 determines whether dilution of the second type is available. The decision in decision block 220-P is "YES" when dilution of the second type is available. Otherwise, the decision in decision block 220-P is "NO."

When the decision in decision block 220-P is "YES," in block 230-P, the System Controller 190 performs a dilution two calibration method 200-U (see FIG. 7U). Then, the calibrate method 200-P terminates.

When the decision in decision block 220-P is "NO," in decision block 240-P, the System Controller 190 determines whether dilution of the first type is available. The decision in decision block 240-P is "YES" when dilution of the first type is available. Otherwise, the decision in decision block 240-P is "NO."

When the decision in decision block 240-P is "NO," the calibrate method 200-P terminates.

When the decision in decision block 240-P is "YES," in block 250-P, the System Controller 190 performs a dilution one calibration method 200-T (see FIG. 7T). Then, the calibrate method 200-P terminates.

FIG. 7Q is a flow diagram of the relate method 200-Q, which the System Controller 190 may perform in block 260-C (see FIG. 7C) of the evaluate method 200-C (see FIGS. 7C-7E). The System Controller 190 performs the relate method 200-Q to find statistical relationships between each sensor's values (C(N)) and both time and temperature (t and T, respectively). Relationships may be determined for proportional, derivative, and/or integral trends.

In first block 205-Q, the System Controller 190 reads sensor values over statistically relevant historical periods (e.g., the baseline time or greater). In block 205-Q, the System Controller 190 may ignore data associated with alarm state values other than the low value (e.g., zero) and/or data associated with a current modes other than ROUTINE.

In block 210-Q, the System Controller 190 fits the relevant sensor data to a model. For example, the System Controller 190 may fit the relevant sensor data to a linear equation, such as Equation 8 below:

$$Y=mt+m'T+b \qquad (8)$$

In Equation 8, a variable m is time-based DRIFT slope, a variable m' is a temperature-based slope, a variable b is the Y-axis intercept, and a variable Y is the difference between a sensor reading and its assumed (calibrated or imputed) value. While Equation 8 may be used to model the data, other equations may also be used. For example, if a linear function of C to time (t) or temperature (T) does not adequately fit the data, additional terms, different equation forms, or variable transformations may be used to reflect such non-linearities.

In block 215-Q, the System Controller 190 determines a threshold concentration limit (e.g., using a user or AI chosen confidence level) for each sensor.

In block 220-Q, the System Controller 190 determines a threshold concentration derivative limit (e.g., using a user or AI chosen confidence level) for each sensor. The derivative (or slope) is with respect to concentration over time.

In block 225-Q, the System Controller 190 determines a threshold concentration integral limit (e.g., using a user or AI chosen confidence level) for each sensor.

In block 230-Q, the System Controller 190 identifies a time of day (e.g., in the diurnal cycle) when the temperature is likely to be lowest.

In block 235-Q, the System Controller 190 determines a calibration cadence ("CC") value. By way of a non-limiting example, the calibration cadence value may be set to 24 hours. Calibration is best done at the lowest temperature, which is determined in block 230-Q. The coolest part of the day in the manhole may depend greatly on the local weather because the temperature of the vault 112 is driven by outside air temperature and load on cables and equipment. Historical values, weather forecasts, and/or load forecasts can be referenced to choose the best time. The slope of the drift is another factor in setting the calibration cadence value. If the drift is not material, the calibration cadence value can be lengthened. On the other hand, if drift is a material issue, the calibration cadence value can be shortened. Calibration with dilution of the second type essentially takes the sensors off-line during a short calibration period. Therefore, maximizing the calibration cadence value provides the most robust monitoring when calibration with dilution of the second type is used.

In block 240-Q, the System Controller 190 determines a baseline cadence ("BLC") value. By way of a non-limiting example, the BLC value may be set to 24 hours. The BLC value is a length of time that elapses between the recalculation of the sensor baseline and threshold values. If the slope of the drift and the noisiness of the data are consistent across two baselines, the BLC value may be increased. The converse suggests a shortening of the BLC value.

In block 245-Q, the System Controller 190 determines a weight for each of the fire detection sensor(s) 216 (e.g., the sensor 128A illustrated in FIG. 3). For example, each of the fire detection sensor(s) 216 (see FIG. 3) may be assigned a weight between zero and one. A weight of zero causes that sensor to be ignored. A weight of zero may be appropriate for a sensor that has failed. A weight of one indicates that the sensor is working as designed and is believed to be providing reliable data. The System Controller 190 may use one or more of the following considerations when assigning a weight to each of the fire detection sensor(s) 216 (see FIG. 3):

1. Sensor signal to noise
   a. time-based
   b. temperature-based
2. Sensor drift
   a. absolute drift
   b. drift stability (second derivative)
3. Sensor within design range
4. Time since calibration
5. Complementary/redundant sensors corroboration
   a. Co-located
   b. Adjacent vaults In block 250-Q, the System Controller 190 records at least some of the values obtained during the performance of the relate method 200-Q (e.g., baseline values and trigger parameters). The System Controller 190 may download at least some of the values obtained during the performance of the relate method 200-Q to the monitor 126. Then, the relate method 200-Q terminates.

FIG. 7R is a flow diagram of the dilution one test method 200-R, which the System Controller 190 may perform in block 225-C (see FIG. 7C) of the evaluate method 200-C (see FIGS. 7C-7E) and in block 230-M (see FIG. 7M) of the drift validation process 200-M (see FIG. 7M). When performing the dilution one test method 200-R, the System Controller 190 adjusts the speed of the air moving device 132 to test if concentrations are perturbed. No perturbation means drift is implicated. On the other hand, perturbations mean measurement is real.

In first decision block 204-R, the System Controller 190 determines whether the previous $mode_{t-1}$ is set to DRIFT1. When the previous $mode_{t-1}$ is set to DRIFT1, in block 206-R, the System Controller 190 increments a drift1 iteration counter (e.g., adds one to the drift1 iteration counter). Then, the System Controller 190 advances to decision block 210-R.

When the previous mode is not set to DRIFT1, in block 208-R, the System Controller 190 initializes the drift1 iteration counter to an initialization value (e.g., zero). Then, the System Controller 190 advances to decision block 210-R.

In decision block 210-R, the System Controller 190 determines if the drift1 iteration counter is equal to the initialization value. The decision in decision block 210-R is "YES" when the drift1 iteration counter equals the initialization value. Otherwise, the decision in decision block 210-R is "NO."

When the decision in decision block 210-R is "YES," in block 220-R, the System Controller 190 saves the previous fan speed then reduces fan speed by half. The System Controller 190 also sets the current $mode_t$ equal to DRIFT1. The fan speed may refer to the speed of the air moving device 132. Then, the System Controller 190 advances to decision block 230-R.

When the decision in decision block 210-R is "NO," in block 240-R, the System Controller 190 performs tests to identify perturbations. The System Controller 190 may perform one or more of following tests until statistically convincing perturbations are recognized within $M_T$ (tau=time constant for dilution of the first type). By way of a non-limiting example, the value of M may be set initially to two and the value of $\tau$ may be set initially to 300 seconds.

1. $CH_2$ should increase from V toward $2V-C_{fresh}$;
2. $Cco_2$ should increase from W toward $2W-C_{fresh}$;
3. Cco should increase from X toward $2X-C_{fresh}$;
4. Cvoc should increase from Y toward $2Y-C_{fresh}$;
5. $Co_2$ should decrease from Z toward $2Z-C_{fresh}$;
6. dC/dt should be positive for $CO_2$, CO, and VOC; and
7. dC/dt should be negative for 02.

In the above tests, $C_{fresh}$ is the concentration of the component in fresh air. For example, the value of $C_{fresh}$ may be 400 ppm for $CO_2$, 10 ppm for CO, 0 ppm for VOC, and 21.2% for 02. When block 240-R is complete, the System Controller 190 advances to decision block 230-R.

In decision block 230-R, the System Controller 190 determines whether the test is complete. The drift test is continued until perturbation is confirmed or not. The decision in decision block 230-R is "YES" when the test is complete. Otherwise, the decision in decision block 230-R is "NO."

When the decision in decision block 230-R is "NO," the current $mode_t$ remains set at DRIFT1 and the dilution one test method 200-R terminates.

When the decision in decision block 230-R is "YES," in block 250-R, the System Controller 190 returns the fan speed to the previous value and sets the current $mode_t$ equal to ROUTINE. Then, the dilution one test method 200-R terminates.

FIG. 7S is a flow diagram of the dilution two test method 200-S, which the System Controller 190 may perform in block 235-C (see FIG. 7C) of the evaluate method 200-C (see FIGS. 7C-7E) and block 215-M (see FIG. 7M) of the drift validation process 200-M (see FIG. 7M). When performing the dilution two test method 200-S, the System Controller 190 adjusts the PID control settings of one or both the air moving devices 178 and 179 (see FIG. 3) to adjust the IMR and test if concentrations are perturbed. No perturbation means drift is implicated. On the other hand, perturbations mean measurement changes are confirmed.

In first decision block 204-S, the System Controller 190 determines whether the previous mode$_{t-1}$ is set to DRIFT2. When the previous mode is set to DRIFT2, in block 206-S, the System Controller 190 increments a drift2 iteration counter (e.g., adds one to the drift2 iteration counter). Then, the System Controller 190 advances to decision block 210-S.

When the previous mode is not set to DRIFT2, in block 208-S, the System Controller 190 initializes the drift 2 iteration counter to an initialization value (e.g., zero). Then, the System Controller 190 advances to decision block 210-S.

In decision block 210-S, the System Controller 190 determines if the drift 2 iteration counter is equal to the initialization value. The decision in decision block 210-S is "YES" when the drift 2 iteration counter is equal to the initialization value. Otherwise, the decision in decision block 210-S is "NO."

When the decision in decision block 210-S is "YES," in block 220-S, the System Controller 190 saves the previous IMR and increases the IMR. The System Controller 190 also sets the current mode$_t$ equal to DRIFT2. The IMR is a mass ratio of vault exhaust air to fresh air and may range from zero to infinity. By way of a non-limiting example, the System Controller 190 may double the IMR. The IMR may be adjusted by adjusting the set point of one or both of the PID controllers and air moving devices 178 and 179. Then, the System Controller 190 advances to decision block 230-S.

When the decision in decision block 210-S is "NO," in block 240-S, the System Controller 190 performs tests to identify perturbations. The System Controller 190 may perform one or more of the following tests until statistically convincing perturbations are recognized within $M_T$ (tau=time constant for dilution of the second type). By way of a non-limiting example, the value of M may be set initially to two and the value of τ may be set initially to 30 seconds.
1. $CH_2$ should decrease from V toward $(V+C_{fresh})/2$;
2. $Cco_2$ should decrease from W toward $(W+C_{fresh})/2$;
3. Cco should decrease from X toward $(X+C_{fresh})/2$;
4. Cvoc should decrease from Y toward $(Y+C_{fresh})/2$;
5. $Co_2$ should increase from Z toward $(Z+C_{fresh})/2$;
6. dC/dt should be negative for $CO_2$, CO, $H_2$, and VOC; and
7. dC/dt should be positive for 02.

In the above tests, $C_{fresh}$ is the concentration of the component in fresh air. For example, the value of $C_{fresh}$ is may be 400 ppm for $CO_2$, 10 ppm for CO, 0.5 ppm for $H_2$, 0 ppm for VOC, and 21.2% for 02. When block 240-S is complete, the System Controller 190 advances to decision block 230-S.

In decision block 230-S, the System Controller 190 determines whether the test is complete. The drift test is continued until perturbation is confirmed or not. The decision in decision block 230-S is "YES" when the test is complete. Otherwise, the decision in decision block 230-S is "NO."

When the decision in decision block 230-S is "NO," the current modes remains set to DRIFT2 and the dilution two test method 200-S terminates.

When the decision in decision block 230-S is "YES," in block 250-S, the System Controller 190 returns the IMR to the previous value and sets the current modes equal to ROUTINE. Then, the dilution two test method 200-S terminates.

FIG. 7T is a flow diagram of the dilution one calibration method 200-T, which the System Controller 190 may perform in block 250-P (see FIG. 7P) of the calibrate method 200-P (see FIG. 7P).

In first decision block 204-T, the System Controller 190 determines whether the previous mode$_{t-1}$ is set to CALIBRATE1. When the previous mode$_{t-1}$ is set to CALIBRATE1, in block 206-T, the System Controller 190 increments a calibration1 iteration counter (e.g., adds one to the calibration1 iteration counter). Then, the System Controller 190 advances to decision block 210-T.

When the previous mode$_{t-1}$ is not set to CALIBRATE1, in block 208-T, the System Controller 190 initializes the calibration1 iteration counter to an initialization value (e.g., zero). Then, the System Controller 190 advances to decision block 210-T.

In decision block 210-T, the System Controller 190 determines whether the calibration1 iteration counter is equal to the initialization value. The decision in decision block 210-T is "YES" when the calibration1 iteration counter is equal to the initialization value. Otherwise, the decision in decision block 210-T is "NO."

When the decision in decision block 210-T is "YES," in block 220-T, the System Controller 190 saves the fan speed of the air moving device 132 then sets the fan speed of the air moving device 132 to full (or 100%) or its maximum setting. Then, the System Controller 190 advances to block 230-T.

When the decision in decision block 210-T is "NO," the System Controller 190 advances to block 230-T.

In block 230-T, the System Controller 190 performs an assumed fresh air calibration. In block 230-T, the System Controller 190 calibrates the fire detection sensor(s) 216 (see FIG. 3) to fresh air conditions.

In decision block 240-T, the System Controller 190 determines whether the assumed fresh air calibration is complete. The decision in decision block 240-T is "YES" when the assumed fresh air calibration is complete. Otherwise, the decision in decision block 240-T is "NO."

When the decision in decision block 240-T is "NO," the current mode$_t$ remains set to CALIBRATE1 and the dilution one calibration method 200-T terminates.

When the decision in decision block 240-T is "YES," in block 250-T, the System Controller 190 sets the fan speed equal to its previous value and sets the current mode$_t$ equal to ROUTINE. Then, the dilution one calibration method 200-T terminates.

FIG. 7U is a flow diagram of the dilution two calibration method 200-U, which the System Controller 190 may perform in block 230-P (see FIG. 7P) of the calibrate method 200-P (see FIG. 7P). When performing the dilution two calibration method 200-U, the System Controller 190 uses 100% fresh air to calibrate the fire detection sensor(s) 216 (e.g., the sensor 128A illustrated in FIG. 3).

In first decision block 204-U, the System Controller 190 determines whether the previous mode$_{t-1}$ is set to CALIBRATE2. When the previous mode$_{t-1}$ is set to CALIBRATE2, in block 206-U, the System Controller 190 increments a calibration2 iteration counter (e.g., adds one to the calibration2 iteration counter). Then, the System Controller 190 advances to decision block 210-U.

When the previous mode$_{t-1}$ is not set to CALIBRATE2, in block 208-U, the System Controller 190 initializes the calibration2 iteration counter to an initialization value (e.g., zero). Then, the System Controller 190 advances to decision block 210-U.

In decision block 210-U, the System Controller 190 determines whether the calibration2 iteration counter is equal to the initialization value. The decision in decision block 210-U is "YES" when the calibration2 iteration counter is equal to the initialization value. Otherwise, the decision in decision block 210-U is "NO."

When the decision in decision block 210-U is "YES," in block 220-U, the System Controller 190 saves the IMR then reduces the IMR to zero. The IMR may be reduced by adjusting the PID control setting of one or both of the air moving devices 178 and 179. Then, the System Controller 190 advances to block 230-U.

When the decision in decision block 210-U is "NO," the System Controller 190 advances to block 230-U.

In block 230-U, the System Controller 190 performs a fresh air calibration using atmospheric values for the component gases.

In decision block 240-U, the System Controller 190 determines whether the fresh air calibration is complete. The decision in decision block 240-U is "YES" when the fresh air calibration is complete. Otherwise, the decision in decision block 240-U is "NO."

When the decision in decision block 240-U is "NO," the current mode$_t$ remains set to CALIBRATE2 and the dilution two calibration method 200-U terminates.

When the decision in decision block 240-U is "YES," in block 250-U, the System Controller 190 sets the IMR equal to the previous IMR value and sets the current mode$_t$ equal to ROUTINE. Then, the dilution two calibration method 200-U terminates.

FIG. 7V is a flow diagram of the dilution one range method 200-V, which the System Controller 190 may perform in block 250-O (see FIG. 7O) of the desaturate method 200-O (see FIG. 7O). When performing the dilution one range method 200-V, the System Controller 190 adjusts the fan speed to compensate for sensors out of range. The fan speed may refer to the speed of the air moving device 132.

In first block 205-V, the System Controller 190 obtains a design range for each of the fire detection sensor(s) 216 (e.g., the sensor 128A illustrated in FIG. 3). Thus, in block 205-V, the System Controller 190 obtains an upper sensor range and a lower sensor range for each of the fire detection sensor(s) 216 (see FIG. 3).

In next block 210-V, the System Controller 190 obtains the sensor values collected over the baseline time for each of the fire detection sensor(s) 216 (see FIG. 3).

In block 215-V, the System Controller 190 calculates statistics for the sensor values obtained in block 210-V. The statistics may include the mean, standard deviation, a maximum value, and a minimum value.

In block 220-V, the System Controller 190 calculates a first probability for each of the fire detection sensor(s) 216 (e.g., the sensor 128A illustrated in FIG. 3) that the sensor values collected over the baseline time are greater than the upper sensor range for the sensor.

In block 225-V, the System Controller 190 calculates a second probability for each of the fire detection sensor(s) 216 (see FIG. 3) that the sensor values collected over the baseline time are less than the lower sensor range for the sensor.

In decision block 230-V, the System Controller 190 determines whether the first probability is greater than a first probability threshold. The decision in decision block 230-V is "YES" when the first probability is greater than the first probability threshold. Otherwise, the decision in decision block 230-V is "NO."

When the decision in decision block 230-V is "YES," in block 235-V, the System Controller 190 calculates an increase in dilution required to target the sensor readings within the sensor range. For example, in block 235-V, the System Controller 190 may calculate an increase in the fan speed. By way of a non-limiting example, if the sensor 128A (see FIG. 3) is near its upper limit, the System Controller 190 may calculate an increase in the fan speed that will keep the sensor 128A within its sensor range. The fan speed may refer to the speed of the air moving device 132. Then, the System Controller 190 advances to block 240-V.

When the decision in decision block 230-V is "NO," the System Controller 190 advances to decision block 245-V. In decision block 245-V, the System Controller 190 determines whether the second probability is greater than a second probability threshold. The decision in decision block 245-V is "YES" when the second probability is greater than the second probability threshold. Otherwise, the decision in decision block 245-V is "NO."

When the decision in decision block 245-V is "YES," in block 250-V, the System Controller 190 calculates a decrease in dilution required to target the sensor readings within the sensor range. For example, in block 250-V, the System Controller 190 may calculate a decrease in the fan speed required to move the sensor readings within the sensor range. The fan speed may refer to the fan speed of the air moving device 132. By way of a non-limiting example, if the CO sensor is always reading zero, the System Controller 190 may calculate a decrease in the fan speed that explores whether CO is present below diluted sensitively. Then, the System Controller 190 advances to block 240-V.

When the decision in decision block 245-V is "NO," the dilution one range method 200-V terminates.

In block 240-V, the System Controller 190 adjusts the dilution (e.g., adjusts the fan speed of the air moving device 132). Then, the dilution one range method 200-V terminates.

It is possible that a condition could exist where one of the fire detection sensor(s) 216 (see FIG. 3) needs a lower fan speed and another one of the fire detection sensor(s) 216 needs a higher fan speed. When this occurs, the dilution one range method 200-V may sequentially increase and decrease the fan speed to accommodate the needs of both sensors or attempt to strike a balance. Additionally, some of the fire detection sensor(s) 216 are more important than others, which may be partially reflected in their weights W(N). The weights may be determined in block 245-Q (see FIG. 7Q) of the relate method 200-Q (see FIG. 7Q).

FIG. 7W is a flow diagram of the dilution two range method 200-W, which the System Controller 190 may perform in block 230-O (see FIG. 7O) of the desaturate method 200-O (see FIG. 7O). When performing the dilution two range method 200-W, the System Controller 190 adjusts the IMR to compensate for sensors out of range. The IMR may be adjusted by adjusting the set points of the PID controllers of one or both of the air moving devices 178 and 179.

In first block 205-W, the System Controller 190 obtains the design range for each of the fire detection sensor(s) 216 (e.g., the sensor 128A illustrated in FIG. 3). Thus, in block 205-W, the System Controller 190 obtains the upper sensor range and the lower sensor range for each of the fire detection sensor(s) 216 (see FIG. 3).

In block 210-W, the System Controller 190 obtains the sensor values collected over the baseline time for each of the fire detection sensor(s) 216 (see FIG. 3).

In block 215-W, the System Controller 190 calculates statistics for the sensor values obtained in block 210-W. The statistics may include the mean, standard deviation, a maximum value, and a minimum value.

In block 220-W, the System Controller 190 calculates a third probability for each of the fire detection sensor(s) 216 (see FIG. 3) that the sensor values collected over the baseline time are greater than the upper sensor range for the sensor.

In block 225-W, the System Controller 190 calculates a fourth probability for each of the fire detection sensor(s) 216 (see FIG. 3) that the sensor values collected over the baseline time are less than the lower sensor range for the sensor.

In decision block 230-W, the System Controller 190 determines whether the third probability is greater than a third probability threshold. The decision in decision block 230-W is "YES" when the third probability is greater than the third probability threshold. Otherwise, the decision in decision block 230-W is "NO."

When the decision in decision block 230-W is "YES," in block 235-W, the System Controller 190 calculates an increase in dilution required to target the sensor readings within the sensor range. For example, in block 235-V, the System Controller 190 may calculate an increase in the IMR. The IMR may be adjusted by varying the PID set points on one or both of the air moving devices 178 and 179. By way of a non-limiting example, if the sensor 128A (see FIG. 3) is near its upper limit, the System Controller 190 may calculate an increase IMR that will keep the sensor 128A within its sensor range. Then, the System Controller 190 advances to block 240-W.

When the decision in decision block 230-W is "NO," the System Controller 190 advances to decision block 245-W. In decision block 245-W, the System Controller 190 determines whether the fourth probability is greater than a fourth probability threshold. The decision in decision block 245-W is "YES" when the fourth probability is greater than the fourth probability threshold. Otherwise, the decision in decision block 245-W is "NO."

When the decision in decision block 245-W is "YES," in block 250-W, the System Controller 190 calculates a decrease in dilution required to remain the sensor readings within the sensor range. For example, in block 250-W, the System Controller 190 may calculate a decrease in the IMR required to target the sensor readings within the sensor range. The IMR is adjusted by varying the set points of the PID controllers of one or both of the air moving devices 178 and 179. By way of a non-limiting example, if the CO sensor is always reading zero, the System Controller 190 may calculate a decrease in the IMR that explores whether CO is present below diluted sensitively. Then, the System Controller 190 advances to block 240-W.

When the decision in decision block 245-W is "NO," the dilution two range method 200-W terminates.

In block 240-W, the System Controller 190 adjusts the dilution (e.g., adjusts the IMR). The IMR may be adjusted by adjusting the PID controller set points of one or both of the air moving devices 178 and 179. Then, the dilution two range method 200-W terminates.

It is possible that a condition could exist where one of the fire detection sensor(s) 216 (see FIG. 3) needs a lower IMR and another one of the fire detection sensor(s) 216 needs a higher IMR. When this occurs, the dilution two range method 200-W may sequentially increase and decrease the IMR to accommodate the needs of both sensors or attempt to strike a balance. Additionally, some of the fire detection sensor(s) 216 (see FIG. 3) are more important than others, which may be partially reflected in their weights W(N). The weights may be determined in block 245-Q (see FIG. 7Q) of the relate method 200-Q (see FIG. 7Q).

FIGS. 8A and 8B illustrate the exemplary sensor readings (identified by the squares 206) obtained from one of the fire detection sensor(s) 216 (e.g., the sensor 128A illustrated in FIG. 3). In the example presented in FIGS. 8A and 8B, the sensor is a carbon dioxide concentration sensor configured to measure part-per-million ("ppm") of carbon dioxide in the internal atmosphere 124 (see FIG. 1). In both FIGS. 8A and 8B, the x-axis is time and the y-axis is ppm of carbon dioxide.

FIG. 8A illustrates sensor readings received from the carbon dioxide concentration sensor over a 63-day period from May 10, 2018, to about Jul. 12, 2018. In this example, the underground vault 112 is located in the northeast coast of North America. A triple line NNN shows the approximate sensor drift over the 63-day period starts around 700 ppm on May 10 and ends at about 1,400 ppm on July 9. Large positive variations (e.g., readings V1 and V2) indicate burning events within or adjacent to the manhole vault 112.

The triple line NNN is a time weighted moving average of non-event data. Non-event data are data collected when the alarm trigger state was "AS0." Time weighting assigns lessor weights to older data points. Time weighting factors are determined statistically. For computational efficiency, those data points collected when the alarm trigger state was "AS0" with time weightings below a threshold value (e.g., determined based on sensor experience) are dropped from the moving average.

FIG. 8B is a subset of the data of FIG. 8A over a single 24 hour time period on May 24, 2018. The y-axis has been enlarged and shows only a range of 400 ppm to 800 ppm. As mentioned above, the triple line NNN shows approximate sensor drift. Over the 24 hour period of FIG. 8B, the sensor drift is insignificant and the triple line NNN has a slope that is essentially zero. Thus, FIG. 8B illustrates a time period during which variations in the data were primarily caused by something other than sensor drift (referred to as "non-drift variations"). Non-limiting examples of non-drift variations include stochastic variations within the sensor mechanism, stochastic variations within the hardware systems where analog signals are converted to digital signals, and natural and man-made perturbations to the analyte or property being measured. Man-made perturbations may include, for example, a running car parked over a manhole cover, which will perturb the level of $CO_2$ inside the manhole upward (or increase the level of $CO_2$) until the car drives away. During this same time period, the aforementioned non-drift variations yield sensor readings between about 600 ppm and 725 ppm. The upper and lower confidence bounds UB and LB are established by a maximum likelihood estimate or similar statistical technique and provide a defined level of confidence that a value outside those bounds is quite unlikely (e.g., less than 5% or perhaps less than 1%) to be caused by drift or non-drift variations, but rather is very likely (e.g. greater than 95% or perhaps greater than 99%) a perturbation worthy of corroboration.

For example, the upper and lower confidence bounds UB and LB may be determined by adding and subtracting a noise threshold from an average sensor reading. The average sensor reading and a standard deviation may be determined for the sensor from historical sensor readings. Additionally, the upper and lower confidence bounds UB and LB may be determined from percentile values and/or upper-tile averages on distributions that are highly skewed. New sensor readings falling between the upper and lower confidence bounds UB and LB are identified as noise. The historical sensor readings include a number of past samples collected over a past time period. The past time period and number of past samples depends on the characteristics of the sensor and the environment in which it operates. Typically sensor measurements are recorded every 15 minutes and, thus, about 96 measurements are recorded every day. The past time period may include one day, two days, or more. The noise threshold may be determined by the System Controller 190 using maximum-likelihood statistics or similar means to achieve a user-defined probability threshold. By way of non-limiting examples, 90%, 95%, and 99% may be used as user-defined probability thresholds. Thus, the noise threshold may include all values that are statistically within a user selected confidence interval (e.g., 90%, 95%, and 99%) of the average sensor reading. Older measurements in the historical sensor readings may be weighted less than or equal to more contemporary measurements when the average sensor reading is calculated. Unequal weighting is most appropriate where the sensor drift is mathematically significant over the length of time chosen to calculate the average and standard deviation.

Using the sample data of FIGS. 8A and 8B, it is clear that over any single day the drift is very small but, over the 63-day period, the impact of the drift is about a factor of two. Thus, a 24-hour period is about right to determine a baseline, the average sensor reading, and the standard deviation for this sensor. Longer time periods can improve the statistical veracity of the estimations. Therefore, an appropriate time period to calculate the baseline, the average sensor reading, and the standard deviation for this sensor in this environment may be about 24 hours to 48 hours. Longer times are possible, but including more historical data provides diminishing returns of statistical veracity and suffers from additional computational demands.

While the triple line NNN, the upper confidence bound UB, and the lower confidence bound LB shown in FIG. 8B appear to be horizontal because of the scale choice, they in fact each have a small positive slope, $\Delta C/\Delta t$. For example, the average slope from FIG. 8A over the 63 day time period is the difference between about 1200 ppm (on July 11$^{th}$) and about 700 ppm (on May 10th) divided by 63 days, which is about 7.9 ppm/day. Inspection of FIG. 8A for the 24 hour time period illustrated in FIG. 8B reveals that the slope on May 24th is less than 7.9 ppm/day. The drift slope can be used to refine an anticipated data point, but such a refinement is generally unnecessary as the noise exemplified in FIG. 8B is generally much greater than the drift. In the 24 hour period illustrated in FIG. 8B, the span of the noise is about 125 ppm or more than an order of magnitude greater than the drift.

Component Mass Balance

As mentioned above, a component mass balance may be used in block 206-K (see FIG. 7K) of the calculate method 200-K (see FIG. 7K) to determine a FGA rate and/or in block 242-K (see FIG. 7K) of the calculate method 200-K (see FIG. 7K) to determine a burn rate.

For brevity in the discussion that follows, all input values and estimates are described as single deterministic values. Of course, all measurements are estimates of reality and all estimates include error. Therefore, probabilistic inputs may be used for each input described in deterministic terms below and a Monte Carlo simulation of those inputs may be used to provide probabilistic outputs. This probabilistic approach allows the end user of the information to judge the voracity of the results. For example, both a deterministic percentage lower explosive limit ("% LEL") and a probabilistic % LEL may be determined. % LEL is a fraction of flammable components relative to that fraction which would support an explosion. If the deterministic % LEL is determined to be 75%, the user might take comfort that an explosion is unlikely. However, if the same result were reported probabilistically as 75% MLE (maximum likelihood estimate) with 95% confidence levels at 71% (lower) and 103% (upper), the user is more likely to have a higher level of alarm and make a better decision.

Referring to FIG. 1, even if the absolute output values of the fire detection sensor(s) 216 (see FIG. 3) are reliable, the dynamics of these systems are indeterminate. With passive ventilation, the flow of gases in and out of the underground vault 112 is practically unknowable. Only with active ventilation, where the exhaust flow rate can be measured or estimated and the concentrations of the analytes in the exhaust can be measured or estimated, is it possible to perform a robust component mass and energy balance on the vault environment. The mass balance allows an assessment of the size of a fire or other source of dangerous gases. For example, a smoldering cigarette would be of little concern, but a fire that is consuming 100 grams of polymer per minute would constitute a substantial event. The former requires no action while the later demands immediate action to protect the public.

The System Controller 190 may use component mass balance to determine one or more of the following:
1. relevant alarm condition(s);
2. the alarm state level for an associated alarm condition;
3. the lower explosive limit ("LEL") of the mixture of flammable gases in air;
4. a corrected lower explosive limit ("CLEC") of the mixture of flammable gases that accounts for an abundance of non-flammable gases introduced by oxidative decomposition;
5. anticipated dilution of $O_2$ and $N_2$;
6. an amount of energy being dissipated by active ventilation; and
7. an amount of water being transported from the vault 112 by evaporation.

Regarding determining relevant alarm condition(s), manhole events may include oxidative decomposition, pyrolysis, and/or plasmatization. The component mass balance allows the event to be labeled. The benefit of this knowledge may be critical to respond properly to the manhole event. For example, oxidative decomposition is exothermic and potentially self-sustaining, meaning it requires different intervention than pyrolysis and plasmatization, which are endothermic and can be halted by shutting the power off to burning equipment.

Regarding determining the alarm state level for an associated alarm condition, the System Controller 190 may use component mass balance to determine the size of a combustion event. Large events have greater urgency than smaller events and very small events would represent nuisance alarms (or an alarm where no action is required.)

Figure 18:
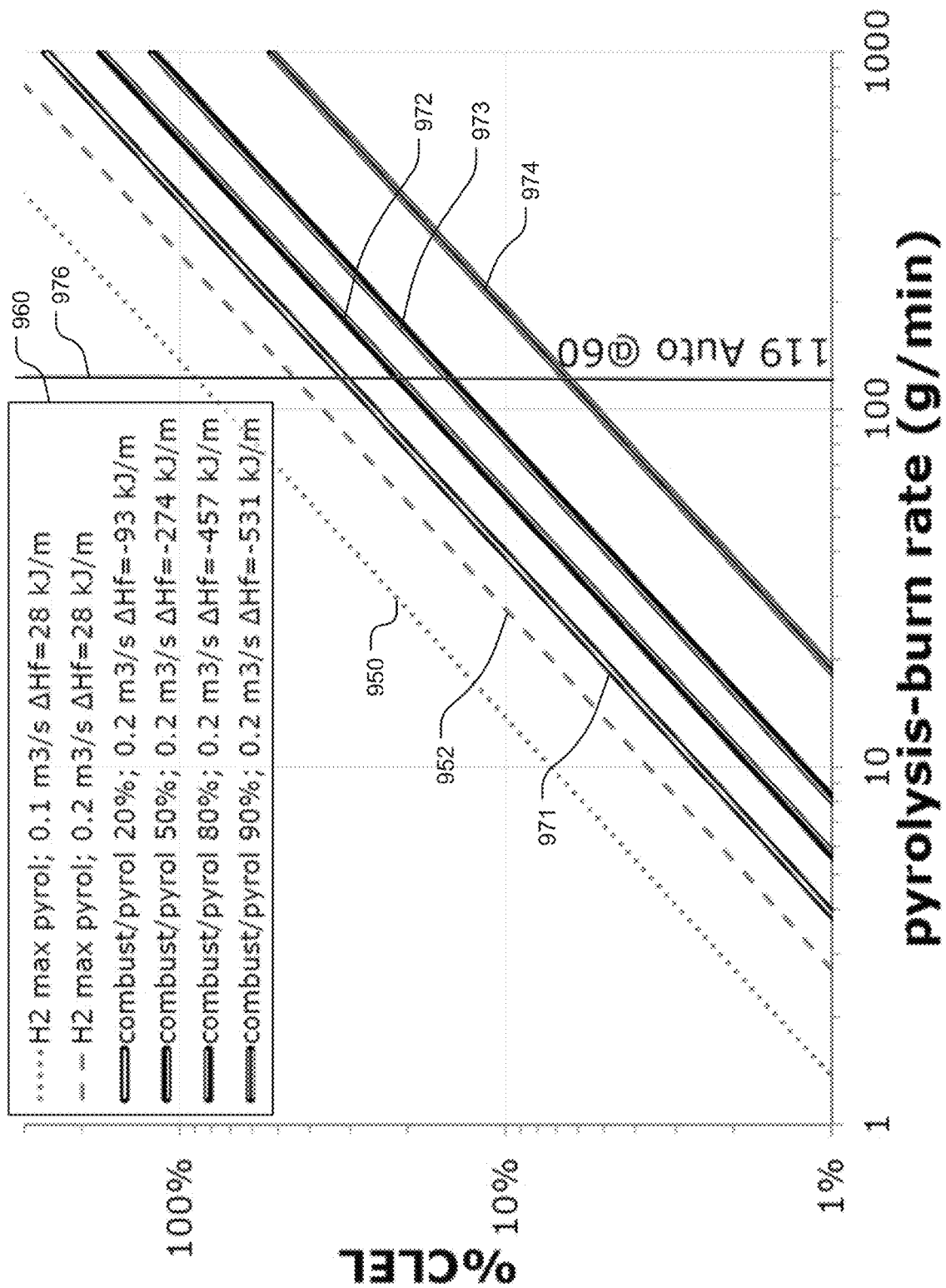
FIG. 18 is a graph illustrating how oxidative decomposition and pyrolysis can create flammable atmospheres inside one or more vaults.

FIG. 18 illustrates how various burning (oxidative decomposition and pyrolysis) cases can create flammable atmospheres in vaults. The logarithmic x-axis is burn rate expressed in grams per minute. The y-axis is the gas mixture concentration expressed as a percentage of the CLEL (%

CLEL). Ignition and explosion are not possible until the % CLEL is greater than 100%. The LEL (by definition in air) of a mixture of flammable gases is calculated using Equation 9 (below), which is Le Chatelier's formula:

$$1/LEL_{mix} = c_1/LEL_1 + c_2/LEL_2 + c_3/LEL_3 + \ldots + c_n/LEL_n \qquad (9)$$

In Equation 9, variables $c_1$, $c_2$, $c_3$, ... $c_n$ are mole fractions of n component gases in the mixture having lower explosive limits of $LEL_1$, $LEL_2$, $LEL_3$, ..., $LEL_n$ respectively. The sum of the mole fractions, $c_1$, $c_2$, $c_3$, ... $c_n$, is unity.

The mixture LEL (i.e., $LEL_{mix}$) is corrected for dilution by inert gases above the levels found in the atmosphere by Equation 10 (below), which is Kondo's equation (S. Kondo, K. Takizawa, A. Takahashi, K. Tokuhashi, "Extended Le Chatelier's formula for carbon dioxide dilution effect on flammability limits," Journal of Hazardous Materials A138 (2006) 1-8):

$$c_{mix}/CLEL = C_{mix}/LEL_{mix} + p \cdot (1 - c_{mix}) \qquad (10)$$

In Equation 10, variable $c_{mix}$ is the mole fraction of the flammable gases in the fuel-inert gas mixture, variable CLEL is the mixture LEL corrected for the inert gases (e.g. $CO_2$, $H_2O$) in excess of normal atmospheric inert gases, variable $LEL_{mix}$ is the LEL of the mixture in air, and variable p is an experimentally determined parameter with a typical value of about –0.01.

In FIG. 18, the dependent variable is plotted for each burn rate, each fire type, and a specified exhaust rate. A dotted line 950 (corresponding to $H_2$ max pyrol; 0.1 m³/s $\Delta H_f$=28 kJ/m) and a dashed line 952 (corresponding to $H_2$ max pyrol; 0.2 m³/s $\Delta H_f$=28 kJ/m) demonstrate a hypothetical worst-case scenario where 100% of the hydrogen in the polymer is pyrolyzed to $H_2$. In the first case shown by the dotted line 950, active ventilation is exhausting 0.1 m³/sec and, in the second case shown by the dashed line 952, the exhaust is doubled. This hypothetical worst-case scenario is not possible because such pyrolysis cannot occur until temperatures are about 500° C. Such temperatures are not possible (because emergency overload design temperatures for electrical equipment are less than 200° C.) without an oxidative combustion process, because pyrolysis is endothermic. For each case in FIG. 18, a legend 960 includes the approximate net heat of formation ($\Delta H_f$) for the burn. Positive values are endothermic and cannot sustain; negative values are exothermic and are potentially sustainable in the duct-vault environment. The aforementioned dotted and dashed lines 950 and 952 are entirely hypothetical. Four solid compound lines 971-974 illustrate where combustion and pyrolysis are mixed from 20% to 90% oxidation. The solid compound lines 971-974 illustrate 20% oxidation, 50% oxidation, 80% oxidation, and 90% oxidation respectively. Each of the solid compound lines 971-974 depicts an example with negative (favorable) net heat of formation and represents a realistic burn scenario.

To distinguish nuisance fires from fires of consequence, consider some examples. A smoking cigarette weights about 1 gram and is consumed in about 5 minutes. Its burn rate is thus about 0.2 g/min. A cigarette in a vault is obviously a nuisance. A typical candle burns about 0.1 g/min and hence 100 candles would yield 10 g/min. Thus, even 100 candles do not have a significant burn rate. On the other hand, a typical auto traveling at 60 mph consumes about 119 g/m in. This value is illustrated with a vertical line 976 labeled "119 Auto @60" in FIG. 18. The example automobile is consuming considerable fuel and, therefore, may be considered a fire of consequence.

A fire having a burn rate of 100 g/m in or greater is a pretty serious fire. On the other hand, burn rates that are less than 1 g/min can be largely ignored unless they persist for long periods or grow with time. The character of a fire has a large impact on its severity. For example, fires with high oxidative character are much less likely to lead to an explosion. Vault owners will want to deal with large fires in any case. One of ordinary skill in the art would recognize that the size of the fire (or its pyrolysis-burn rate) and the oxidative character of the fire impact both the % LEL and likelihood of an explosion.

Regarding an amount of energy being dissipated by active ventilation vault, owners are faced with equipment that ages at least partially based upon the temperature at which the equipment operates. As a general rule of thumb, each 10° C. of temperature doubles the rate of oxidation or aging. Understanding how much energy is dissipated by active ventilation allows the vault owner to adjust their expectations for scheduled maintenance of equipment.

Regarding determining anticipated dilution of 02 and $N_2$, when it is desirable to dilute potentially explosive gases within the underground vault 112, dilution of the first type may be used to exhaust the internal atmosphere 124 up to the maximum exhaust rate. Atmospherically rich components $O_2$ and $N_2$ decrease in concentration by dilution when there is an increase in combustion by-products or an increase in flammable gases by dilution. The magnitude of the dilution can be estimated when the exhaust rate is known. Performing a component mass balance (discussed below) yields the anticipated dilution of 02 and $N_2$.

Regarding determining an amount of water being transported from the vault 112 by evaporation, there are reliability and convenience benefits in keeping manholes dry. In conjunction with water level measurement, the effectiveness of water control features can be evaluated.

Figure 19:
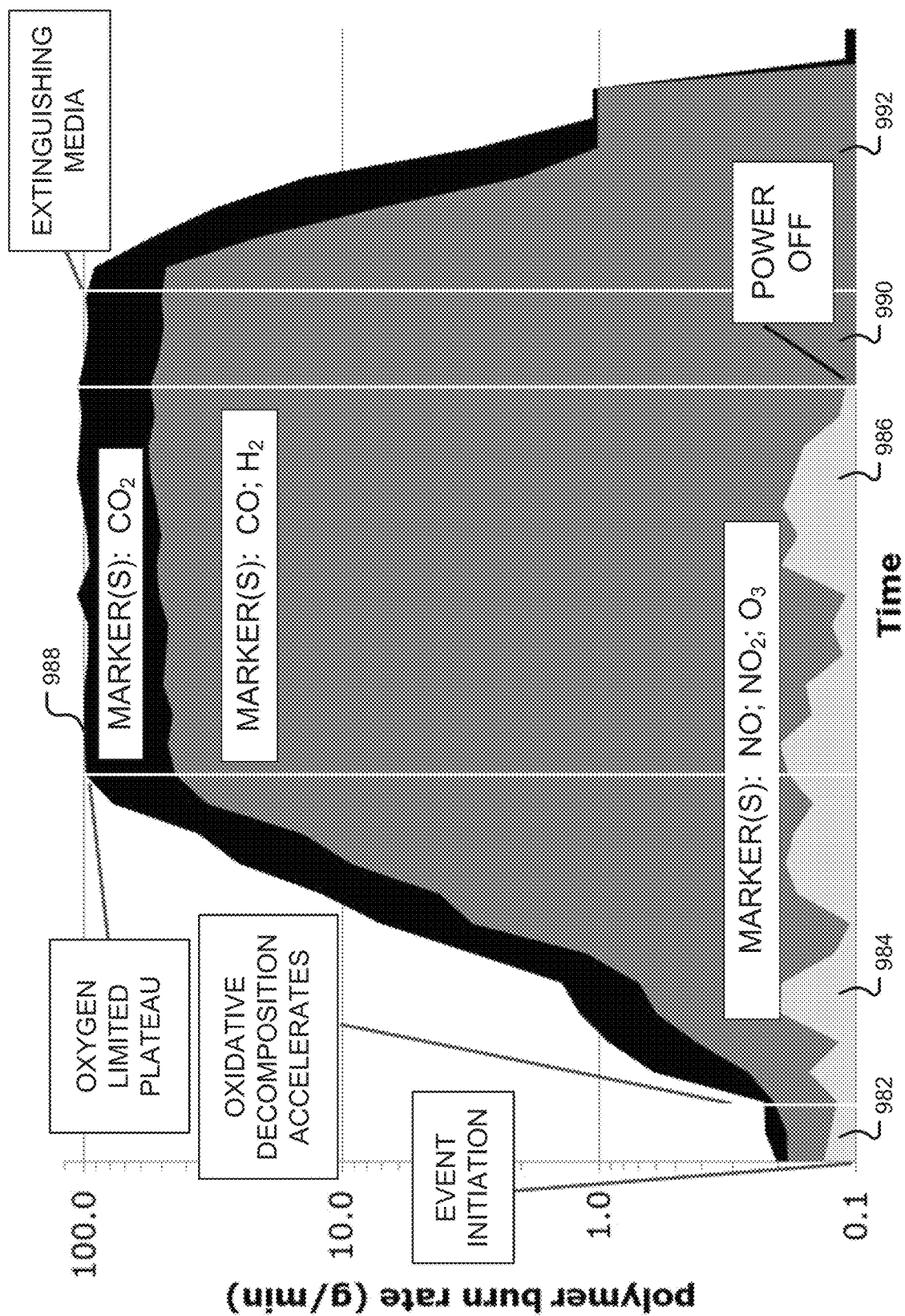
FIG. 19 is a graph illustrating typical evolution of a manhole event from initiation to extinguishment.

FIG. 19 illustrates typical evolution of a manhole event from initiation to extinguishment. Events in a manhole generally follow a somewhat predictable progression with time. As a non-limiting example of such a progression and using a secondary network as an example, a manhole event most likely starts as surface tracking on a old/damaged cable. During a first phase 982, the predominate mechanism is plasmatization, which creates compounds like NO, $NO_2$, and 03. Of course, the temperature of plasma is 30,000° F. so some pyrolysis and oxidation also occur. Plasmatization and pyrolysis are both endothermic so they cannot grow or maintain themselves without oxidation. At this stage of the fire, oxygen is plentiful in the duct. Oxidation creates carbon dioxide and water, is exothermic, and is a prerequisite for a growing fire. A second phase 984 begins when oxidative decomposition becomes self-sustaining. This second phase continues as the fire grows until the fresh supply of oxygen is exhausted. A third phase 986 is represented by a plateau 988. The plateau 988 represents the maximum burn rate based upon the amount of oxygen available. A fourth phase 990 occurs when the vault owner shuts power off to the circuit. The plasmatization has been marked by stochastic behavior as electrical paths are destroyed and reinitiated during the event. Once the power is turned off, plasmatization terminates immediately. With less energy supplied to the event, a small decrease in the plateau 988 may occur. A fifth phase 992 of the event will not occur until an extinguishing medium is introduced or the polymer is entirely consumed. During this fifth phase 992 the fire subsides. Knowing where a particular manhole event is along this event development continuum allows the circuit owner to take appropriate action—urgent or not so urgent.

FIG. 9 is a flow diagram of a method 300 of conducting a component mass balance that may be performed by the System Controller 190. Component mass balance may be used to calculate flows into and out of the underground vault 112. Active ventilation allows the underground vault 112 to be considered a continuous stirred tank ("CST"). The exhaust flow $F_E$ equals the fresh air flow $F_{FA}$ of gases and particulates from the external atmosphere 122, the connection(s) flow $F_C$ of gases and particulates into the internal atmosphere 124 from another source (e.g., one or more connections 118A-118J connected to the underground vault 112), the evaporation flow $F_V$ of evaporating liquids, and a change in water depth (referred to as $\Delta Depth_{water}$). Thus, this relationship may be described using Equation 11, which is a total gaseous mass balance equation:

$$F_E = F_{FA} + F_C + F_V + \Delta Depth_{water} \quad (11)$$

Each value in the total gaseous mass balance equation is expressed in gaseous mass (or equivalent for water depth) per unit time. The System Controller 190 may estimate the change in water depth (referred to as $\Delta Depth_{water}$) with time using data received from the water level sensor 214. Influx of water is positive flow and outflow is negative flow. The System Controller 190 may estimate a volume of air displaced by the water influx. Failure to calculate $\Delta Depth_{water}$ would create an error in the overall mass balance. The change in water depth is often negligible and may be ignored in many cases. However, in some vaults near sea coasts, tidal conditions create twice daily flooding and reverse flooding of vaults that should not be ignored.

The connection(s) flow $F_C$ includes net gas flows from a fire regardless of where the fire is located. There is much more cable located within the connections 118A-118J connected to the vaults 112-116 than there is cable in the vaults, and hence the connection(s) flow $F_C$ is most likely from one of the connections. However, the fire may also originate in one of the vaults 112-116. For the purpose of this component mass balance, where the fire is located (e.g., in one of the connections 118A-118J or vaults 112-116) is a distinction without a difference.

In first block 310, the System Controller 190 obtains vault parameters. By way of a non-limiting example, the System Controller 190 may perform a method 350 (see FIG. 10) to obtain the vault parameters. In this example, the vault parameters include a dry vault volume and an atmospheric pressure.

In block 320, the System Controller 190 obtains exhaust flow parameters for the exhaust flow $F_E$. By way of a non-limiting example, the System Controller 190 may perform a method 400 (see FIG. 11) to obtain the exhaust flow parameters. In this example, the exhaust flow parameters include the following:
1. an exhaust flow rate,
2. an exhaust temperature value $T_E$,
3. a vault turnover (e.g., in seconds), and
4. exhaust component parameters.

The exhaust component parameters may include one or more of the following values for each component of the exhaust flow $F_E$:
1. Concentration of the exhaust component (see second column of Table B); and
2. Mass flow rate (g/s) of the exhaust component (see rightmost column of Table B).

For example, if the exhaust flow rate is about 0.047 m³/s, the exhaust temperature value $T_E$ is about 25° C. (77° F.), and turnover is about 428 seconds, Table B lists exemplary exhaust component parameters.

TABLE B

| Component | Volume | Unit | mole/m³ | Mass (g/m³) | Mass (g/s) |
|---|---|---|---|---|---|
| $O_2$ | 20.81% | v | 8.507291 | 272.21631 | 12.84589 |
| $CO_2$ | 4,000 | ppm | 0.163496 | 7.19547 | 0.33955 |
| CO | 40 | ppm | 0.001635 | 0.04580 | 0.00216 |
| $H_2O$ (RH = 0.67) | 20,945 | ppm | 0.856103 | 15.42294 | 0.72781 |
| $H_2S$ | — | ppm | 0.000000 | 0.00000 | 0.00000 |
| $SO_2$ | — | ppm | 0.000000 | 0.00000 | 0.00000 |
| VOC ($CH_4$) | 178 | ppm | 0.007276 | 0.11670 | 0.00551 |
| NO | 7 | ppm | 0.000286 | 0.00859 | 0.00041 |
| $NO_2$ | 17 | ppm | 0.000695 | 0.03197 | 0.00151 |
| $O_3$ | 11 | ppm | 0.000450 | 0.02158 | 0.00102 |
| $H_2$ | 64 | ppm | 0.002606 | 0.00525 | 0.00025 |
| $N_2$ | 76.7% | v | 31.334221 | 877.77806 | 41.42235 |
| Soot (C) | 38 | µg/m³ | 0.000003 | 0.00004 | 0.00000 |
| Ash ($SiO_2$) | — | µg/m³ | | | 0.00000 |
| Total: | 100% | v | 40.874 | 1172.84 | 55.34644 |

In block 330, the System Controller 190 obtains fresh air flow parameters for the fresh air flow $F_{FA}$. By way of a non-limiting example, the System Controller 190 may perform a method 500 (see FIG. 12) to obtain the fresh air flow parameters. In this example, the fresh air flow parameters include the following:
1. a fresh air flow rate,
2. a fresh air temperature value TFA, and
3. fresh air component parameters.

The fresh air component parameters may include one or more of the following values for each component of the fresh air flow $F_{FA}$:
1. Concentration of the fresh air component (see second column of Table C); and
2. Mass flow rate (g/s) of the fresh air component (see rightmost column of Table C).

For example, if the fresh air flow rate is about 0.0463981 m³/s and the fresh air temperature value is about 25° C. (77° F.), Table C lists exemplary fresh air component parameters.

TABLE C

| Component | Volume | Unit | mole/m³ | Mass (g/m³) | Mass (g/s) |
|---|---|---|---|---|---|
| $O_2$ | 20.81% | v | 8.5072913 | 272.21631 | 12.63033 |
| $CO_2$ | 400 | ppm | 0.0163496 | 0.71955 | 0.03339 |
| CO | 4 | ppm | 0.0001635 | 0.00458 | 0.00021 |
| $H_2O$ (RH = 0.5) | 15,631 | ppm | 0.638883 | 11.5097 | 0.53403 |
| $H_2S$ | — | ppm | 0.000000 | 0.0000 | 0.00000 |
| $SO_2$ | — | ppm | 0.000000 | 0.0000 | 0.00000 |
| VOC ($CH_4$) | 22 | ppm | 0.000899 | 0.0144 | 0.00067 |
| NO | — | ppm | 0.000000 | 0.0000 | 0.00000 |
| $NO_2$ | — | ppm | 0.000000 | 0.0000 | 0.00000 |
| $O_3$ | — | ppm | 0.000000 | 0.0000 | 0.00000 |
| $H_2$ | — | ppm | 0.000000 | 0.0000 | 0.00000 |
| $N_2$ | 77.6% | v | 31.710472 | 888.3181 | 41.21631 |
| Soot (C) | — | µg/m³ | 0.000000 | 0.0000 | 0.00000 |
| Ash ($SiO_2$) | — | µg/m³ | 0.000000 | 0.0000 | 0.00000 |
| Total: | 100% | v | 40.874058 | 1172.782641 | 54.41494 |

In block 340, the System Controller 190 obtains connection(s) flow parameters for the connection(s) flow $F_C$. By way of a non-limiting example, the System Controller 190 may perform a method 600 (see FIG. 13) to obtain the connection(s) flow parameters. In this example, the connection(s) flow parameters the following:

1. a connection(s) flow rate,
2. a connection(s) temperature value Tc, and
3. connection(s) component parameters.

The connection(s) component parameters may include one or more of the following values for each component of the connection(s) flow $F_C$:

1. Concentration of the connection(s) component (see third column of Table D); and
2. Mass flow rate (g/s) of the connection(s) component (see fourth column of Table D).

For example, if the connection(s) flow rate is about 0.000226 m³/s and the connection(s) temperature value is about 25° C. (77° F.), Table D lists exemplary connection(s) component parameters.

TABLE D

| Component | Volume (m³/s) | Mass (%) | Mass (g/s) | Polymer (mol/s) |
|---|---|---|---|---|
| $O_2$ | 0.000000113 | 0.038% | 0.000125 | |
| $CO_2$ | 0.00020 | 93.508% | 0.306169 | 0.00695680 |
| CO | 0.000002 | 0.595% | 0.001949 | 0.00006957 |
| $H_2O$ (RH = 1) | 0.00001 | 3.126% | 0.0102356 | |
| $H_2S$ | 0.00000 | 0.00000% | 0.0000000 | |
| $SO_2$ | — | 0.00000% | 0.0000000 | |
| VOC ($CH_4$) | 0.00001 | 1.47755% | 0.0048379 | 0.00030161 |
| NO | 0.00000 | 0.12375% | 0.0004052 | |
| $NO_2$ | 0.00000 | 0.46073% | 0.0015085 | |
| $O_3$ | 0.00000 | 0.31103% | 0.0010184 | |
| $H_2$ | 0.00000 | 0.07585% | 0.0002483 | |
| $N_2$ | 0.00000 | 0.28291% | 0.0009263 | |
| Soot (C) | 0.00000 | 0.00055% | 0.0000018 | 0.00000015 |
| Ash ($SiO_2$) | — | 0.00000% | 0.0000000 | |
| Total: | 0.00023 | 100.000% | 0.3274247 | 0.0073281 |

Determining the connection(s) flow parameters requires the fresh air flow parameters and vice versa. Thus, as will be described below, portions of blocks 330 and 340 may be performed together. For example, the connection(s) and fresh air flow parameters may be determined iteratively using a method well known in the art, such as direct substitution, Newton-Raphson, and the like. Using such a method, a mass balance error value may be driven to zero by adjusting the fresh air flow rate. The mass balance error value may be equal to a sum of the mass flow rate of the exhaust components (e.g., last row in rightmost column of Table B) minus a sum of the mass flow rate of the fresh air components (e.g., last row in rightmost column of Table C) and a sum of the mass flow rates of the connection(s) components (e.g., last row in fourth column of Table D).

In block 342, the System Controller 190 performs an energy balance and calculates enthalpies (a first exhaust value "$h_e$," a second fresh air value "$h_{fa}$" and a third connection(s) value "$h_c$") and energy exhausted "Δh" for each of the components shown in the leftmost columns of Tables B-D. By way of a non-limiting example, the energy balance may be implemented by a method 700 (see FIG. 14).

In block 344, the System Controller 190 calculates a rate of net water removal "Δw" by the evaporation $F_V$. By way of a non-limiting example, the rate of net water removal "Δw" may be calculated using a method 800 (see FIG. 15).

In block 348, the System Controller 190 provides (e.g., displays) a value of interest. For example, the connection(s) flow $F_C$ may include nitrogen dioxide as a connection(s) component. The connection(s) component parameters for the nitrogen dioxide may be provided as a metric of the size of a combustion event. Thus, these parameters may be used to determine alarm state level for an associated alarm condition. For example, the System Controller 190 may provide the burn rate and/or the FGA.

By way of another example, the connection(s) components of the connection(s) flow $F_C$ may include soot. The connection(s) component parameters for the soot may be provided as a metric of an amount of energy being dissipated by active ventilation. For example, the energy exhausted "Δh" calculated for soot using the energy balance of the method 700 (see FIG. 14) may be used as a metric of the amount of energy dissipated by active ventilation.

By way of another example, the System Controller 190 may provide the rate of net water removal "θw" by the evaporation $F_V$ calculated in block 344.

By way of another example, the System Controller 190 may provide one or more of the enthalpies (e.g., the first exhaust value "$h_e$," the second fresh air value "$h_f$," and the third connection(s) value "$h_c$") and/or the energy exhausted "Δh" for at least one of the component of the flows $F_E$, $F_{FA}$, and $F_C$.

Then, the method 300 terminates.

FIG. 10 is a flow diagram of the method 350 of determining vault parameters performed by the System Controller 190. In first block 360, the System Controller 190 obtains a dry vault volume of the vault 112. For example, the System Controller 190 may estimate the dry vault volume by multiplying a vault length by a vault width and a vault height. The System Controller 190 may add a chimney volume, if present, to the dry vault volume. If the chimney is generally cylindrical in shape and has a height "h" and a radius "r," the chimney volume may be calculated as the volume of a cylinder, which may be calculated with the formula $h*\pi r^2$. The System Controller 190 may subtract an equipment volume of the equipment 119 (e.g., cables, transformers, components, etc.), if present, from the dry vault volume. If water is in the vault 112, the System Controller 190 may subtract a volume of water from the dry vault volume.

In block 370, the System Controller 190 obtains atmospheric pressure $P_{atm}$. For example, the System Controller 190 may assume isobaric conditions and use an atmospheric pressure obtained from weather data, an atmospheric pressure obtained from one or more of the sensor(s) 128, or use 14.696 pounds per square inch, absolute ("psia") as the atmospheric pressure.

In block 380, the System Controller 190 obtains parameter values to use when determining a water vapor saturation pressure value with sufficient accuracy between 0° C. and 373° C. using a method described by W. Wagner and A. Pruß, "The IAPWS Formulation 1995 for the Thermodynamic Properties of Ordinary Water Substance for General and Scientific Use," *Journal of Physical and Chemical Reference Data*, June 2002, Volume 31, Issue 2, pp. 387535 (copy available at https://www.vaisala.com/sites/default/files/documents/Humidity_Conversion_Formulas_B210973EN-F.pdf).

The parameters values obtained in block 380 may include values for parameters "A," "n," and "$T_n$." The values of these parameters vary depending upon temperature. The parameter "A" may equal a first constant (e.g., 6.089613) if the temperature is less than 0° C. The parameter "A" may equal a second constant (e.g., 6.116441) if the temperature is greater than or equal to 0° C. and less than 50° C. Otherwise, the parameter "A" may equal a third constant (e.g., 6.004918). Similarly, the parameter "n" may equal a first constant (e.g., 9.7787073) if the temperature is less than 0° C. The parameter "n" may equal a second constant (e.g., 7.591386) if the temperature is greater than or equal to 0° C. and less than 50° C. Otherwise, the parameter "n" may equal a third constant (e.g., 7.337936). Additionally, the parameter "$T_n$" may equal a first constant (e.g., 273.1466) if the temperature is less than 0° C. The parameter "$T_n$" may equal a second constant (e.g., 240.7263) if the temperature is greater than or equal to 0° C. and less than 50° C. Otherwise, the parameter "$T_n$" may equal a third constant (e.g., 229.3975). These values are summarized in Table E below.

TABLE E

| Parameter | Temp < 0 | 0 <= Temp < 50 | 50 >= Temp |
|---|---|---|---|
| A | 6.089613 | 6.116441 | 6.004918 |
| n | 9.7787073 | 7.591386 | 7.337936 |
| $T_n$ | 273.1466 | 240.7263 | 229.3975 |

In block 390, the System Controller 190 obtains molecular weights for use in calculations. For example, the System Controller 190 may obtain a molecular weight MWFS for a potential fuel source (e.g., one or more polymers used to construct cable insulation) that may burn in the connection(s) 118A-118J. By way of additional non-limiting examples, the System Controller 190 may obtain a molecular weight for each of components shown in the leftmost columns of Tables B-D.

Then, the method 350 terminates.

Figure 11:
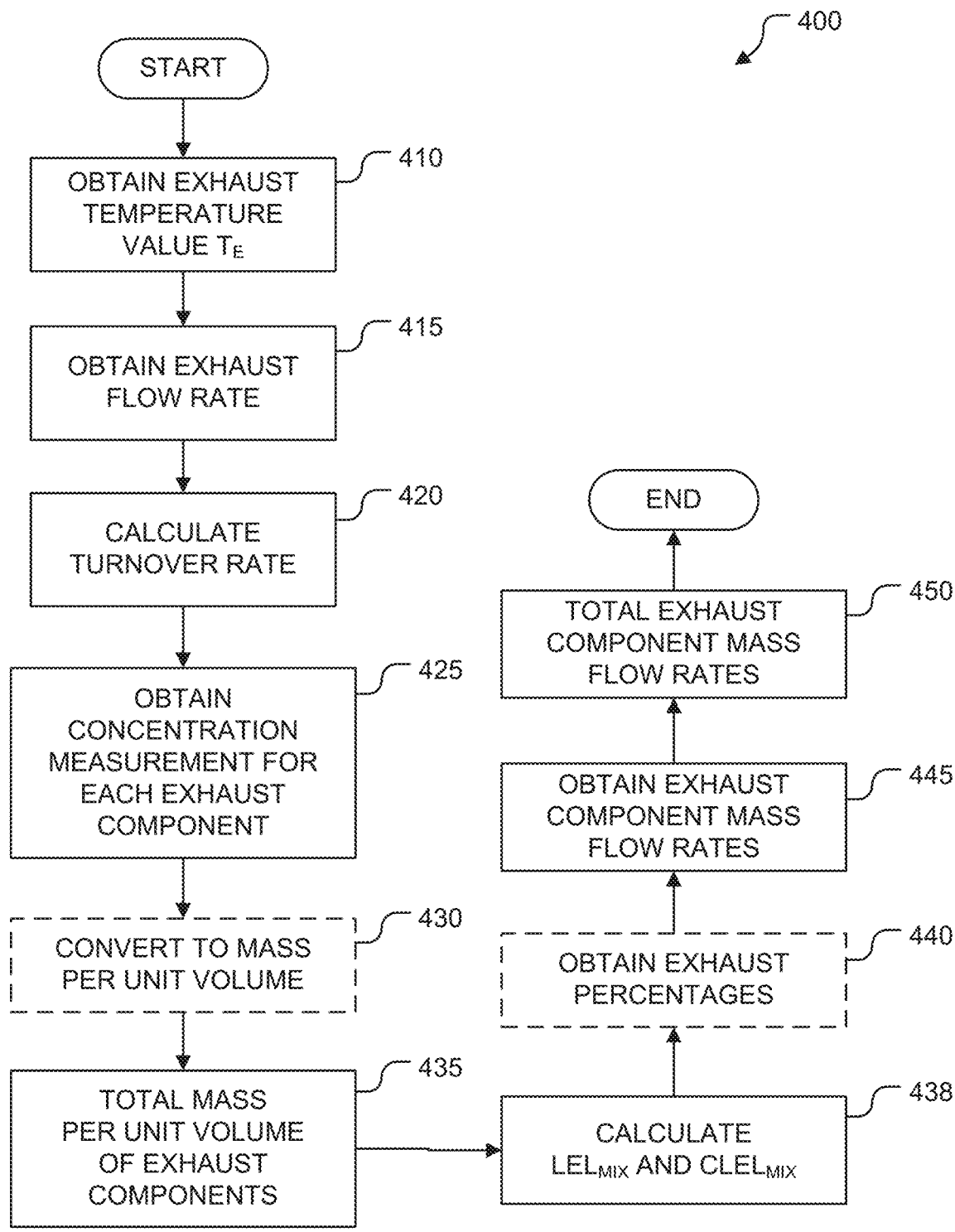
FIG. 11 is a flow diagram of a fourth method performed by the System Controller of FIG. 1.

FIG. 11 is a flow diagram of the method 400 of determining flow parameters for the exhaust flow $F_E$ that may be performed by the System Controller 190.

In first block 410, the System Controller 190 obtains an exhaust temperature value $T_E$ for the exhaust flow $F_E$ from one or more of the fire detection sensor(s) 216 (see FIG. 3).

In block 415, the System Controller 190 obtains a volumetric exhaust flow rate for the exhaust flow $F_E$. For example, the System Controller 190 may obtain the volumetric exhaust flow rate from the manhole event suppression system 140. For example, the System Controller 190 may empirically correlate current drawn by the air moving device 132 to a volumetric exhaust flow rate. If the air moving device 132 is implemented as a rotary fan, the System Controller 190 may empirically correlate revolution-per-minute ("RPM") of the fan and/or current drawn by the fan to the volumetric exhaust flow rate. By way other non-limiting examples, the System Controller 190 may obtain the volumetric exhaust flow rate from one or more of the fire detection sensor(s) 216 (see FIG. 3) configured to measure volumetric flow and/or air velocity in the first section P1 of the ventilation pipe 148.

In block 420, the System Controller 190 calculates a turnover rate. The turnover rate is the vault volume divided by the volumetric exhaust flow rate In block 425, the System Controller 190 obtains a concentration measurement for each of a plurality of exhaust components that may be present in the exhaust flow $F_E$. Exemplary exhaust components are listed in the left-most column of Table B (above) and exemplary exhaust concentration measurements are provided in the second column labeled "Volume" of Table B.

The System Controller 190 may obtain concentrations of oxygen, carbon dioxide, carbon monoxide, and the volatile organic compounds in the exhaust flow $F_E$ from one or more of the fire detection sensor(s) 216 (see FIG. 3). The System Controller 190 may obtain concentrations of hydrogen sulfide and/or sulfur dioxide from one or more of the fire detection sensor(s) 216 (see FIG. 3) or assume each has a concentration of zero. The System Controller 190 may obtain concentrations of nitric oxide, nitrogen dioxide, and/or ozone from one or more of the fire detection sensor(s) 216 (see FIG. 3), assume each has a concentration of zero, or assume each has a concentration equal to an amount of pollution provided by a third party. Optionally, the concentrations of nitric oxide and/or nitrogen dioxide may be obtained by measuring a concentration of NOx.

The System Controller 190 may obtain the concentration of hydrogen in the exhaust flow $F_E$ from the fire detection sensor(s) 216 or estimate the concentration of hydrogen from the concentrations of carbon dioxide ($CO_2$) and carbon monoxide (CO) according to Equation 12 below:

$$H_2 = a \cdot CO + b \cdot CO_2 \tag{12}$$

In Equation 12, the concentrations of carbon dioxide ($CO_2$) and carbon monoxide (CO) may be equal to their respective amounts present in the fresh air. The variable "a" may equal 1.77 and the variable "b" may equal 0, which were determined from experimental data.

The System Controller 190 may obtain the concentration of nitrogen in the exhaust flow $F_E$ by subtracting the concentrations of all other exhaust components, expressed as a percentage, from 100%. The System Controller 190 may obtain the concentration of particulates and aerosols in the exhaust flow $F_E$ from one or more of the fire detection sensor(s) 216 (see FIG. 3) and apportion between soot and ash (e.g., based upon the fire type). If there is no fire, these values can be ignored.

The System Controller 190 may obtain a relative humidity from one or more of the sensor(s) 128 and use it to determine a concentration of water vapor in the exhaust flow $F_E$. To determine the concentration of water vapor, the System Controller 190 may calculate a water vapor saturation pressure "$Pws_E$" for the exhaust flow $F_E$ using Equation 13 below:

$$Pws_E = A * 10^{((m*TE)/(TE+Tn))} \tag{13}$$

In Equation 13 above, the values of the parameters "A," "m," and "$T_n$" are taken from Table E for the exhaust temperature value $T_E$. Then, the System Controller 190 may calculate a water vapor pressure $Pw_E$ for the exhaust flow $F_E$ using Equation 14 below:

$$Pw_E = Pws_E * RH * 100 \tag{14}$$

Next, the System Controller 190 may calculate a water density $WD_E$ (e.g., in g/m$^3$) using Equation 15 below:

$$WD_E = 2.16679 * Pw_E / (T_E + 273.15) \tag{15}$$

Finally, the System Controller 190 may calculate the water vapor concentration (e.g., ppm) for the exhaust flow $F_E$ using Equation 16 below.

$$W_E = 1,000,000 * (WD_E / MWW) * 0.00008205745 * (T_E + 273.15) / P_{atm} \tag{16}$$

In Equation 16 above, a variable MWW is the molecular weight of water and the variable "$P_{atm}$" is atmospheric pressure (measured in atmospheres).

In optional block 430, if the exhaust components are not expressed in mass per unit volume (e.g., g/m$^3$), the System Controller 190 converts them. For example, if the concentrations of the exhaust components are expressed as volume-percent at absolute pressure, the System Controller 190 may convert them to moles per unit volume (see fourth column of Table B) using the exhaust temperature value $T_E$ and the ideal gas law. Then, the System Controller 190 may use the molecular weight of each component to convert the moles per unit volume to mass per unit volume (see fifth column of Table B). By way of a non-limiting example, the mass may be expressed as grams ("g") and the unit volume may be a cubic meter ($m^3$) shown in the fifth column of Table B).

In block 435, the System Controller 190 totals the exhaust components (e.g., expressed in $g/m^3$) to obtain an exhaust total (see last row of fifth column of Table B).

In block 438, the System Controller 190 may utilize the component volume and molar flow rates to calculate mixture lower explosive limits (i.e., $LEL_{mix}$) and mixture corrected lower explosive limits (i.e., $CLEL_{mix}$).

In optional block 440, the System Controller 190 may divide the mass per unit volume of each of the exhaust components by the exhaust total to obtain exhaust percentages.

In block 445, the System Controller 190 multiplies the mass per unit volume of each of the exhaust components (e.g., expressed in $g/m^3$) by the exhaust flow rate (expressed in $m^3/s$) to obtain exhaust component mass flow rates (e.g., g/s) shown in the rightmost column of Table B.

In block 450, the System Controller 190 totals the exhaust component mass flow rates to obtain a total exhaust component flow rate (e.g., g/s) shown in last row of rightmost column of Table B.

Then, the method 400 terminates.

Figure 12:
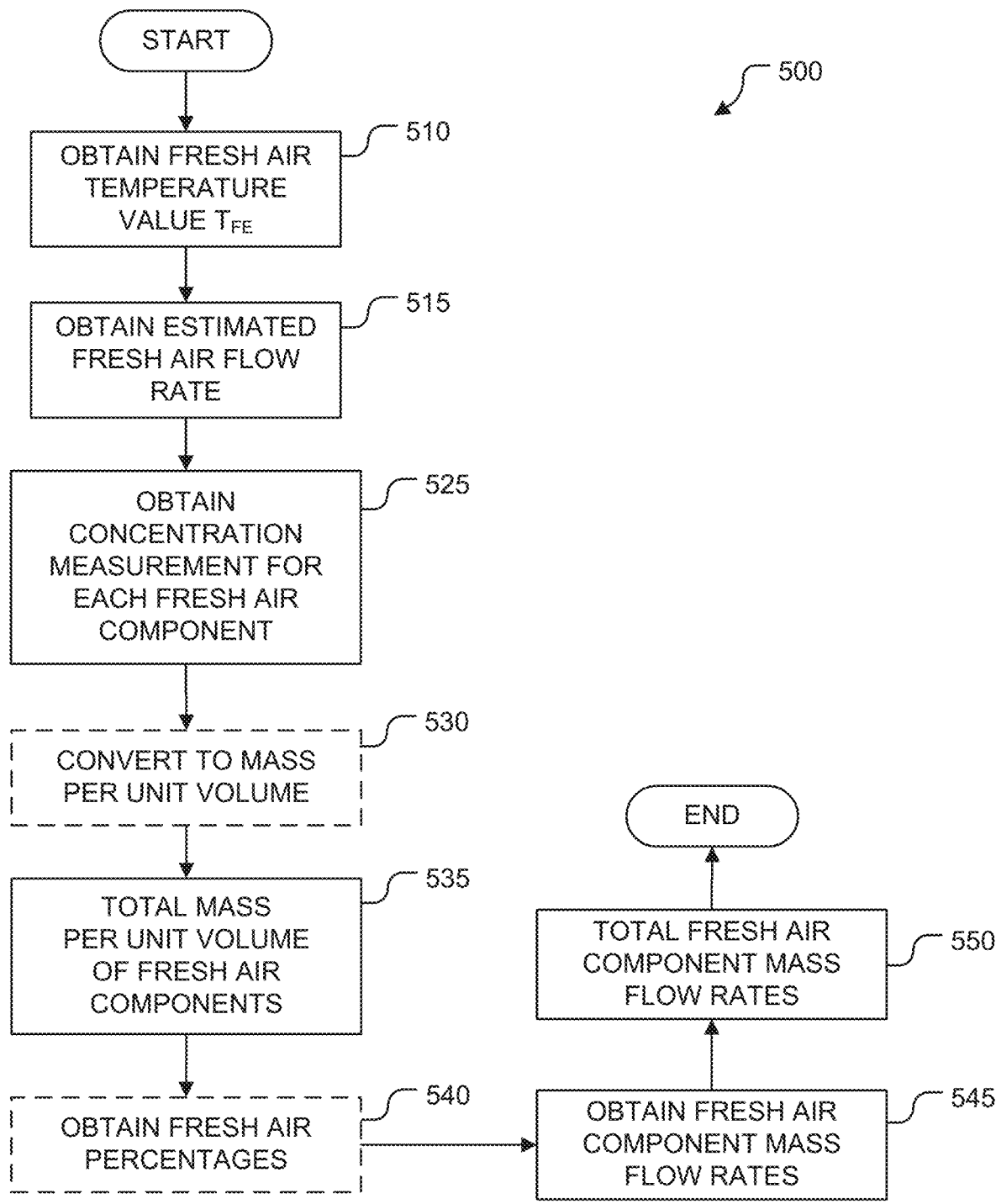
FIG. 12 is a flow diagram of a fifth method performed by the System Controller of FIG. 1.

FIG. 12 is a flow diagram of the method 500 of determining flow parameters for the fresh air flow $F_{FA}$ that may be performed by the System Controller 190.

In first block 510, the System Controller 190 obtains a fresh air temperature value TFA from one or more of the fire detection sensor(s) 216 (see FIG. 3) and/or real-time weather data.

In block 515, the System Controller 190 obtains an estimated fresh air flow rate for the fresh air flow $F_{FA}$. As mentioned above, the System Controller 190 may adjust the fresh air flow rate until the mass balance error value is zero.

In block 525, the System Controller 190 obtains a concentration measurement for each of a plurality of fresh air components that may be present in the fresh air flow $F_{FA}$. Exemplary fresh air components are listed in the left-most column of Table C (above) and exemplary fresh air concentration measurements are provided in the second column labeled "Volume" of Table B.

The System Controller 190 may obtain the concentration of oxygen ($O_2$) in the fresh air flow $F_{FA}$ from one or more of the fire detection sensor(s) 216 (see FIG. 3), from a third party data source, and/or use a typical tropospheric level adjusted for known variations of non-nitrogen, non-oxygen components. For example, the System Controller 190 may express the fresh air components as a percentage of the fresh air flow $F_{FA}$, subtract all components that are not nitrogen or oxygen from 100%, and multiply the difference by a percentage of oxygen that is typical in the troposphere.

The System Controller 190 may obtain the concentration of carbon dioxide ($CO_2$) in the fresh air flow $F_{FA}$ from one or more of the fire detection sensor(s) 216 (see FIG. 3), from a third party data source, and/or use a typical tropospheric level adjusted for known variations of non-nitrogen, non-oxygen components.

The System Controller 190 may obtain the concentration of carbon monoxide (CO) in the fresh air flow $F_{FA}$ from one or more of the fire detection sensor(s) 216 (see FIG. 3), from a third party data source, and/or use a typical local level.

The System Controller 190 obtains the relative humidity "RH" of the fresh air flow $F_{FA}$ from one or more of the fire detection sensor(s) 216 (see FIG. 3), from a third party data source, and/or use a typical seasonal and/or local level. The System Controller 190 uses the relative humidity "RH" of the fresh air flow $F_{FA}$ to calculate the water vapor concentration (e.g., ppm). To do so, the System Controller 190 may calculate a water vapor saturation pressure "$Pws_{FA}$" for the fresh air flow $F_{FA}$ using Equation 17 below:

$$Pws_{FA}=A*10^{((m*TFA)/(TFA+Tn))} \quad (17)$$

In Equation 17 above, the values of the parameters "A," "m," and "$T_n$" are taken from Table E for the fresh air temperature value $T_{FA}$. Then, the System Controller 190 may calculate a water vapor pressure $Pw_{FA}$ for the fresh air flow $F_{FA}$ using Equation 18 below:

$$Pw_{FA}=Pws_{FA}*RH*100 \quad (18)$$

Next, the System Controller 190 may calculate a water density $WD_{FA}$ (e.g., in $g/m^3$) using Equation 19 below:

$$WD_{FA}=2.16679*Pw_{FA}/(T_{FA}+273.15) \quad (19)$$

Finally, the System Controller 190 may calculate the water vapor concentration (e.g., ppm) for the fresh air flow $F_{FA}$ using Equation 20 below.

$$W_{FA}=1{,}000{,}000*(WD_{FA}/MWW)*0.00008205745*(T_{FA}+273.15)/P_{atm} \quad (20)$$

In Equation 20 above, the variable MWW is the molecular weight of water and the variable "$P_{atm}$" is atmospheric pressure (measured in atmospheres).

The System Controller 190 may obtain the concentration of each of hydrogen sulfide, sulfur dioxide, VOCs, nitric oxide, nitrogen dioxide, and ozone in the fresh air flow $F_{FA}$ from one or more of the fire detection sensor(s) 216 (see FIG. 3), from a third party data source, or assume the concentration is zero.

The System Controller 190 may assume the concentration of hydrogen ($H_2$) in the fresh air flow $F_{FA}$ is zero.

The System Controller 190 may estimate the concentration of nitrogen using the typical tropospheric level adjusted for known variations of non-nitrogen, non-oxygen components. For example, the System Controller 190 may express the fresh air components as a percentage of the fresh air flow $F_{FA}$, subtract all components that are not nitrogen or oxygen from 100%, and multiply the difference by a percentage of nitrogen that is typical in the troposphere.

The System Controller 190 may obtain the concentration of soot (or particulates) in the fresh air flow $F_{FA}$ from one or more of the fire detection sensor(s) 216 (see FIG. 3) and/or a third party data source (e.g., pollution data).

The System Controller 190 may assume the concentration of ash in the fresh air flow $F_{FA}$ is zero.

In optional block 530, if the fresh air components are not expressed in mass per unit volume (e.g., $g/m^3$), the System Controller 190 converts them. For example, if the concentrations of the fresh air components are expressed as volume-percent at absolute pressure, the System Controller 190 may convert them to moles per unit volume (see fourth column of Table C) using the fresh air temperature value $T_E$ and the ideal gas law. Then, the System Controller 190 may use the molecular weight of each component to convert the moles per unit volume to mass per unit volume (see fifth column of Table C). By way of a non-limiting example, the mass may be expressed as grams ("g") and the unit volume may be a cubic meter ($m^3$) shown in the fifth column of Table C).

In block 535, the System Controller 190 totals the mass per unit volume of the fresh air components (e.g., expressed in $g/m^3$) to obtain a fresh air total (see last row of fifth column of Table C).

In optional block 540, the System Controller 190 may divide the mass per unit volume of each of the fresh air components by the fresh air total to obtain fresh air percentages.

In block 545, the System Controller 190 multiplies the mass per unit volume of each of the fresh air components (e.g., expressed in g/m$^3$) by the fresh air flow rate (expressed in m$^3$/s) to obtain fresh air component mass flow rates (e.g., g/s) shown in the rightmost column of Table C.

In block 550, the System Controller 190 totals the fresh air component mass flow rates to obtain a total fresh air component flow rate (e.g., g/s) shown in last row of rightmost column of Table C.

Then, the method 500 terminates.

If there is no fire in the system 100 (see FIG. 1), the concentrations (shown in the second column of Table B) of each of the exhaust components are equal to the concentrations (shown in the second column of Table C) of the fresh air components. However, if a fire is present, these concentrations will not be equal. In other words, the evaporation flow $F_V$ and/or the connection(s) flow $F_C$ is/are contributing to the exhaust flow $F_E$.

Figure 13:
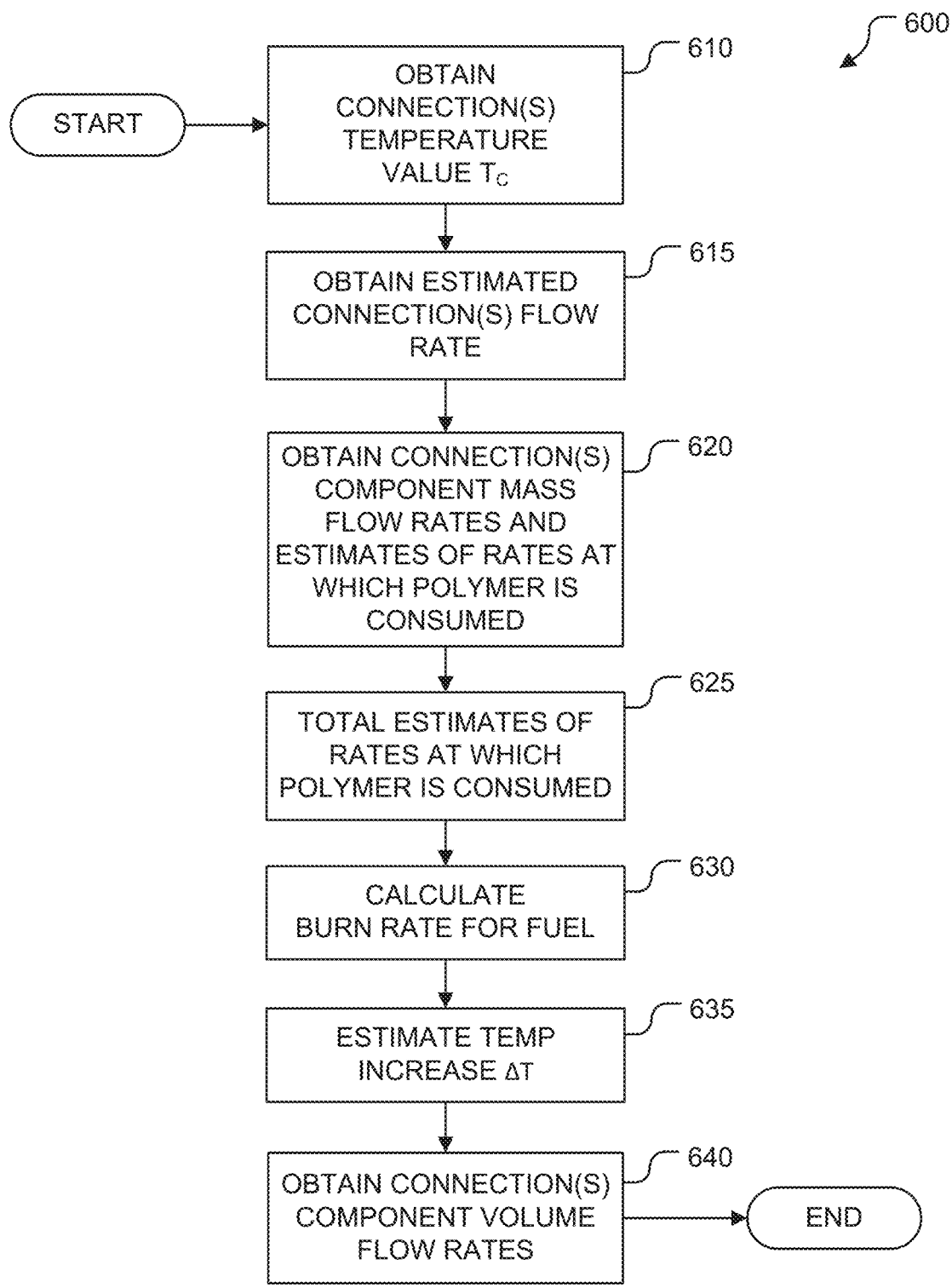
FIG. 13 is a flow diagram of a sixth method performed by the System Controller of FIG. 1.

FIG. 13 is a flow diagram of the method 600 of determining flow parameters for the connection(s) flow $F_C$ that may be performed by the System Controller 190 (e.g., when these concentrations are not equal).

In first block 610, the System Controller 190 obtains a connection(s) temperature value Tc. The System Controller 190 may obtain the connection(s) temperature value Tc from one or more of the fire detection sensor(s) 216 (e.g., a thermistor, an infrared sensor, and the like). Alternatively, the System Controller 190 may estimate the connection(s) temperature value Tc from cable load data and/or heat of combustion, when present. By way of another non-limiting example, the System Controller 190 may assume the connection(s) temperature value Tc is the same as the exhaust temperature value $T_E$.

In block 615, the System Controller 190 obtains an estimated connection flow rate for the connection(s) flow $F_C$. As mentioned above, the System Controller 190 determines the connection(s) flow rate by adjusting the fresh air flow rate until the mass balance error value is zero.

In block 620, the System Controller 190 estimates component mass flow rates (shown in the fourth column of Table D above) for at least some of the connection(s) components. For example, the component mass flow rates of the carbon dioxide ($CO_2$), carbon monoxide (CO), hydrogen ($H_2$), sulfur dioxide ($SO_2$), VOCs, nitric oxide (NO), nitrogen dioxide ($NO_2$), ozone ($O_3$), Soot, and ash may be obtained by subtracting their respective component mass flow rates in the fresh air flow $F_{FA}$ from their respective component mass flow rates in the exhaust flow $F_E$.

The System Controller 190 may use the component mass flow rate of carbon dioxide to estimate a first ($CO_2$ based) rate at which moles of a polymer consumed (shown in in the third row of the rightmost column of Table D above). Oxidative decomposition of a single repeating polymer unit yields a single molecule of carbon dioxide. Therefore, the first ($CO_2$ based) rate (e.g., expressed as moles/second) at which the polymer consumed by oxidative decomposition is approximately equal to the component mass flow rate of carbon dioxide divided by the molecular weight of carbon dioxide.

The System Controller 190 may use the component mass flow rate of carbon monoxide to estimate a second (CO based) rate at which moles of a polymer consumed (shown in the fourth row of the rightmost column of Table D above). Oxidative decomposition (with insufficient oxygen for complete combustion) of a single repeating polymer unit yields a single molecule of carbon monoxide. Thus, the second (CO based) rate (e.g., expressed as moles/second) at which the polymer consumed by oxidative decomposition is approximately equal to the component mass flow rate of carbon monoxide divided by the molecular weight of carbon monoxide.

Hydrogen is a pyrolysis product of polymers. If hydrogen is present in the exhaust flow $F_E$, the hydrogen likely came from pyrolysis.

Sulfur dioxide is a combustion product of hydrogen sulfide or sulfur used as curing agents or anti-oxidants in polymers. If any sulfur dioxide is present in the exhaust flow $F_E$, the sulfur dioxide likely came from combustion. Where hydrogen sulfide gas is ubiquitous, sulfur dioxide will accompany most combustion events. The System Controller 190 may ignore the sulfur dioxide because sulfur concentration is low in polymers.

The System Controller 190 may assume the VOCs are methane ($CH_4$). If refined measurements are available for other hydrocarbons, the System Controller 190 may refine the analysis using the same method. The System Controller 190 may use the component mass flow rate of VOCs to estimate a third ($CH_4$ based) rate at which moles of a polymer consumed (shown in the eighth row of the rightmost column of Table D above). Burning a single repeating polymer unit yields a single molecule of methane. Therefore, the third ($CH_4$ based) rate (e.g., expressed as moles/second) is approximately equal to the component mass flow rate of VOCs divided by the molecular weight of methane.

Nitric oxide is formed as a result of many combustion events and is particularly prevalent where plasmatization occurs and hence is a marker for electrical arcing. It is not useful directly to estimate burn rate.

Nitrogen dioxide is formed as a result of many combustion events and is particularly prevalent where plasmatization occurs. Therefore, nitrogen dioxide is a marker for electrical arcing but is not useful directly to estimate burn rate.

Ozone is formed as a result of many combustion events and is particularly prevalent where plasmatization occurs. Therefore, ozone is a marker for electrical arcing but is not useful directly to estimate burn rate.

Soot may be primarily carbon. A portion of soot is deposited on surfaces or settles and may not be measured in the exhaust flow $F_E$. The System Controller 190 may ignore such carbon. Alternatively, the System Controller 190 may use the component mass flow rate of soot to estimate a fourth (soot based) rate at which moles of a polymer consumed (shown in the fourteenth row of the rightmost column of Table D above). The fourth (soot based) rate (e.g., expressed as moles/second) is approximately equal to the component mass flow rate of soot divided by the molecular weight of carbon.

Ash may be primarily silicon dioxide.

Much of the water vapor produced as a result of combustion condenses. When the hot combustion products, including water vapor, enter the vault 112, they cool to the temperature of the vault 112 and condense into liquid water. The System Controller 190 ignores this liquid water. Therefore, the relative humidity RH is assumed to be 100% at the exhaust temperature value $T_E$.

The System Controller 190 uses the relative humidity "RH" of the connection(s) flow $F_C$ to calculate the water vapor concentration (e.g., % of mass). To do so, the System Controller 190 may calculate a water vapor saturation pressure "$Pws_C$" for the connection(s) flow $F_C$ using Equation 21 below:

$$Pws_C = A*10^{((m*TE)/(TE+Tn))} \quad (21)$$

In Equation 21 above, the values of the parameters "A," "m," and "$T_n$" are taken from Table E for the exhaust temperature value $T_E$. Then, the System Controller 190 may calculate a water vapor pressure $Pw_C$ for the connection(s) flow $F_C$ using Equation 22 below:

$$Pw_c = Pws_C*RH*100 \quad (22)$$

In Equation 22 above, the relative humidity RH is one. Next, the System Controller 190 may calculate a water density $WD_c$ (e.g., in g/m$^3$) using Equation 23 below:

$$WD_c = 2.16679*Pw_c/(T_E+273.15) \quad (23)$$

Finally, the System Controller 190 may calculate the water vapor concentration (e.g., % of mass) for the connection(s) flow $F_C$ using Equation 24 below.

$$W_c = (WD_c/MWW)*0.00008205745*(T_E+273.15)/P_{atm} \quad (24)$$

In Equation 24 above, the variable MWW is the molecular weight of water and the variable "$P_{atm}$" is atmospheric pressure (measured in atmospheres).

Then, the System Controller 190 may calculate the component mass flow rate of the water vapor based on the water vapor concentration.

The component mass flow rate of the oxygen ($O_2$) may be calculated based on the component mass flow rates of the nitrogen ($N_2$), carbon dioxide, hydrogen, and carbon monoxide. Much available oxygen is consumed by oxidative decomposition. However, no combustion is perfect and some oxygen will always remain. To estimate the component mass flow rate of oxygen ($O_2$) the System Controller 190 may multiply the component mass flow rate of nitrogen by both first and second values. The first value is atmospheric $O_2$ divided by atmospheric $N_2$ (e.g., 20.95/78.09). The second value is the component mass flow rate of carbon monoxide (e.g., expressed in moles per second) divided by the component mass flow rate of carbon dioxide (e.g., expressed in moles per second), one is added to this quotient, and the sum is divided by two. Ample carbon dioxide indicates a sufficient supply of oxygen to support oxidative decomposition. The presence of ample carbon monoxide indicates a dearth of oxygen.

The component mass flow rate of the hydrogen ($H_2$) may be measured by the fire detection sensor(s) 216 or calculated based on the component mass flow rates of the carbon dioxide and carbon monoxide. In oxygen rich aerobic environments, hydrogen evolution is close to zero. During high temperature anaerobic pyrolysis, all of the hydrogen atoms in a polymer are converted to hydrogen gas. Most manhole events fall between these two extremes. The System Controller 190 may calculate the component mass flow rate of the hydrogen ($H_2$) using an aerobic estimate (e.g., about 1.770834) and an anaerobic estimate (0). Then the System Controller 190 multiplies the anaerobic estimate by the first ($CO_2$ based) rate and adds this value to the aerobic estimate multiplied by the second (CO based) rate. Next, the System Controller 190 multiplies this value by the molecular weight of hydrogen ($H_2$) to obtain the component mass flow rate of the hydrogen ($H_2$).

The component mass flow rate of the nitrogen ($N_2$) may be calculated based on the component mass flow rates of the carbon dioxide, carbon monoxide, nitric oxide (NO), and nitrogen dioxide ($NO_2$). Each mole of $CO_2$ and each two moles of CO entrain 3.727 moles of $N_2$. Thus, the System Controller 190 obtains a first value by adding the first ($CO_2$ based) rate to the second (CO based) rate divided by two. NO and $NO_2$ consume nitrogen in ratios of 1:1 and 1:2, respectively. Thus, the System Controller 190 obtains second and third values. The second value is obtained by subtracting from the first value the component mass flow rate of the nitric oxide (NO) multiplied by the molecular weight of the nitric oxide (NO). The third value is obtained by subtracting from the second value the component mass flow rate of the nitrogen dioxide ($NO_2$) multiplied by the molecular weight of the nitrogen dioxide ($NO_2$) and divided by two. Oxidative decomposition entrains nitrogen with oxygen ($N_2/O_2$) in a volume and molar proportion of 78.09/20.95, respectively. Thus, the System Controller 190 obtains the component mass flow rate of the nitrogen ($N_2$) by multiplying the third value by 78.09/20.95 and the molecular weight of nitrogen ($N_2$).

In block 625, the System Controller 190 obtains a consumption rate by totaling the first ($CO_2$ based), second (CO based), third ($CH_4$ based), and fourth (soot based) rates at which the polymer is consumed.

In block 630, the System Controller 190 estimates a burn rate for the potential fuel source. The System Controller 190 may calculate the burn rate by multiplying the consumption rate by the molecular weight MWFS (e.g., about 14.03) of the potential fuel source. The burn rate may be expressed in grams per minute or second. The burn rate estimated in block 630 may be used as the burn rate in block 242-K (see FIG. 7K) of the calculate method 200-K (see FIG. 7K). Alternatively, where there is no fire, the burn rate estimated in block 630 may be used as the FGA in block 206-K (see FIG. 7K).

In block 635, the System Controller 190 obtains an estimated temperature increase "ΔT" caused by the burn components reaching the vault 112. For example, the System Controller 190 may obtain the estimated temperature increase from one or more of the fire detection sensor(s) 216 (see FIG. 3). The estimated temperature increase "ΔT" represents a temperature increase above the vault ambient temperature and is required to apply the ideal gas law to the connection(s) flow $F_C$ to complete a robust energy balance.

In block 640, the System Controller 190 may convert the component mass flow rates (e.g., grams per second) to component volume flow rates (cubic meters per second) for each of the connection(s) components. Exemplary component volume flow rates are provided in the second column of Table D above.

Then, the method 600 terminates.

Figure 14:
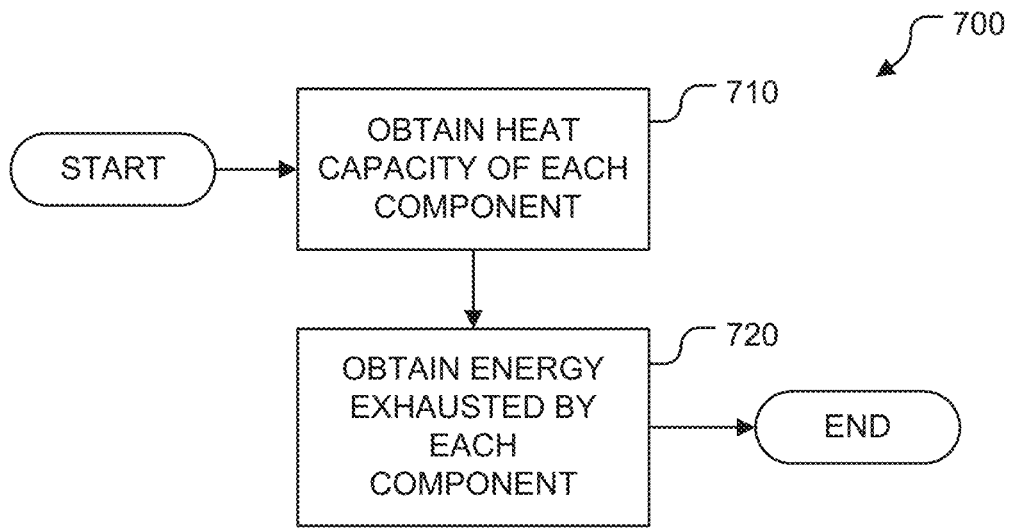
FIG. 14 is a flow diagram of a seventh method performed by the System Controller of FIG. 1.

FIG. 14 is a flow diagram of the method 700 of performing the energy balance. In first block 710, the System Controller 190 obtains a heat capacity (e.g., expressed as joules per gram·° K) for each of the exhaust components (see leftmost column of Table B). The heat capacity for each of the exhaust components may be found in relevant literature.

In next block 720, the System Controller 190 calculates the energy exhausted "Δh" (BTU/min or J/s) by each component. To do so, the System Controller 190 calculates the first exhaust value "$h_e$" by multiplying the heat capacity of the exhaust component by both the component mass flow rate of the exhaust component and absolute temperature (e.g., the exhaust temperature value $T_E$+459.67). Then, the System Controller 190 calculates, for each fresh air component, the second fresh air value "$h_f$" by multiplying the heat capacity of the fresh air component by both the component mass flow rate of the fresh air component and absolute temperature (e.g., the fresh air temperature value $T_{FA}$ 459.67). Next, the System Controller 190 calculates, for each connection(s) component, the third connection(s) value "$h_c$" by multiplying the heat capacity of the connection(s) component by both the component mass flow rate of the connection(s) component and absolute temperature estimated above (e.g., the connection(s) temperature value $T_C$+459.67). Finally, for each component, the System Controller 190 subtracts both the third connection(s) value and the second fresh air value "$h_f$" from the first exhaust value "$h_e$" to obtain the energy exhausted "$\Delta h$" for the component. In other words, for each component, the energy exhausted "$\Delta h$" equals the first exhaust value "$h_e$" minus both the fresh air value "$h_f$" and the third connection(s) value "$h_c$".

Then, the method 700 terminates.

Figure 15:
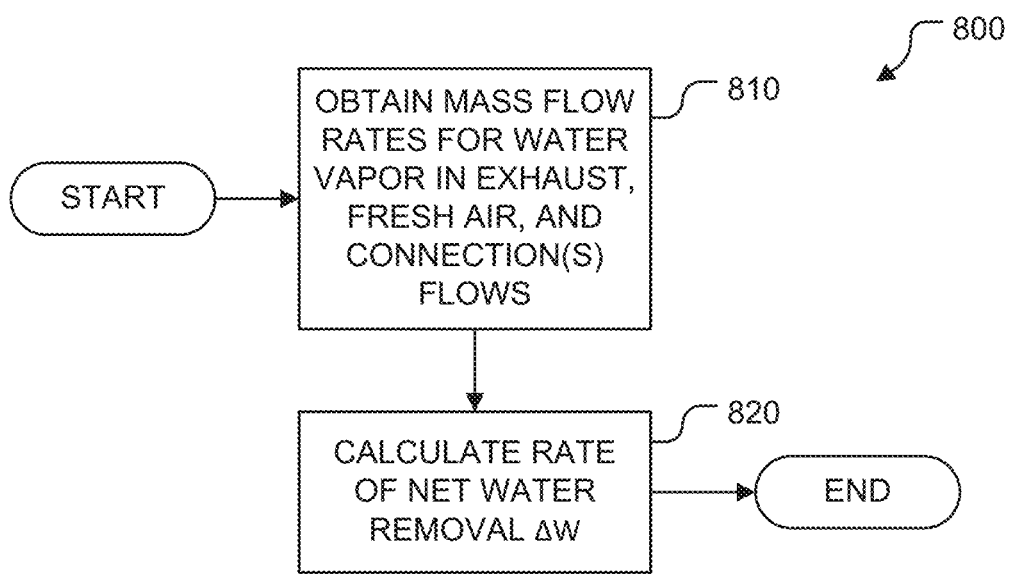
FIG. 15 is a flow diagram of an eighth method performed by the System Controller of FIG. 1.

FIG. 15 is a flow diagram of the method 800 of calculating a rate of net water removal "$\Delta w$" from the vault 112. It is desirable to keep water out of the vault 112. When the vault 112 does not experience tidal inflows and outflows of water, water can depart the vault 112 in four ways: (a) leak/diffuse through the concrete, (b) flow out through one or more conduits connected to the vault 112, (c) evaporate and be carried into the external atmosphere 122 by the manhole event suppression system 140, and (d) be pumped out by the vault owner. Depending upon the implementation details, the System Controller 190 may not able to determine an amount of the water being pumped from the vault 112 because doing so generally requires the removal of the manhole cover 144.

However, the System Controller 190 may utilize the method 800 to calculate an amount of the water leaving the vault 112 by evaporation in the evaporation flow $F_V$. In first block 810, the System Controller 190 obtains the component mass flow rate "we" of water vapor (see fifth row of rightmost column of Table B above) in the exhaust flow $F_E$, the component mass flow rate "$w_f$" of water vapor (see fifth row of rightmost column of Table C above) in the fresh air flow $F_{FA}$, and the component mass flow rate "we" of water vapor (see fifth row of fourth column of Table B above) in the connection(s) flow $F_C$.

Then, in block 820, the System Controller 190 calculates the rate of net water removal "$\Delta w$" by subtracting the component mass flow rate "$w_f$" and the component mass flow rate "we" from the component mass flow rate "we." Active ventilation evaporates a great deal of water and transports that water out of the vault 112 and into the atmosphere. By way of non-limiting examples, the System Controller 190 may calculate the rate of net water removal "$\Delta w$" in g/min, liter/hr, and/or liter/day.

Then, the method 800 terminates.

The water level sensor 214 may be used to determine a depth of the water present on the floor 168 of the vault 112. In periods when there is no precipitation, any decrease in the depth of the water beyond that attributable to the evaporation flow $F_V$ of evaporating water is caused by water leaking/diffusing through the concrete and/or flowing out through the conduit(s) connected to the vault 112. The component mass flow rate "we" may be a combination of water leaking/diffusing through the concrete and/or flowing out through the conduit(s) connected to the vault 112. If the System Controller 190 knows the height of connections 118A-118J, the System Controller 190 can calculate how much of the decrease in the depth of the water was caused by water leaking/diffusing through the concrete and water flowing out through the conduit(s) connected to the vault 112. For example, the amount of water leaking/diffusing through the concrete may be empirically modeled with seasonal considerations. Also, visual or infrared cameras may be used to observe water flowing through the conduit(s), and, where it is significant, the System Controller 190 may use this information to estimate an amount of water flowing out through the conduit(s) connected to the vault 112.

On the other side of the coin, the depth of the water can only increase by one of four analogous mechanisms: (A) leak/diffuse through concrete, (B) flow in from conduit(s), (C) flow through the manhole cover when there is precipitation or (D) human induced irrigation. Human induced irrigation may occur, for example, when city employees wish to enter a storm drain to conduct maintenance and pump water from the storm drain onto city streets. The water pumped from the storm drain flows down the street and enters the vault 112. The System Controller 190 may use weather data to determine when precipitation is occurring. During a precipitation event, the System Controller 190 can monitor the increase in the depth of the water associated with the precipitation event and create a model of water ingress by precipitation rate and precipitation type (e.g., rain, snow, etc.). If more water is entering the vault 112 during a precipitation event than is desirable, the vault owner can take steps to reduce this flow, such as checking that installation seals are proper, diverting run-off flow away from the manhole, and the like.

Dry vaults save their owners money. Vault owners have to pump out water before entering their vaults and such water typically has to be disposed of as hazardous waste. Thus, it is desirable to keep the vaults dry as much as possible (e.g., for a greater portion of the year). Additionally, some industries, such as the U.S. nuclear industry, require that plant owners maintain dry vaults.

The System Controller 190 may use the time constant T to extrapolate into the future. For example, if a $CO_2$ concentration sensor is positioned on the north side of the vault 112 and a propane torch with a constant burn rate is ignited on the south side of the vault 112, at time zero, the $CO_2$ concentration sensor has not yet detected any of the $CO_2$ produced by the propane torch. As time progresses, the $CO_2$ concentration sensor detects more and more $CO_2$ produced by the propane torch. The $CO_2$ produced by the propane torch will reach a plateau after some time. The plateau value of the $CO_2$ concentration is an indication of the size of the fire. When the $CO_2$ concentration has reached its plateau value, the System Controller 190 may determine the time constant T based on geometry of the vault 112 and the turnover rate calculated in block 420 (see FIG. 11). The time constant T (tau) is the quotient of the vault volume and the exhaust rate. For well mixed vaults (e.g., where active ventilation is deployed) about 63.2% (i.e. 1-1/e) of a contaminant gas will be removed after one time constant. The turnover rate may be either a rate of dilution of the first type or a predetermined fixed interchange rate. Thus, the System Controller 190 may measure and/or calculate the time constant T using the turnover rate and the geometry of the vault 112. Because the geometry of the vault 112 is constant, the System Controller 190 may associate the time constant T with the turnover rate. The next time the $CO_2$ concentration sensor begins detecting an increase in the $CO_2$ concentration, the System Controller 190 may use the time constant T associated with the current turnover rate in the vault 112 to extrapolate the $CO_2$ concentration detected by the $CO_2$ concentration sensor to its future plateau value. Alternatively, the System Controller 190 may set the rate of dilution of the first type equal to the turnover rate and use the time constant T to extrapolate the $CO_2$ concentration detected by the $CO_2$ concentration sensor to its future plateau value.

As mentioned above, the plateau value of the $CO_2$ concentration indicates the size of the fire. Thus, the System Controller 190 may determine the size of a new propane fire shortly after the $CO_2$ concentration sensor begins detecting an increase, rather than waiting for the asymptote to be approached. In a real fire situation, this means quicker indication of fire magnitude.

Each of the flows $F_E$, OFFA, $F_C$, and $F_V$ include one or more gases. Typically, the exhaust flow $F_E$ will include 02, CO, $CO_2$, $H_2O$, and VOC. The fresh air flow $F_E$ and the connection(s) flow $F_C$ may contribute any of these gases to the exhaust flow $F_E$. However, the evaporation flow $F_V$ may contribute only $H_2O$ and/or VOC to the exhaust flow $F_E$.

The System Controller 190 may obtain concentrations of $O_2$, CO, $CO_2$, $H_2O$, and/or VOC from third-party atmospheric data (e.g., www.aclima.io, which provides almost real time local data), dedicated sensors connected wirelessly or via wired connections to the System Controller 190, or the fire detection sensor(s) 216 (see FIG. 3) where dilution of the second type is available. The System Controller 190 obtain the concentrations of the components of the fresh air flow $F_{F4}$ by using dilution of the second type to supply 100% fresh air to the fire detection sensor(s) 216 (see FIG. 3). Then, the System Controller 190 simply obtains the sensor readings from the fire detection sensor(s) 216 (see FIG. 3) and uses them to determine the concentrations of the components of the fresh air flow $F_{F4}$.

The methods 300, 350, 400, 500, 600, 700, and 800 as well as the equations described above are valid at steady state regardless of the size of the underground vault 112.

In the case of an unventilated environment, sensor drift means that the fire detection sensor(s) 216 (see FIG. 3) cannot be relied upon and the System Controller 190 must make a trade-off between falsely alerting the owner of the underground vault 112 of a condition (a false positive) or setting the alarm level at a dangerously high value and thus failing to alert the owner of a potentially dangerous condition (suffering false negatives). Various statistical methods can be used to optimize the required trade-off between false positives and false negatives. Neither false positives nor false negatives are desirable.

Some of these shortcomings can be overcome by using Calibrationless Operation method 200 described above.

By way of non-limiting examples, any of the following may indicate a fire:
 i. $CO_2$ is elevated;
 ii. CO is elevated;
 iii. VOCs are elevated;
 iv. $H_2O$ (absolute humidity) is elevated;
 v. NO is elevated;
 vi. $NO_2$ is elevated;
 vii. 03 is elevated;
 viii. $SO_2$ is elevated;
 ix. 02 is depressed (dilution by i-iv);
 x. Temperature is elevated;
 xi. Particulates are elevated; and/or
 xii. $H_2$ is elevated.

Another non-limiting example of an alarm state may indicate that flammable vapors are accumulating. By way of non-limiting examples, any of the following conditions may indicate that flammable vapors are accumulating:
 i. CO is elevated;
 ii. $H_2$ is elevated;
 iii. VOCs are elevated; and/or
 iv. $H_2S$ is elevated.

Dilution by the System Controller

The System Controller 190 is configured to use an algorithm, heuristics, human input, and/or artificial intelligence to achieve the desired measurements and to exercise the desired controls. Active and continuous ventilation enjoys benefits beyond the primary purpose of explosion prevention. Non-limiting examples of such benefits include cooling and drying the manhole environment, both of which contribute to improved equipment reliability and life.

The System Controller 190 may control or throttle the exhaust rate over limited periods of time for calibration purposes. The System Controller 190 may calculate the time constants T (for associated turnover rates) for the underground vault 112, the time constants T the manhole event suppression system 140, and the time constants T for the two types of dilution using methods that are well known in the art. Alternatively, the System Controller 190 may empirically deduce these time constants T by throttling (to adjust the dilution of the first type) and by altering the IMR (to adjust the dilution of the second type). Non-limiting examples of such purposeful dilution adjustments follow.

The System Controller 190 may frequently and automatically calibrate the fire detection sensor(s) 216 (see FIG. 3) utilizing one or more of the following three tools:
 1. a source of fresh air from the external atmosphere 122,
 2. the ability to vary a ratio of exhausted air and the fresh air, and
 3. the ability to spike the fresh air with at least one pure calibration gas ("cal-gas").

The fresh air from the external atmosphere 122 may be used to dilute a sample. For example, if an amount of a component gas of interest in a sample (e.g., concentration of the component gas) approaches an upper limit in the sensing range of a sensor, the System Controller 190 may use dilution of the first type and/or the second type to reduce the amount of the component gas of interest in the sample. Conversely, if the amount of the component gas of interest in the sample is at or below a lower limit in the sensing range of the sensor, the System Controller 190 may decrease dilution (at least temporarily) to increase the amount of the component gas of interest in the sample. In this way, the System Controller 190 may use dilution of the first type and/or the second type to ensure the sensor is able to detect the amount of the component gas of interest by keeping the amount of the component gas of interest inside the sensor's sensing range.

If at least one flammable component gas is approaching an amount (e.g., a concentration) that is dangerous (e.g., explosive or poisonous), the System Controller 190 may use dilution of the first type to reduce the amount of the at least one flammable component gas until the maximum exhaust flow rate is realized.

The System Controller 190 may calibrate one of the fire detection sensor(s) 216 (see FIG. 3) by delivering to that sensor any IMR (zero to infinity) of the exhaust flow $F_E$ and fresh air from the exterior atmosphere 122. For example, the fresh air may contain about 21% oxygen. The System Controller 190 may direct the monitor 126 to supply an IMR of zero, which includes 0% exhaust flow and 100% fresh air, to an oxygen concentration sensor. Then, the System Controller 190 may calibrate the oxygen concentration sensor to 21%. Similarly, fresh air typically has about 400 ppm of carbon dioxide. The System Controller 190 may direct the monitor 126 to supply a ratio of zero, which includes 0% exhaust flow and 100% fresh air, to a carbon dioxide concentration sensor. Then, the System Controller 190 may calibrate the carbon dioxide concentration sensor to 400 ppm.

Spiking is best implemented with materials that can be safety contained in liquid form, but are readily vaporized at temperature and pressure conditions found in the underground vault 112 (referred to as Vault Temperature and Pressure or "VTP"). Carbon dioxide, propane, and butane are examples of materials that are safely and easily stored as liquids. Liquid spiking agents are preferred because a large volume of gas can be generated from a relatively small volume of liquid. For example, the ratio of gas volume (standard temperature and pressure or STP) to liquid volume for carbon dioxide is about 390. Other gases of interest as spiking agents may not be easily liquefied and instead can be stored as high-pressure gases. Because a volume ratio of such gaseous spiking agents at VTP and at storage pressure is much less than the volume ratio of liquid spiking agents (e.g., an ideal gas such as oxygen at 2000 psi has a volume ratio of about 136, or roughly one-third of liquid carbon dioxide), these gaseous spiking agents require larger containers, may be utilized less frequently, or must be periodically refilled or swapped.

It is not possible to calibrate a sensor with zero data points. A single data point can be used for offset calibration. The shortcoming of the single point offset calibration is the slope of the response curve may also drift. A multi-point calibration is superior to a single point calibration because it allows adjustment of both the intercept and the slope of the calibration curve. More than two data points improve the calibration further, but with diminishing returns. Non-limiting examples of two-point calibration are provided in Table F (below). The System Controller 190 can calibrate one or more sensors using the information of Table F:

TABLE F

| Gas | Air | Cal-gas |
|---|---|---|
| $CO_2$ | Assume 410 ppm in fresh air or use values reported by air monitoring data suppliers | ~3-4% mixed with fresh air |
| CO | Assume 0 ppm in fresh air or use values reported by air monitoring data suppliers | 2 point calibration: ~150 ppm and ~800 ppm (requires $O_2$ in mixture) |
| $O_2$ | Assume 20,900 ppm in fresh air or use values reported by air monitoring data suppliers | 2 point calibration: 2000 ppm and 23000 ppm |
| VOCs ($CH_4$) | Assume 0 ppm in fresh air or use values reported by air monitoring data suppliers | 2 point calibration: zero point and ~3-4% spike |

When low concentration gases are encountered, the veracity of the measurement can be tested by varying the dilution and/or immediately zero calibrating the relevant sensor(s). This is particularity useful to prevent false positives from errant sensors.

Figure 16:
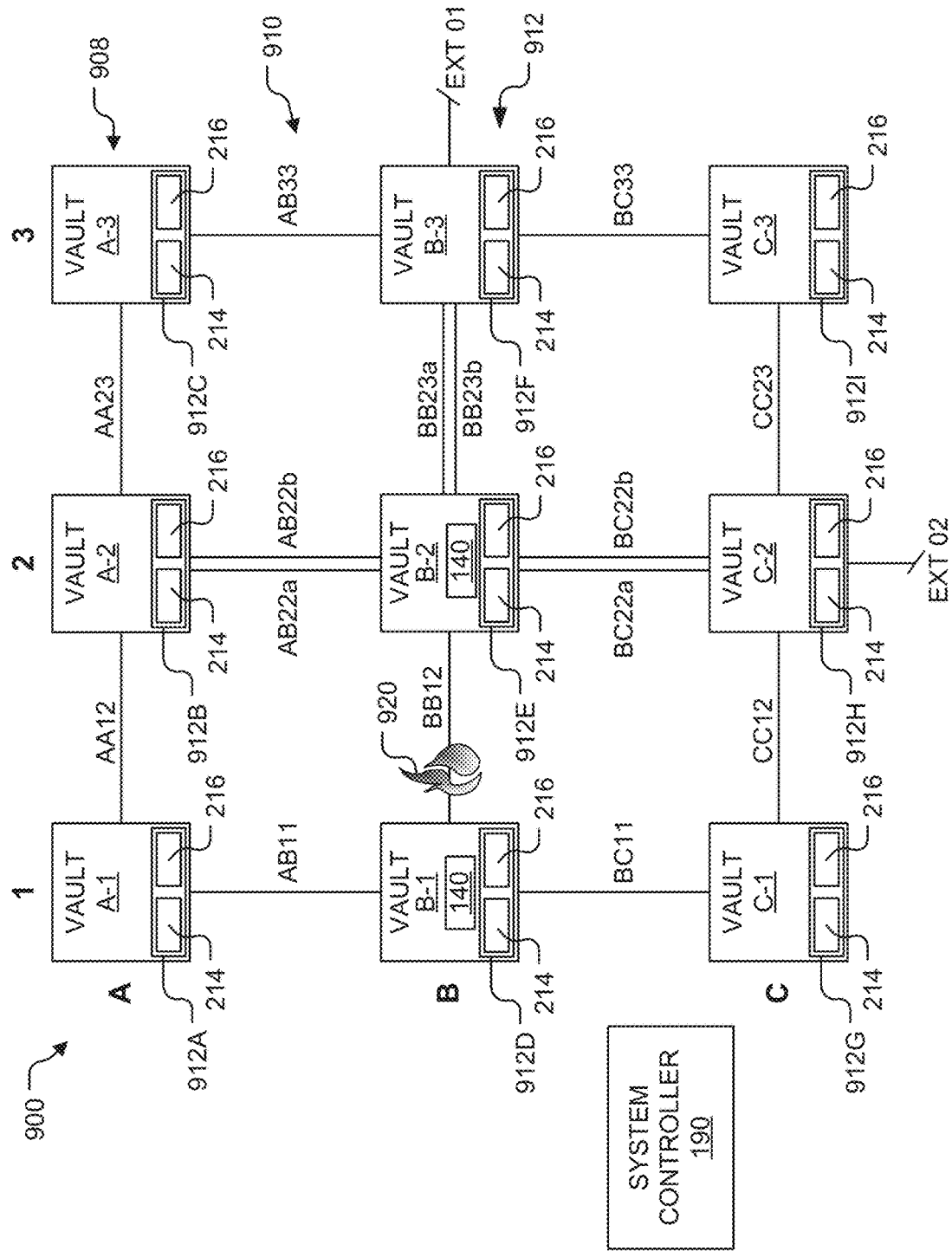
FIG. 16 is an illustration of a network of underground vaults in which a fire is occurring in a connection interconnecting two of the vaults.

FIG. 16 illustrates a simplified network 900 of underground vaults 908 (e.g., each like the vault 112) and underground connections 910 (e.g., each like the connections 118A-118J). Each of the connections 910 may be characterized as being an underground gas source. The network 900 includes at least one monitor 912 (like the monitor 126 illustrated in FIG. 1) and the System Controller 190.

In FIG. 16, the vaults 908 include nine vaults A-1 to A-2, B-1 to B-3, and C-1 to C-3. One or more of the vaults 908 may house electrical equipment and/or electrical cables (e.g., like the electrical equipment 119 of FIG. 1). Each of the vaults 908 may be characterized as being a node. Thus, FIG. 1 shows a simple nine-node network with two external connections Ext 01 and Ext 02. The external connection Ext 01 is connected to the vault B-3 and the external connection Ext 02 is connected to the vault C-2. Optionally, one or more of the vaults 908 may include the manhole event suppression system 140.

In the embodiment illustrated, the connections 910 include connections AA12, AA23, BB12, BB23a, BB23b, CC12, CC23, AB11, AB22a, AB22b, AB33, BC11, BC22a, BC22b, and BC33. Each of the connections 910 connects a pair of the vaults 908 together. For example, the connection AA12 connects the pair of vaults A-1 and A-2 together. Each of the connections 910 may be implemented as conduit, duct, or pipe. Some of the connections 910 include at least one cable that extends therethrough. If a connection includes one or more cables, a gap may be defined between the cable(s) and the connection. Such a gap provides fluidic communication between the connected vaults. Thus, a fluidic flow may be present between the connected vaults. In some cases, a technique referred to as duct plugging, which involves installing a plug between the cable(s) and the connection, may be used to limit such fluidic flow. Unfortunately, all such duct plugs are likely to leak after aging and especially if a fire (oxidative decomposition, pyrolysis, and/or plasmatization) occurs and creates a positive pressure in the gap defined between the cable(s) and the connection. Thus, generally speaking, the connections 910 allow at least some communication between the vaults 908.

For ease of illustration, FIG. 16 omits connections (e.g., conduits) between building(s) owned by the vault owner's customers and one or more of the vaults 908 and/or the connections 910. These connections provide electrical and fluidic communication with one or more adjacent buildings that may serve as pathways for dangerous gases to enter customer premises. Additionally, these connections may provide additional sources of undesirable gases inside the network 900.

The at least one monitor 912 has been illustrated as monitors 912A-912I positioned inside the vaults A-1 to A-2, B-1 to B-3, and C-1 to C-3, respectively. However, this is not a requirement. The network 900 may include any number of monitors each like the monitors 912A-912I installed in any of the vaults 908 and/or the connections 910.

The System Controller 190 communicates over wireless or wired connections with the monitors 912A-912I. The monitors 912A-912I are each configured to send sensor data captured by the sensors 214 and 216 to the System Controller 190. By way of a non-limiting example, the System Controller 190 may be implemented as a computing device 12 illustrated in FIG. 3 and described below.

FIG. 16 illustrates a fire 920 (oxidative decomposition, pyrolysis, and/or plasmatization) in the connection BB12 connecting the vaults B-1 and B-2.

In this example, the fire detection sensor(s) 216 will be described as being implemented as chemical or gas concentration sensors. Such gas concentration sensors are not defined and can utilize a variety of physical or chemical technologies, such as infra-red absorbance, florescence quenching, electro-chemical, thermal-conductivity, and/or flame ionization. Gases to be tested for the presence of at least one analyte are conveyed to the sensors (e.g., by tubing or ducting). For these types of sensors, which are each located in a single vault, to determine where the fire 920 is located in the network 900, complicated plumbing is required to draw gas from every possible source of the analyte(s) of interest. For example, to determine which of the connections AB11, BB12, and BC11 that exit from the vault B-1 harbors the fire 920, the gases emanating from the connections AB11, BB12, and BC11 must be sampled independently by individual sets of sensors or a conveyance means must be used to convey a sample from each location to a central sensor package. The conveyance means may include at least one tube, appropriate tubing connectors, at least one pump, and valves actuated by the System Controller 190. The conveyance means delivers a sample of gases collected from each of the connections AB11, BB12, and BC11 to the central sensor package.

While FIG. 16 illustrates the fire 920 (oxidative decomposition, pyrolysis, and/or plasmatization) occurring in the connection BB12, one of ordinary skill in the art would recognize that the illustrated fire is only one of many possible sources of dangerous gases. Other sources include, but are not limited to, natural gas leaks from nearby pipelines, liquid-phase gasoline or diesel plumes, hydrogen sulfide, and volatile organic compounds (VOCs) from biological decomposition.

When the manhole event suppression system 140 is deployed in each of the vaults 908, it is possible to narrow down the location of the offending fire or gas source. The exhaust rates of the relevant manhole event suppression systems 140 may be set such that desired pressure differentials between the external and internal atmospheres 122 and 124 (see FIG. 1) can be established. Then, a flow of one or more gases created by the fire 920 (or fire by-product(s)) into two or more the vaults 908 measured and used to determine where the fire 920 is located. For example, if the manhole event suppression systems 140 operating in each of the vault B-1 and B-2 have about the same exhaust rates, the vault B-1 and B-2 have about the same negative pressure differential between the external and internal atmospheres 122 and 124 (see FIG. 1). Thus, the flow rate of a first portion of the fire by-product(s) created by the fire 920 flowing into the vault B-1 would be about twice that of the flow rate of a second portion of the fire by-product(s) flowing into the vault B-2 because pneumatic resistance from the fire 920 to the vault B-1 is about half the pneumatic resistance from the fire 920 to the vault B-2. Depending on the size of the fire 920, those of the vaults 908 adjacent to the vaults B-1 and B-2 may also experience small increases in the fire by-product(s), but these increases would be considerably less and considerably delayed by active ventilation generated by the manhole event suppression systems 140 in the vaults B-1 and B-2 and a distance (e.g., several hundred feet) between the vaults. Thus, the relative concentrations of the analytes and their time of arrival can be used to "triangulate" the connection that likely harbors the fire 920 (or gas source) and determine the approximate location of the fire 920 (or gas source). When more than one of the connections 910 joins two of the vaults 908 together, it may not be possible to identify the connection harboring the fire 920 (or gas source), but connections to other vaults can be eliminated from consideration during troubleshooting.

Computing Device

Figure 17:
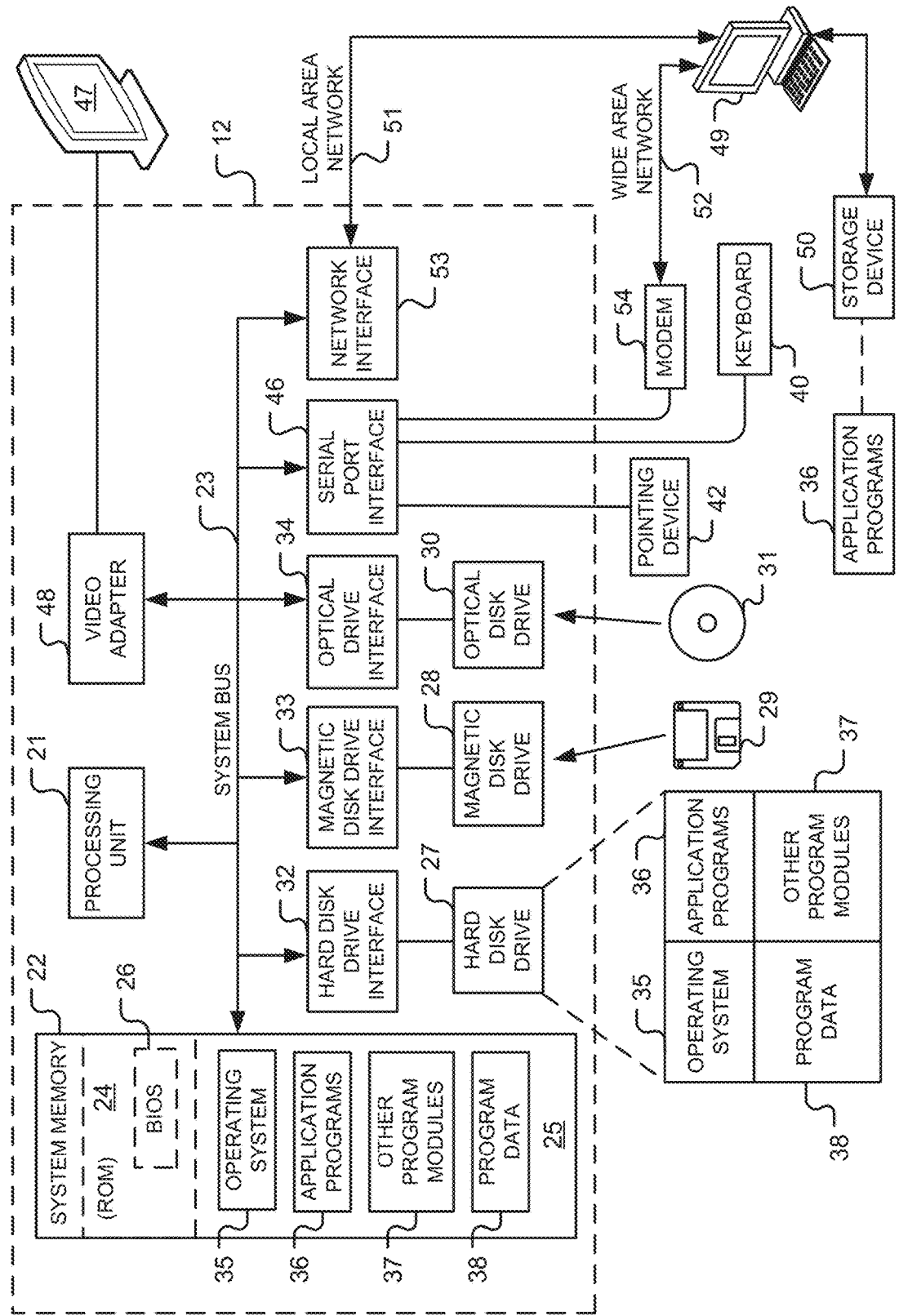
FIG. 17 is a diagram of a hardware environment and an operating environment in which the System Controller of FIGS. 1 and 3 may be implemented.

FIG. 17 is a diagram of hardware and an operating environment in conjunction with which implementations of the System Controller 190 (see FIGS. 1 and 3) may be practiced. The description of FIG. 17 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those of ordinary skill in the art will appreciate that implementations may be practiced with other computer system configurations, including hand-held devices, multiprocessor systems, microprocessor-based or programmable consumer electronics, network PCs, minicomputers, mainframe computers, and the like. Implementations may also be practiced in distributed computing environments (e.g., cloud computing platforms) where tasks are performed by remote processing devices that are linked through a communications network. In a distributed computing environment, program modules may be located in both local and remote memory storage devices.

The exemplary hardware and operating environment of FIG. 17 includes a general-purpose computing device in the form of the computing device 12. The System Controller 190 (see FIGS. 1 and 3) may be substantially identical to the computing device 12. By way of non-limiting examples, the computing device 12 may be implemented as a laptop computer, a tablet computer, a web enabled television, a personal digital assistant, a game console, a smartphone, a mobile computing device, a cellular telephone, a desktop personal computer, and the like.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like.

The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those of ordinary skill in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including the operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types of physical feedback (e.g., a force feed back game controller).

The input devices described above are operable to receive user input and selections. Together the input and display devices may be described as providing a user interface.

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 17 include a local-area network (LAN) 51 and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

In some embodiments, the system memory 22 stores computer executable instructions that when executed by one or more processors cause the one or more processors to perform all or portions of one or more of the methods (including the method 200-A illustrated in FIG. 7A, the methods 200-C to 200-W illustrated in FIGS. 7C-7W, and the method 300, 350, 400, 500, 600, 700, and 800 illustrated in FIGS. 9, 10, 11, 12, 13, 14, and 15, respectively) described above. Such instructions may be stored on one or more non-transitory computer-readable media.

In some embodiments, the system memory 22 stores computer executable instructions that when executed by one or more processors cause the one or more processors to generate the notifications identified in FIGS. 7F-7H and described above. Such instructions may be stored on one or more non-transitory computer-readable media.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Conjunctive language, such as phrases of the form "at least one of A, B, and C," or "at least one of A, B and C," (i.e., the same phrase with or without the Oxford comma) unless specifically stated otherwise or otherwise clearly contradicted by context, is otherwise understood with the context as used in general to present that an item, term, etc., may be either A or B or C, any nonempty subset of the set of A and B and C, or any set not contradicted by context or otherwise excluded that contains at least one A, at least one B, or at least one C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}, and, if not contradicted explicitly or by context, any set having {A}, {B}, and/or {C} as a subset (e.g., sets with multiple "A"). Thus, such conjunctive language is not generally intended to imply that certain embodiments require at least one of A, at least one of B, and at least one of C each to be present. Similarly, phrases such as "at least one of A, B, or C" and "at least one of A, B or C" refer to the same as "at least one of A, B, and C" and "at least one of A, B and C" refer to any of the following sets: {A}, {B}, {C}, {A, B}, {A, C}, {B, C}, {A, B, C}, unless differing meaning is explicitly stated or clear from context.

Accordingly, the invention is not limited except as by the appended claims.

The invention claimed is:

1. A system comprising:
   a first sensor to be installed inside a first underground vault;
   a second sensor to be installed inside a second underground vault and to detect a different property than the first sensor and being complimentary to the first sensor with respect to a particular conclusion; and
   a system controller comprising at least one processor connected to memory storing instructions executable by the at least one processor, the instructions, when executed by the at least one processor, causing the at least one processor to (a) determine a first state of the first sensor based at least in part on a first sensor reading, (b) when the first state is indicative of the particular conclusion, calculate a calculated value based at least in part on a first value associated with the first state and a second value associated with a second state determined for the second sensor, (c) determine an alarm state based at least in part on the calculated value, and (d) notify a user of the alarm state.

2. The system of claim 1, wherein the particular conclusion is that a fire is present.

3. The system of claim 2, wherein the first sensor is a carbon dioxide ($CO_2$) sensor, and the second sensor is a carbon monoxide (CO) sensor.

4. The system of claim 2, wherein the first sensor is a carbon dioxide ($CO_2$) sensor, and the second sensor is a temperature sensor.

5. The system of claim 1, wherein the calculated value is calculated based at least in part on a weighted sum of the first and second values.

6. The system of claim 1, wherein the second underground vault is adjacent to the first underground vault.

7. The system of claim 1, wherein the second state is determined based at least in part on a second sensor reading from the second sensor, and the system controller obtains the second sensor reading after the first sensor detects a suspected alarm condition.

8. The system of claim 1, further comprising:
   a third sensor that measures different properties than the first sensor, the instructions, when executed by the at least one processor, causing the at least one processor to obtain a third sensor reading from the third sensor and determine a third state based at least in part on the third sensor reading, the third state being associated with a third value, the calculated value to be calculated based at least in part on the first, second, and third values.

9. The system of claim 1, wherein determining the alarm state comprises comparing the calculated value and a threshold value.

10. The system of claim 1, further comprising:
    a third sensor that is identical to the first sensor, the instructions, when executed by the at least one processor, causing the at least one processor to obtain a third sensor reading from the third sensor and determine a third state based at least in part on the third sensor reading, the third state being associated with a third value, the calculated value to be calculated based at least in part on the first, second, and third values.

11. A method comprising:
    obtaining a first sensor reading from a first sensor installed inside a first underground vault;
    obtaining a second sensor reading from a second sensor inside a second underground vault, the second sensor being complimentary to the first sensor with respect to a particular conclusion, the second sensor detecting a different property than the first sensor;
    determining a first state for the first sensor based at least in part on the first sensor reading;
    determining a second state for the second sensor based at least in part on the second sensor reading;
    calculating a calculated value based at least in part on the first and second states when the first state is indicative of the particular conclusion;
    determining an alarm state based at least in part on the calculated value; and
    notifying a user of the alarm state.

12. The method of claim 11, wherein the particular conclusion is that a fire is present.

13. The method of claim 12, wherein the first sensor is a carbon dioxide ($CO_2$) sensor, and the second sensor is a carbon monoxide (CO) sensor.

14. The method of claim 12, wherein the first sensor is a carbon dioxide ($CO_2$) sensor, and the second sensor is a temperature sensor.

15. The method of claim 11, further comprising:
    installing the first sensor inside the first underground vault.

16. The method of claim 15, further comprising:
installing the second sensor inside the second underground vault.

17. The method of claim 11, wherein calculating the calculated value comprises summing values associated with the first and second states.

18. The method of claim 11, further comprising:
installing the second sensor in the second underground vault, the second underground vault to be adjacent to the first underground vault.

19. The method of claim 11, further comprising:
determining the first sensor has detected a suspected alarm condition, the second sensor reading being obtained after it is determined that the first sensor has detected the suspected alarm condition.

20. The method of claim 11, further comprising:
obtaining a third sensor reading from a third sensor that measures different properties than the first sensor; and
determining a third state for the third sensor based at least in part on the third sensor reading, the calculated value to be calculated based at least in part on the first, second, and third states.

21. The method of claim 11, wherein determining the alarm state comprises comparing the calculated value and a threshold value.

22. The method of claim 11, further comprising:
obtaining a third sensor reading from a third sensor installed in a third underground vault that is different from the first and second underground vaults; and
determining a third state for the third sensor based at least in part on the third sensor reading, the calculated value to be calculated based at least in part on the first, second, and third states.

23. A method comprising:
determining a first state for a first sensor installed inside a first underground vault based at least in part on a first sensor reading collected by the first sensor;
determining a second state for a second sensor installed inside a second underground vault based at least in part on a second sensor reading collected by the second sensor, the second underground vault being different from the first underground vault;
if the first state is indicative of a particular conclusion, determining an alarm state based at least in part on a calculated value calculated based at least in part on first and second values associated with the first and second states, respectively; and
notifying a user of the alarm state.

24. The method of claim 23, wherein the particular conclusion is that a fire is present.

* * * * *